US012214052B2

(12) United States Patent
Julien et al.

(10) Patent No.: US 12,214,052 B2
(45) Date of Patent: Feb. 4, 2025

(54) NANOPARTICLE PLATFORM FOR ANTIBODY AND VACCINE DELIVERY

(71) Applicants: The Hospital for Sick Children, Toronto (CA); The Governing Council of the University of Toronto, Toronto (CA)

(72) Inventors: Jean-Philippe Julien, Toronto (CA); Taylor Sicard, Toronto (CA); Anthony Semesi, Toronto (CA); Bebhinn Treanor, Toronto (CA); Tiantian Zhao, Toronto (CA); Edurne Rujas Diez, Toronto (CA)

(73) Assignees: The Hospital for Sick Children, Toronto (CA); The Governing Council of the University of Toronto, Toronto (CA)

(*) Notice: Subject to any disclaimer, the term of this patent is extended or adjusted under 35 U.S.C. 154(b) by 198 days.

(21) Appl. No.: 16/636,141

(22) PCT Filed: Aug. 3, 2018

(86) PCT No.: PCT/CA2018/050954
§ 371 (c)(1),
(2) Date: Feb. 3, 2020

(87) PCT Pub. No.: WO2019/023811
PCT Pub. Date: Feb. 7, 2019

(65) Prior Publication Data
US 2020/0179532 A1 Jun. 11, 2020

Related U.S. Application Data

(60) Provisional application No. 62/541,209, filed on Aug. 4, 2017.

(51) Int. Cl.
| | | |
|---|---|---|
| *A61K 47/69* | (2017.01) | |
| *A61K 39/015* | (2006.01) | |
| *A61K 47/68* | (2017.01) | |
| *C07K 14/445* | (2006.01) | |
| *B82Y 5/00* | (2011.01) | |

(52) U.S. Cl.
CPC ........ *A61K 47/6929* (2017.08); *A61K 39/015* (2013.01); *A61K 47/68* (2017.08); *C07K 14/445* (2013.01); *B82Y 5/00* (2013.01); *C07K 2317/55* (2013.01); *C07K 2317/622* (2013.01); *C07K 2317/77* (2013.01); *C07K 2317/92* (2013.01); *C07K 2319/735* (2013.01)

(58) Field of Classification Search
CPC ................................................. A61K 47/6929
See application file for complete search history.

(56) References Cited

U.S. PATENT DOCUMENTS

| | | | |
|---|---|---|---|
| 7,981,632 B2 | 7/2011 | Schmidt | |
| 8,546,337 B2 | 10/2013 | Burkhard | |
| 8,722,033 B2* | 5/2014 | Towne | .................... A61P 37/00 |
| | | | 530/388.1 |
| 2003/0083474 A1 | 5/2003 | Schmidt | |
| 2007/0184526 A1 | 8/2007 | Smith et al. | |
| 2010/0222501 A1 | 9/2010 | Murthy et al. | |
| 2014/0302527 A1* | 10/2014 | Lee | ...................... G01N 33/588 |
| | | | 530/387.3 |
| 2015/0110825 A1 | 4/2015 | Sasisekharan et al. | |

FOREIGN PATENT DOCUMENTS

| | | |
|---|---|---|
| EP | 3181586 | 6/2017 |
| WO | 9504069 A1 | 2/1995 |
| WO | 2004076670 A1 | 9/2004 |
| WO | 2005020889 A2 | 3/2005 |
| WO | 2007047831 A2 | 4/2007 |
| WO | 2014031727 A1 | 2/2014 |
| WO | 2016109792 A2 | 7/2016 |
| WO | 2019023812 A1 | 2/2019 |

OTHER PUBLICATIONS

Dehal, P. K., et al., 2010, Magnetizable antibody-like proteins, Biotechnol. J. 5:596-604.*
Falvo, E., et al., 2013, Antibody-drug conjugates: targeting melanoma with cisplatin encapsulated in protein-cage nanoparticles based on human ferritin, Nanoscale 5:12278-12285.*
Demartis, S., et al., Apr. 2001, Selective targeting of tumour neovasculature by a radiohalogenated human antibody fragment specific for the ED-B domain of fibronectin, Eur. J. Nuc. Med. 28(4):534-539.*
Dehal et al. "Magnetizable antibody-like proteins" Biotechnology Journal, 5(6):596-604 (2010) (Abstract only).
Falvo et al. "Antibody-drug conjugates: targeting melanoma with cisplatin encapsulated in protein-cage nanoparticles based on human ferritin" Nanoscale, 5:12278-12285 (2013).
Ghisaidoobe et al. "Functionalized protein nanocages as a platform of targeted therapy and immunodetection" Nanomedicine, 10(24):3579-3595 (2015) (Abstract only).
International Search Report and the Written Opinion of the International Searching Authority corresponding to International Patent Application No. PCT/CA2018/050954 (15 pages) (mailed Oct. 22, 2018).
Extended European Search Report corresponding to European Patent Application No. 18841800.8 (9 pages) (dated Apr. 14, 2021).
Jääskeläinen et al. "Biologically Produced Bifunctional Recombinant Protein Nanoparticles for Immunoassays" Analytical Chemistry, 80(3):583-587 (2008).

(Continued)

*Primary Examiner* — Jeffrey S Parkin
(74) *Attorney, Agent, or Firm* — Goodwin Procter LLP

(57) ABSTRACT

A fusion protein comprises a nanocage monomer; and an antibody or fragment thereof linked to the nanocage monomer, the antibody or fragment thereof comprising a first member of a binding pair; wherein a plurality of the fusion proteins self-assemble to form a nanocage in which a plurality of the antibodies or fragments thereof decorate the exterior surface of the nanocage, whereby the first member of the binding pair is exposed for interacting with a second member of a binding pair.

7 Claims, 56 Drawing Sheets

Specification includes a Sequence Listing.

(56) References Cited

OTHER PUBLICATIONS

Dame et al. "Structure of the Gene Encoding the Immunodominant Surface Antigen on the Sporozoite of the Human Malaria Parasite Plasmodium falciparum" Science, 225(4662):593-599 (1984).
Foquet et al. "Vaccine-induced monoclonal antibodies targeting circumsporozoite protein prevent Plasmodium falciparum infection" The Journal of Clinical Investigation, 124(1):140-144 (2014).
Ghisaidoobe et al. "Functionalized protein nanocages as a platform of targeted therapy and immunodetection" Nanomedicine, 10(24):3579-3595 (2015).
Hattori et al. "Antigen clasping by two antigen-binding sites of an exceptionally specific antibody for histone methylation" Proceedings of the National Academy of Sciences USA, 113(8):2092-2097 (2016).
Masella et al. "PANDAseq: PAired-eND Assembler for Illumina sequences" BMC Bioinformatics, 13:31 (2012).
Oyen et al. "Structural basis for antibody recognition of the NANP repeats in Plasmodium falciparum circumsporozoite protein" Proceedings of the National Academy of Sciences USA, 114(48):E10438-E10445 (2017).
Riley et al. "Immune mechanisms in malaria: new insights in vaccine development" Nature Medicine, 19(2):168-178 (2013).
Scheres, Sjors H. W. "A Bayesian View on Cryo-EM Structure Determination" Journal of Molecular Biology, 415(2):406-418 (2012).
Tan et al. "A public antibody lineage that potently inhibits malaria infection by dual binding to the circumsporozoite protein" Nature Medicine, 24(4):401-407 (2018).
Tewari et al. "Poly(I:C) is an effective adjuvant for antibody and multifunctional CD4+ T cell responses to Plasmodium falciparum circumsporozoite protein (CSP) and αDEC-CSP in Non Human Primates" Vaccine, 28(45):7256-7266 (2010).
Wardemann et al. "Predominant Autoantibody Production by Early Human B Cell Precursors" Science, 301(5638):1374-1377 (2003).
Aaron L. Nelson "Antibody fragments: Hope and hype" mAbs 2:1, pp. 77-83; Jan./Feb. 2010; Landes Bioscience.
Burn Aschner et al., "A multi-specific, multi-affinity antibody platform neutralizes sarbecoviruses and confers protection against SARS-COV-2 in vivo." Sci Transl Med. May 24, 2023;15(697).
Rujas, E. et al. Functional Optimization of Broadly Neutralizing HIV-1 Antibody 10E8 by Promotion of Membrane Interactions. J. Virol. (2018). doi: 10.1 128/jvi.02249-17.
Jaaskelainen et al. "Biologically produced bifunctional recombinant protein nanoparticles for immunoassays" Analytical Chemistry, vol. 80, No. 3, pp. 583-587, Feb. 1, 2008.
Japanese Office Action issued in Japanese Patent Application No. 2023-066391 dated Jun. 26, 2024, 8 pages.
Adams et al. "PHENIX: A comprehensive Python-based system for macromolecular structure solution" Acta Crystallographica Section D, 66:213-221 (2010).
Akdis et al. "Epitope-specific T Cell Tolerance to Phospholipase A2 in Bee Venom Immunotherapy and Recovery by IL-2 and IL-15 In Vitro" Journal of Clinical Investigation, 98:1676-1683 (1996).
Arnon et al. "Complexes and Conjugates of CIS-Pt for Immunotargeted Chemotherapy" Advances in Experimental Medicine and Biology, 303:79-90 (1991).
Bauer et al. "Modulation of the allergic immune response in BALB/c mice by subcutaneous injection of high doses of the dominant T cell epitope from the major birch pollen allergen Bet v 1" Clinical & Experimental Immunology, 107(3):536-541 (1997).
Cao et al. "Vaccination with a multi-epitopic recombinant allergen induces specific immune deviation via T-cell anergy" Immunology, 90:46-51 (1997).
Carter et al. "CD19: Lowering the Threshold for Antigen Receptor Stimulation of B Lymphocytes" Science, 256(5053):105-107 (1992).
Choe et al. "Fc-Binding Ligands of Immunoglobulin G: An Overview of High Affinity Proteins and Peptides" Materials, 9(994):1-17 (2016).
Davies et al. "Repetitive sequences in malaria parasite proteins" FEMS Microbiology Reviews, 41:923-940 (2017).
Dekosky et al. "In-depth determination and analysis of the human paired heavy- and light-chain antibody repertoire" Nature Medicine, 21:86-91 (2015).
Eisenberg et al. "Analysis of Membrane and Surface Protein Sequences with the Hydrophobic Moment Plot" Journal of Molecular Biology, 179:125-142 (1984).
Emsley et al. "Features and development of Coot" Acta Crystallographica Section D, 66:486-501 (2010).
Enea et al. "DNA Cloning of Plasmodium falciparum Circumsporozoite Gene: Amino Acid Sequence of Repetitive Epitope" Science, 225:628-630 (1984).
Fisher et al. "T-dependent B cell responses to Plasmodium induce antibodies that form a high-avidity multivalent complex with the circumsporozoite protein" PLoS Pathogens, 13:e1006469 (2017).
Ghasparian et al. "Crystal structure of an NPNArepeat motif from the circumsporozoite protein of the malaria parasite Plasmodium falciparum" ChemComm, 14:174-176 (2006).
Greenfield et al. "Evaluation in Vitro of Adriamycin Immunoconjugates Synthesized Using an Acid-sensitive Hydrazone Linker" Cancer Research, 50:6600-6607 (1990).
Gupta et al. "Change-O: A toolkit for analyzing large-scale B cell immunoglobulin repertoire sequencing data" Bioinformatics, 31(20):3356-3358 (2015).
Hoyne et al. "Inhibition of T-cell responses by feeding peptides containing major and cryptic epitopes: studies with the Der p I allergen" Immunology, 83:190-195 (1994).
Izard et al. "Principles of quasi equivalence and Euclidean geometry govern the assembly of cubic and dodecahedral cores of pyruvate dehydrogenase complexes" Proceedings of the National Academy of Sciences USA, 96:1240-1245 (1999).
Jardine et al. "Rational HIV immunogen design to target specific germline B cell receptors" Science, 340(6133):711-716 (2013).
Kabsch, Wolfgang "XDS" Acta Crystallographica Section D, 66:125-132 (2010).
Kanekiyo et al. "Self-Assembling Influenza Nanoparticle Vaccines Elicit Broadly Neutralizing H1N1 Antibodies" Nature, 499(7456):102-106 (2013).
Kang et al. "Scfv-ferritin chimera as a targeted nanocage with high antigen-binding affinity" Fourth International Conference on Multifunctional, Hybrid and Nanomaterials, Poster Program, p. 1.048 (51 pages) (2015).
Kaufmann et al. "Amplification and Expression of Sequences Cotransfected with a Modular Dihydrofolate Reductase Complementary DNA Gene" Journal of Molecular Biology, 159:601-621 (1982).
Khoshnejad et al. "Vascular Accessibility of Endothelial Targeted Ferritin Nanoparticles" Bioconjugate Chemistry, 27(3):628-637 (2016).
Kisalu et al. "A human monoclonal antibody prevents malaria infection by targeting a new site of vulnerability on the parasite" Nature Medicine, 24(4):408-416 (2018).
Kiseleva et al. "Use of antibodies to DNA modified by transdiaminodichloroplatinum, for identification of specific DNA sequences" Molecular Biology (Moscow), 25(2):508-514 (1991) (English translation of abstract).
Köhler et al. "Autoreactive B Cell Receptors Mimic Autonomous Pre-B Cell Receptor Signaling and Induce Proliferation of Early B Cells" Immunity, 29:912-921 (2008).
McCoy et al. "Phaser crystallographic software" Journal of Applied Crystallography, 40:658-674 (2007).
Meixlsperger et al. "Conventional Light Chains Inhibit the Autonomous Signaling Capacity of the B Cell Receptor" Immunity, 26:323-333 (2007).
Mordmüller et al. "Sterile protection against human malaria by chemoattenuated PfSPZ vaccine" Nature, 542:445-449 (2017).
Morin et al. "Collaboration gets the most out of software" eLife, 2:e01456 (2013).
Murugan et al. "Clonal selection drives protective memory B cell responses in controlled human malaria infection" Science Immunology, 3:eaap8029 (2018).
Nielsen et al. "Identification of prokaryotic and eukaryotic signal peptides and prediction of their cleavage sites" Protein Engineering, 10(1):1-6 (1997).

(56) References Cited

OTHER PUBLICATIONS

Potocnjak et al. "Monovalent fragments (Fab) of monoclonal antibodies to a sporozoite surface antigen (Pb44) protect mice against malarial infection" Journal of Experimental Medicine, 151:1504-1513 (1980).
Scahill et al. "Expression and characterization of the product of a human immune interferon cDNA gene in Chinese hamster ovary cells" Proceedings of the National Academy of Sciences USA, 80:4654-4659 (1983).
Shokri et al. "Cell and process design for targeting of recombinant protein into the culture medium of *Escherichia coli*" Applied Microbiology and Biotechnology, 60(6):654-664 (2003).
Sliepen et al. "Presenting native-like HIV-1 envelope trimers on ferritin nanoparticles improves their immunogenicity" Retrovirology, 12(82):1-5 (2015).
Southern et al. "Transformation of mammalian cells to antibiotic resistance with a bacterial gene under control of the SV40 early region promoter" Journal of Molecular and Applied Genetics, 1:327-341 (1982) (Abstract only).
Subramani et al. "Expression of the Mouse Dihydrofolate Reductase Complementary Deoxyribonucleic Acid in Simian Virus 40 Vectors" Molecular and Cellular Biology, 1(9):854-864 (1981).
Sutter et al. "Structural basis of enzyme encapsulation into a bacterial nanocompartment" Nature Structural & Molecular Biology, 15:939-947 (2008).
Tiller et al. "Efficient generation of monoclonal antibodies from single human B cells by single cell RT-PCR and expression vector cloning" Journal of Immunological Methods, 329:112-124 (2008).
Triller et al. "Natural Parasite Exposure Induces Protective Human Anti-Malarial Antibodies" Immunity, 47:1-13 (2017).
Urich et al. "X-ray Structure of a Self-Compartmentalizing Sulfur Cycle Metalloenzyme" Science, 311:996-1000 (2006).
Urlaub et al. "Isolation of Chinese hamster cell mutants deficient in dihydrofolate reductase activity" Proceedings of the National Academy of Sciences USA, 77:4216-4220 (1980).
Von Heinje et al. "A new method for predicting signal sequence cleavage sites" Nucleic Acids Research, 14:4683-4690 (1986).
Watson et al. "Complete Haplotype Sequence of the Human Immunoglobulin Heavychain Variable, Diversity, and Joining Genes and Characterization of Allelic and Copy-Number Variation" American Journal of Human Genetics, 92:530-546 (2013).
Yaari et al. "Models of somatic hypermutation targeting and substitution based on synonymous mutations from high-throughput immunoglobulin sequencing data" Frontiers in Immunology, 4(358):1-12 (2013).
Yoshida et al. "Hybridoma Produces Protective Antibodies Directed Against the Sporozoite Stage of Malaria Parasite" Science, 207:71-73 (1980).
Zavala et al. "Circumsporozoite proteins of malaria parasites contain a single immunodominant region with two or more identical epitopes" Journal of Experimental Medicine, 157:1947-1957 (1983).
Zhang et al. "Self-Assembly in the Ferritin Nano-Cage Protein Superfamily" International Journal of Molecular Sciences, 12:5406-5421 (2011).
Zhang et al. "X-ray Structure Analysis and Crystallographic Refinement of Lumazine Synthase from the Hyperthermophile Aquifex aeolicus at 1.6 A Resolution" Journal of Molecular Biology, 306:1099-1114 (2001).

\* cited by examiner

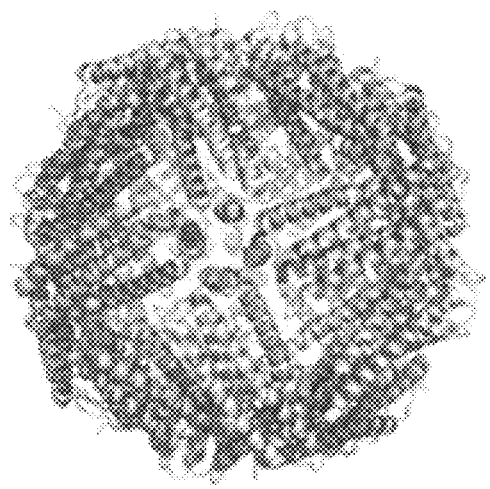
Self-assembling human Ferritin
24 protomers (20k Da each)
Assembled MW: 480 kDa
Diameter: 12 nm
FIG. 1A
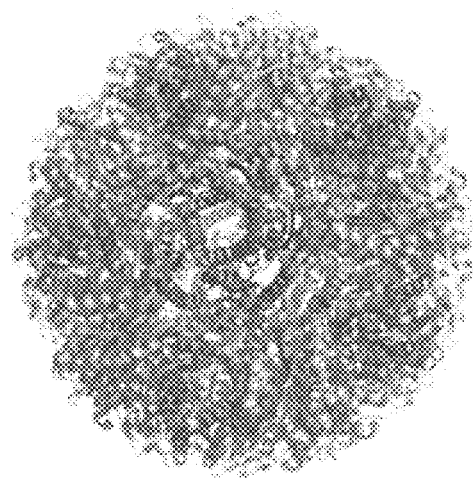
Self-assembling *Aquifex aeolicus*
Lumazine synthase
60 protomers (20k Da each)
Assembled MW: 1.2 Mda
Diameter: 15 nm
FIG. 1B
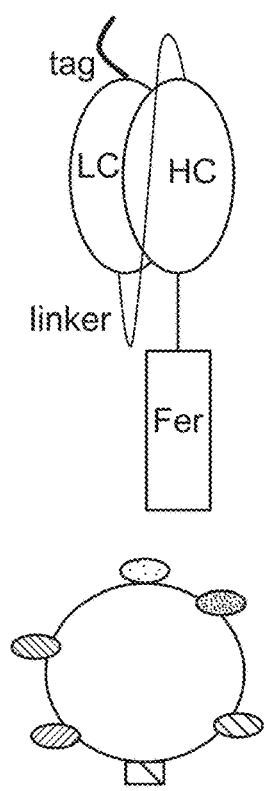
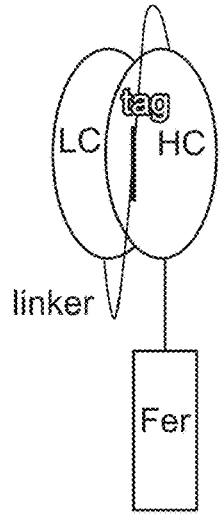
- Tag1-single chain Fab1
- Tag2-single chain Fab2
- Tag3-single chain Fab3
- Tag4-single chain Fab4
- Tag5-single chain Fab5
- single chain Fc
FIG. 1C

CSP-NANP5.5-8xlinker-antibody-HC

NPNANPNANPNANPNANPNANPGGSGGSGGQVQLVESGGGVVQPGRSLRLSCAASG
FTFSNYGMHWVRQAPGKGLEWVAVIWYDGSKKYYADSVKGRFTISRDNSKNTLYL
QMNSLRAEDTAVYYCARVRDSSDYYGDAFDIWGQGTMVTVSS

FIG. 10A

CSP-NANP5.5-10xlinker-antibody-HC

NPNANPNANPNANPNANPNANPGGSGGSGGSGQVQLVESGGGVVQPGRSLRLSCAA
SGFTFSNYGMHWVRQAPGKGLEWVAVIWYDGSKKYYADSVKGRFTISRDNSKNTL
YLQMNSLRAEDTAVYYCARVRDSSDYYGDAFDIWGQGTMVTVSS

FIG. 10B

CSP-NANP5.5-12xlinker-antibody-HC

NPNANPNANPNANPNANPNANPGGSGGSGGSGGSQVQLVESGGGVVQPGRSLRLSCA
ASGFTFSNYGMHWVRQAPGKGLEWVAVIWYDGSKKYYADSVKGRFTISRDNSKNT
LYLQMNSLRAEDTAVYYCARVRDSSDYYGDAFDIWGQGTMVTVSS

FIG. 10C co-transfected in HEK 293 mammalian cells with antibody light chain:

DIQMTQSPSTLSASVGDRVTITCRASQSISSWLAWYQQKPGKAPKLLIYKASNLESGVPL
RFSGSGSGTEFTLTISSLQPDDFATYYCQQYNNYWTFGQGTKVEIKRTVA

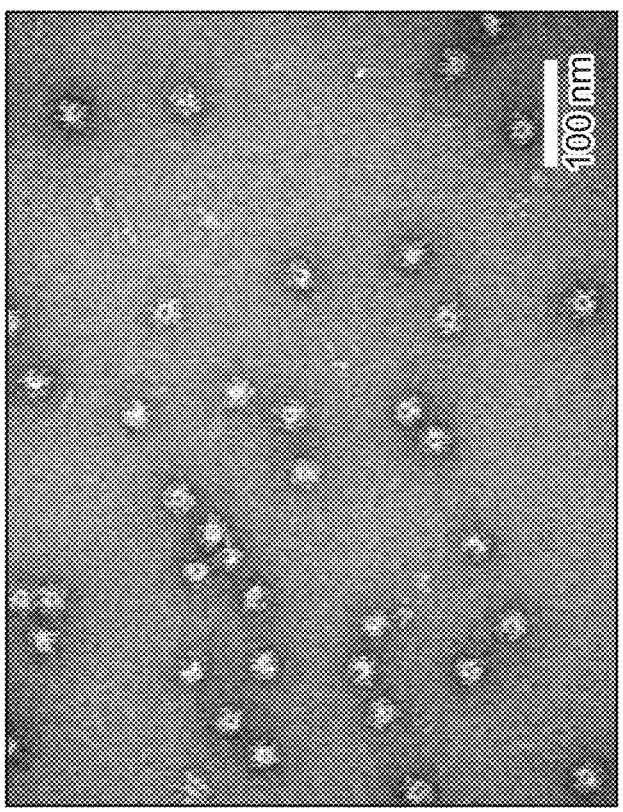
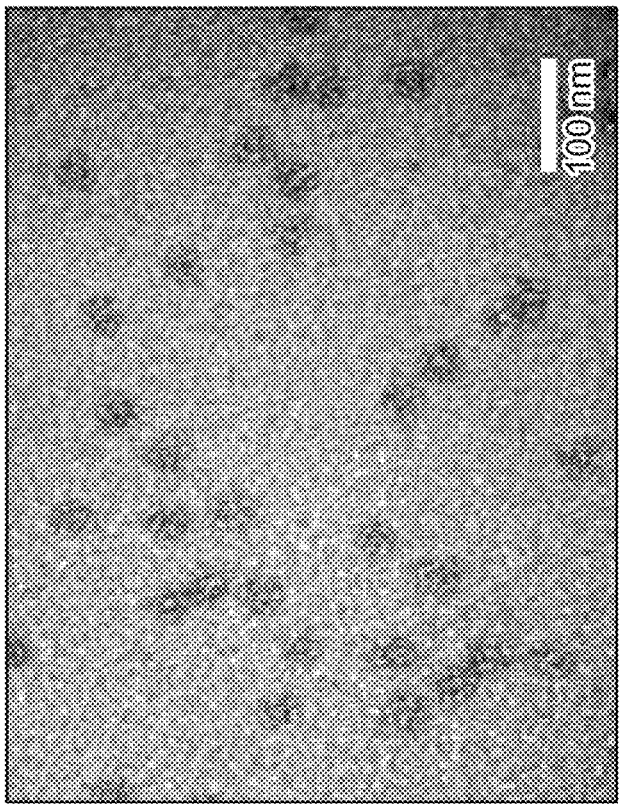
FIG. 21

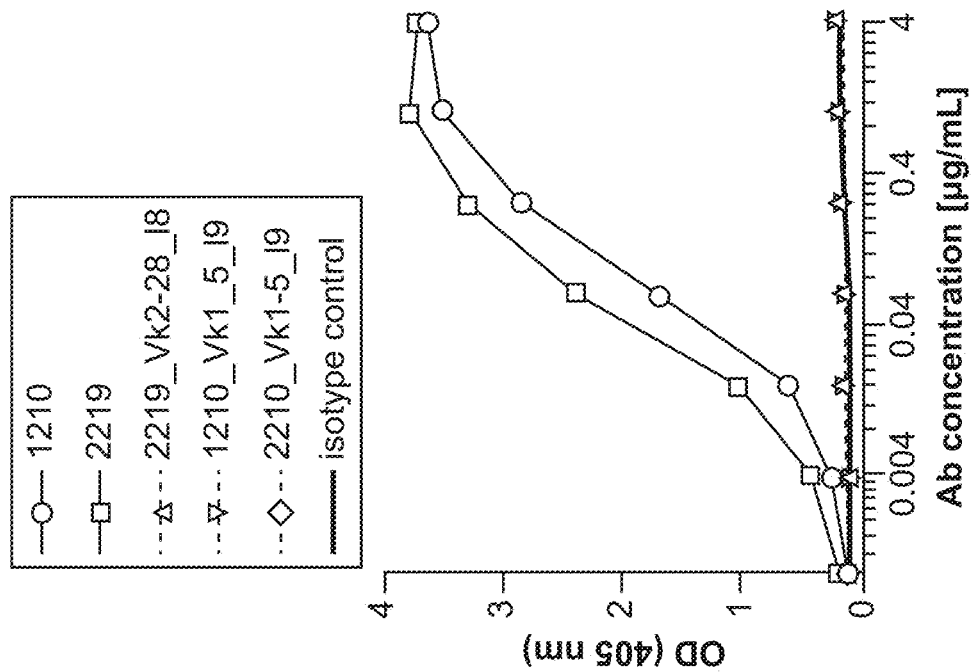
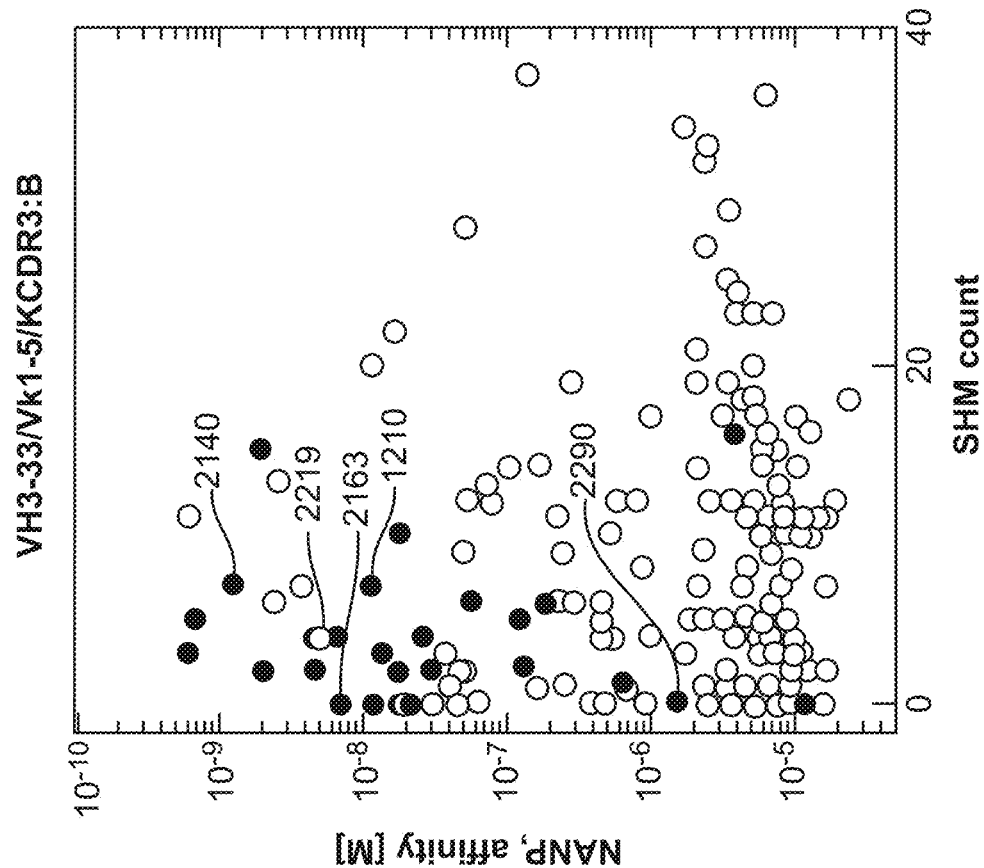
FIG. 25B
FIG. 25A

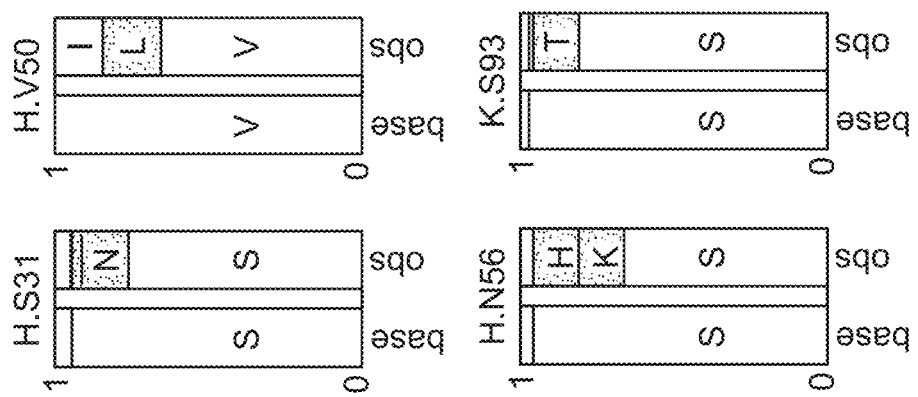
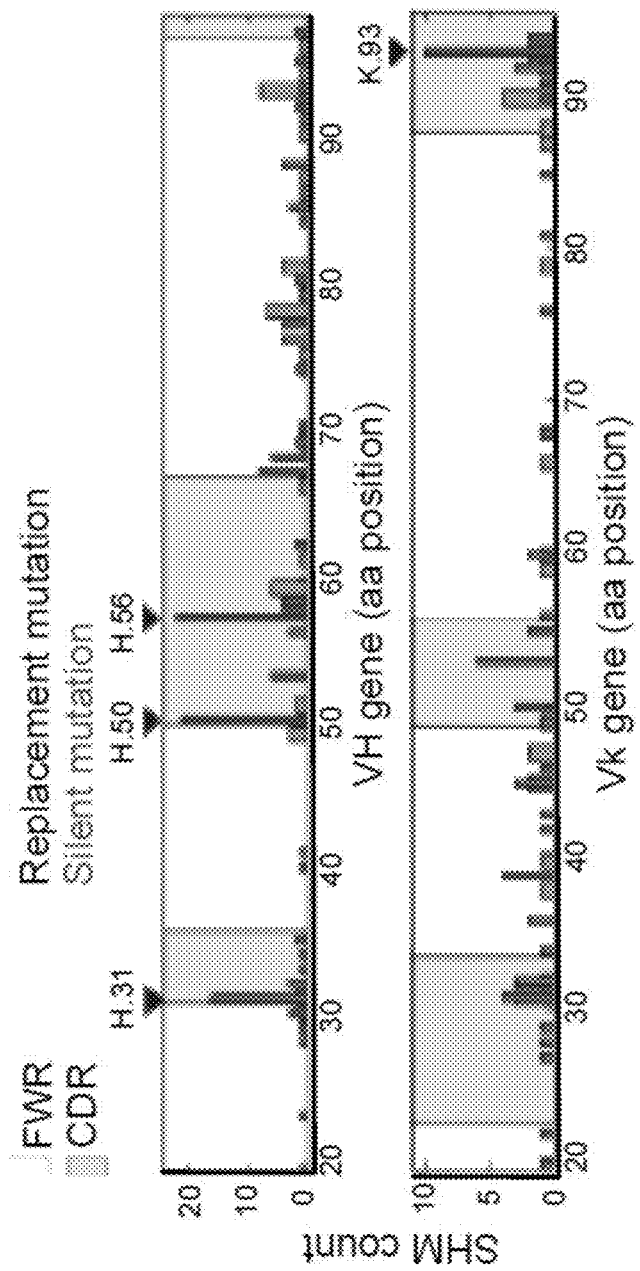
FIG. 25E
FIG. 25F

| Fab | Peptide | Stoichiometry (N) | $K_D$ (nM) | $\Delta H$ (kcal/mol) |
|---|---|---|---|---|
| 1210 | $NANP_5$ | 1.8 ± 0.09 | 286 ± 70 | -20 ± 1 |
| 1210_NS | $NANP_5$ | 1.7 ± 0.24 | 556 ± 36 | -22 ± 1 |
| 1210_YY | $NANP_5$ | 2.1 ± 0.12 | 1538 ± 118 | -14 ± 1 |
| 1210_GL | $NANP_5$ | 1.9 ± 0.12 | 1576 ± 456 | -23 ± 5 |
| 1210 | $NANP_3$ | 0.73 ± 0.09 | 2260 ± 446 | -21 ± 3 |
| 1210_NS | $NANP_3$ | 0.94 ± 0.05 | 2420 ± 370 | -27 ± 5 |
| 1210_YY | $NANP_3$ | 0.88 ± 0.11 | 3405 ± 141 | -7 ± 0.7 |
| 1210_GL | $NANP_3$ | 0.92 ± 0.05 | 3858 ± 573 | -12 ± 2 |

FIG. 30C

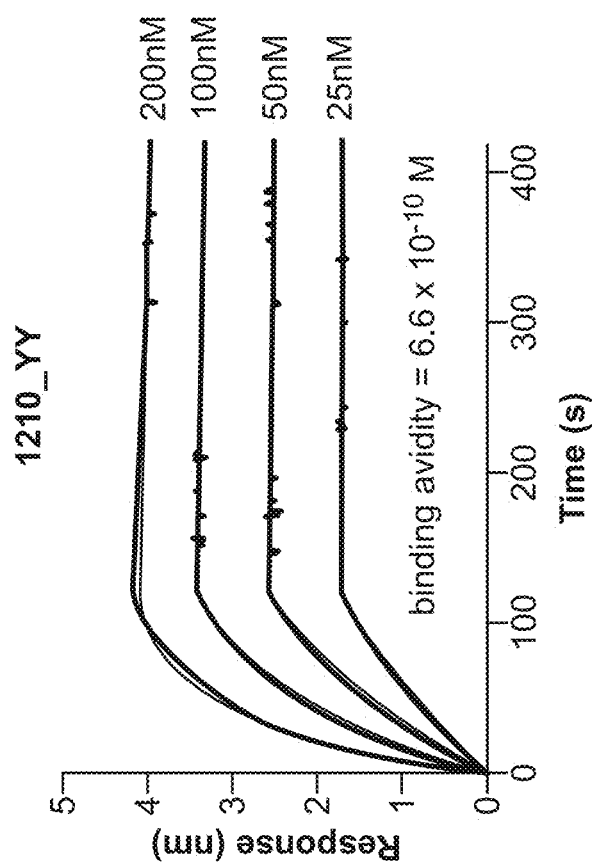
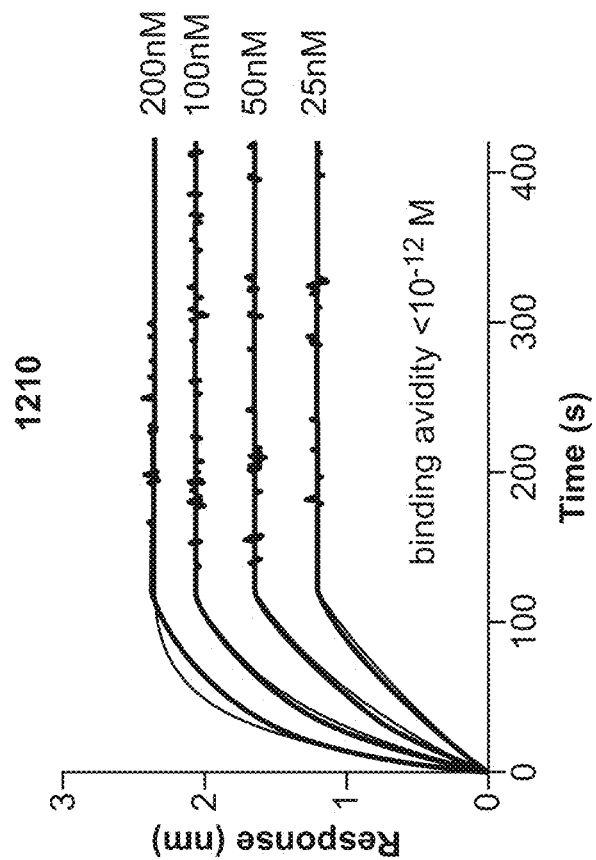
FIG. 31B
FIG. 31A

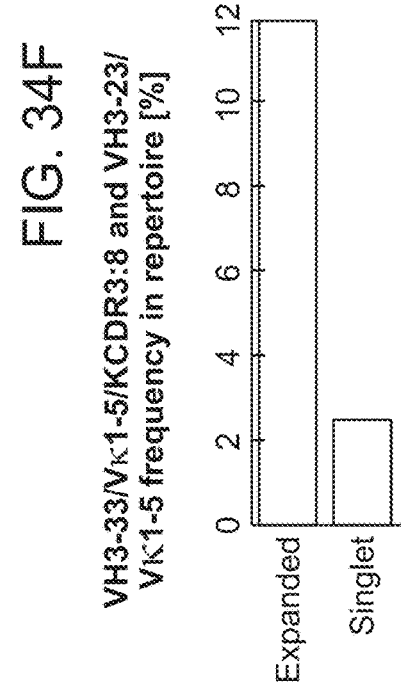
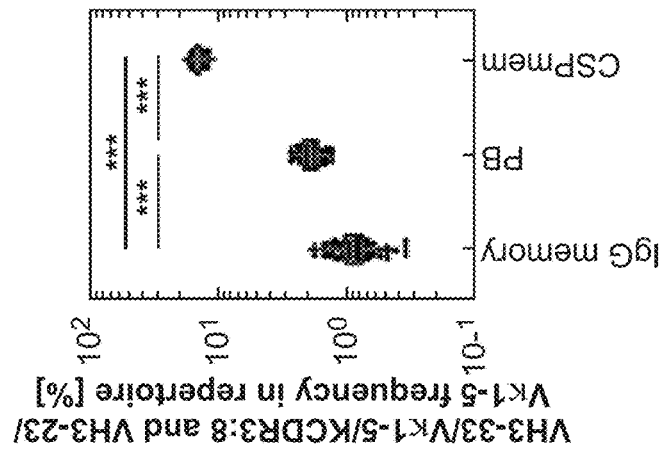
FIG. 34D
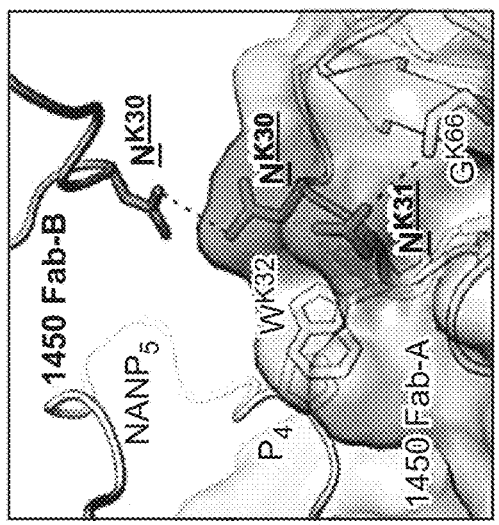
FIG. 34E
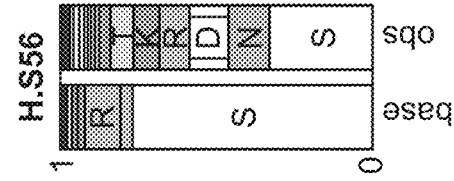
FIG. 34F
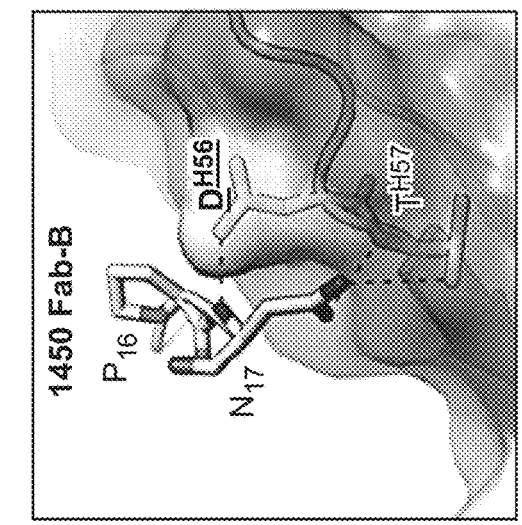
FIG. 34G

```
SEQUENCE LISTING

<160> NUMBER OF SEQ ID NOS: 40

<210> SEQ ID NO 1
<211> LENGTH: 22
<212> TYPE: PRT
<213> ORGANISM: Artificial Sequence
<220> FEATURE:
<223> OTHER INFORMATION: Antigen

<400> SEQUENCE: 1

Asn Pro Asn Ala Asn Pro Asn Ala Asn Pro Asn Ala Asn Pro Asn Ala
1               5                   10                  15

Asn Pro Asn Ala Asn Pro
            20

<210> SEQ ID NO 2
<211> LENGTH: 122
<212> TYPE: PRT
<213> ORGANISM: Artificial Sequence
<220> FEATURE:
<223> OTHER INFORMATION: Antibody
```

```
<400> SEQUENCE: 2

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Trp Asp Gly Ser Lys Lys Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Val Arg Asp Ser Ser Asp Tyr Tyr Gly Asp Ala Phe Asp Ile Trp
            100                 105                 110

Gly Gln Gly Thr Met Val Thr Val Ser Ser
        115                 120

<210> SEQ ID NO 3
<211> LENGTH: 19
<212> TYPE: PRT
<213> ORGANISM: Artificial Sequence
<220> FEATURE:
<223> OTHER INFORMATION: Epitope

<400> SEQUENCE: 3

Lys Gln Pro Ala Asp Gly Asn Pro Asp Pro Asn Ala Asn Pro Asn Val
1               5                   10                  15

Asp Pro Asn

<210> SEQ ID NO 4
<211> LENGTH: 8
<212> TYPE: PRT
<213> ORGANISM: Artificial Sequence
<220> FEATURE:
<223> OTHER INFORMATION: Flag Tag

<400> SEQUENCE: 4

Asp Tyr Lys Asp Asp Asp Asp Lys
1               5

<210> SEQ ID NO 5
<211> LENGTH: 710
<212> TYPE: PRT
<213> ORGANISM: Artificial Sequence
<220> FEATURE:
<223> OTHER INFORMATION: Antibody

<400> SEQUENCE: 5

Tyr Glu Leu Thr Gln Glu Thr Gly Val Ser Val Ala Leu Gly Arg Thr
1               5                   10                  15

Val Thr Ile Thr Cys Arg Gly Asp Ser Leu Arg Ser His Tyr Ala Ser
            20                  25                  30

Trp Tyr Gln Lys Lys Pro Gly Gln Ala Pro Ile Leu Leu Phe Tyr Gly
        35                  40                  45

Lys Asn Asn Arg Pro Ser Gly Val Pro Asp Arg Phe Ser Gly Ser Ala
    50                  55                  60

Ser Gly Asn Arg Ala Ser Leu Thr Ile Ser Gly Ala Gln Ala Glu Asp
65                  70                  75                  80
```

-continued

Asp Ala Glu Tyr Tyr Cys Ser Ser Arg Asp Lys Ser Gly Ser Arg Leu
                85                  90                  95

Ser Val Phe Gly Gly Gly Thr Lys Leu Thr Val Leu Ser Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Gly Gly Ser Gly Ser Gly Ser Gly Ser Gly Thr
    210                 215                 220

Gly Glu Asn Leu Tyr Phe Gln Gly Ser Ala Gly Thr Thr Gly Thr Ser
225                 230                 235                 240

Ala Ser Thr Ser Gly Tyr Pro Tyr Asp Val Pro Asp Tyr Ala Gly Gly
                245                 250                 255

Gly Gly Ser Ala Gly Gly Thr Ala Thr Leu Glu Val Leu Phe Gln Gly
            260                 265                 270

Pro Ser Ser Gly Ser Ser Ser Gly Gly Thr Gly Glu Val Gln Leu
        275                 280                 285

Val Glu Ser Gly Gly Gly Leu Val Lys Pro Gly Gly Ser Leu Arg Leu
    290                 295                 300

Ser Cys Ser Ala Ser Gly Phe Asp Phe Asp Asn Ala Trp Met Thr Trp
305                 310                 315                 320

Val Arg Gln Pro Pro Gly Lys Gly Leu Glu Trp Val Gly Arg Ile Thr
                325                 330                 335

Gly Pro Gly Glu Gly Trp Ser Val Asp Tyr Ala Ala Pro Val Glu Gly
            340                 345                 350

Arg Phe Thr Ile Ser Arg Leu Asn Ser Ile Asn Phe Leu Tyr Leu Glu
        355                 360                 365

Met Asn Asn Leu Arg Met Glu Asp Ser Gly Leu Tyr Phe Cys Ala Arg
    370                 375                 380

Thr Gly Lys Tyr Tyr Asp Phe Trp Ser Gly Tyr Pro Pro Gly Glu Glu
385                 390                 395                 400

Tyr Phe Gln Asp Trp Gly Arg Gly Thr Leu Val Thr Val Ser Ser Ala
                405                 410                 415

Ser Thr Lys Gly Pro Ser Val Phe Pro Leu Ala Pro Ser Ser Lys Ser
            420                 425                 430

Thr Ser Gly Gly Thr Ala Ala Leu Gly Cys Leu Val Lys Asp Tyr Phe
        435                 440                 445

Pro Glu Pro Val Thr Val Ser Trp Asn Ser Gly Ala Leu Thr Ser Gly
    450                 455                 460

Val His Thr Phe Pro Ala Val Leu Gln Ser Ser Gly Leu Tyr Ser Leu
465                 470                 475                 480

Ser Ser Val Val Thr Val Pro Ser Ser Ser Leu Gly Thr Gln Thr Tyr
                485                 490                 495

Ile Cys Asn Val Asn His Lys Pro Ser Asn Thr Lys Val Asp Lys Arg

```
            500                 505                 510
Val Glu Pro Lys Ser Cys Ser Arg Gly Gly Gly Gly Ser Gly Gly
        515                 520                 525

Ser Gly Gly Ser Gly Gly Ser Met Ser Ser Gln Ile Arg Gln Asn Tyr
        530                 535                 540

Ser Thr Asp Val Glu Ala Val Asn Ser Leu Val Asn Leu Tyr Leu
545                 550                 555                 560

Gln Ala Ser Tyr Thr Tyr Leu Ser Leu Gly Phe Tyr Phe Asp Arg Asp
                        565                 570                 575

Asp Val Ala Leu Glu Gly Val Ser His Phe Phe Arg Glu Leu Ala Glu
                580                 585                 590

Glu Lys Arg Glu Gly Tyr Glu Arg Leu Leu Lys Met Gln Asn Gln Arg
            595                 600                 605

Gly Gly Arg Ala Leu Phe Gln Asp Ile Lys Lys Pro Ala Glu Asp Glu
        610                 615                 620

Trp Gly Lys Thr Pro Asp Ala Met Lys Ala Ala Met Ala Leu Glu Lys
625                 630                 635                 640

Lys Leu Asn Gln Ala Leu Leu Asp Leu His Ala Leu Gly Ser Ala Arg
                        645                 650                 655

Thr Asp Pro His Leu Cys Asp Phe Leu Glu Thr His Phe Leu Asp Glu
                660                 665                 670

Glu Val Lys Leu Ile Lys Lys Met Gly Asp His Leu Thr Asn Leu His
            675                 680                 685

Arg Leu Gly Gly Pro Glu Ala Gly Leu Gly Glu Tyr Leu Phe Glu Arg
        690                 695                 700

Leu Thr Leu Arg His Asp
705                 710

<210> SEQ ID NO 6
<211> LENGTH: 718
<212> TYPE: PRT
<213> ORGANISM: Artificial Sequence
<220> FEATURE:
<223> OTHER INFORMATION: Nanoparticle

<400> SEQUENCE: 6

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                        85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Ser Arg Glu Glu Met Thr Lys Asn Gln Val Ser
        130                 135                 140

Leu Thr Cys Leu Val Lys Gly Phe Tyr Pro Ser Asp Ile Ala Val Glu
```

```
                145                 150                 155                 160
Trp Glu Ser Asn Gly Gln Pro Glu Asn Tyr Lys Thr Thr Pro Pro
                    165                 170                 175

Val Leu Asp Ser Asp Gly Ser Phe Phe Leu Tyr Ser Lys Leu Thr Val
                    180                 185                 190

Asp Lys Ser Arg Trp Gln Gln Gly Asn Val Phe Ser Cys Ser Val Met
                    195                 200                 205

His Glu Ala Leu His Asn His Tyr Thr Gln Lys Ser Leu Ser Leu Ser
                210                 215                 220

Pro Gly Lys Gly Gly Ser Ser Gly Ser Gly Ser Thr Gly Thr
225                 230                 235                 240

Ser Ser Ser Gly Thr Gly Thr Ser Ala Gly Thr Thr Gly Thr Ser Ala
                    245                 250                 255

Ser Thr Ser Gly Ser Gly Ser Gly Gly Gly Gly Ser Gly Gly Gly
                260                 265                 270

Gly Ser Ala Gly Gly Thr Ala Thr Ala Gly Ala Ser Ser Gly Ser Gly
                275                 280                 285

Ser Ser Gly Ser Ser Ser Gly Gly Thr Gly Asp Lys Thr His Thr
                290                 295                 300

Cys Pro Pro Cys Pro Ala Pro Glu Leu Leu Gly Gly Pro Ser Val Phe
305                 310                 315                 320

Leu Phe Pro Pro Lys Pro Lys Asp Thr Leu Met Ile Ser Arg Thr Pro
                    325                 330                 335

Glu Val Thr Cys Val Val Val Asp Val Ser His Glu Asp Pro Glu Val
                    340                 345                 350

Lys Phe Asn Trp Tyr Val Asp Gly Val Glu Val His Asn Ala Lys Thr
                    355                 360                 365

Lys Pro Arg Glu Glu Gln Tyr Asn Ser Thr Tyr Arg Val Val Ser Val
                370                 375                 380

Leu Thr Val Leu His Gln Asp Trp Leu Asn Gly Lys Glu Tyr Lys Cys
385                 390                 395                 400

Lys Val Ser Asn Lys Ala Leu Pro Ala Pro Ile Glu Lys Thr Ile Ser
                    405                 410                 415

Lys Ala Lys Gly Gln Pro Arg Glu Pro Gln Val Tyr Thr Leu Pro Pro
                    420                 425                 430

Ser Arg Glu Glu Met Thr Lys Asn Gln Val Ser Leu Thr Cys Leu Val
                    435                 440                 445

Lys Gly Phe Tyr Pro Ser Asp Ile Ala Val Glu Trp Glu Ser Asn Gly
                    450                 455                 460

Gln Pro Glu Asn Asn Tyr Lys Thr Thr Pro Pro Val Leu Asp Ser Asp
465                 470                 475                 480

Gly Ser Phe Phe Leu Tyr Ser Lys Leu Thr Val Asp Lys Ser Arg Trp
                    485                 490                 495

Gln Gln Gly Asn Val Phe Ser Cys Ser Val Met His Glu Ala Leu His
                500                 505                 510

Asn His Tyr Thr Gln Lys Ser Leu Ser Leu Ser Pro Gly Lys Ser Arg
                515                 520                 525

Gly Gly Gly Gly Ser Gly Gly Ser Gly Gly Ser Gly Gly Ser Met
                530                 535                 540

Ser Ser Gln Ile Arg Gln Asn Tyr Ser Thr Asp Val Glu Ala Ala Val
545                 550                 555                 560

Asn Ser Leu Val Asn Leu Tyr Leu Gln Ala Ser Tyr Thr Tyr Leu Ser
                565                 570                 575
```

```
Leu Gly Phe Tyr Phe Asp Arg Asp Asp Val Ala Leu Glu Gly Val Ser
            580                 585                 590

His Phe Phe Arg Glu Leu Ala Glu Glu Lys Arg Glu Gly Tyr Glu Arg
        595                 600                 605

Leu Leu Lys Met Gln Asn Gln Arg Gly Gly Arg Ala Leu Phe Gln Asp
    610                 615                 620

Ile Lys Lys Pro Ala Glu Asp Glu Trp Gly Lys Thr Pro Asp Ala Met
625                 630                 635                 640

Lys Ala Ala Met Ala Leu Glu Lys Lys Leu Asn Gln Ala Leu Leu Asp
                645                 650                 655

Leu His Ala Leu Gly Ser Ala Arg Thr Asp Pro His Leu Cys Asp Phe
            660                 665                 670

Leu Glu Thr His Phe Leu Asp Glu Glu Val Lys Leu Ile Lys Lys Met
        675                 680                 685

Gly Asp His Leu Thr Asn Leu His Arg Leu Gly Gly Pro Glu Ala Gly
    690                 695                 700

Leu Gly Glu Tyr Leu Phe Glu Arg Leu Thr Leu Arg His Asp
705                 710                 715

<210> SEQ ID NO 7
<211> LENGTH: 18
<212> TYPE: PRT
<213> ORGANISM: Artificial Sequence
<220> FEATURE:
<223> OTHER INFORMATION: Antibody

<400> SEQUENCE: 7

Ala Arg Val Gln Asp Ser Glu Asp Tyr Gly Gly Asn Ser Gly Ala Phe
1               5                   10                  15

Asp Ile

<210> SEQ ID NO 8
<211> LENGTH: 16
<212> TYPE: PRT
<213> ORGANISM: Artificial Sequence
<220> FEATURE:
<223> OTHER INFORMATION: Antibody

<400> SEQUENCE: 8

Ala Arg Val Arg Asp Ser Ser Asp Tyr Tyr Gly Asp Ala Phe Asp Ile
1               5                   10                  15

<210> SEQ ID NO 9
<211> LENGTH: 17
<212> TYPE: PRT
<213> ORGANISM: Artificial Sequence
<220> FEATURE:
<223> OTHER INFORMATION: Antibody

<400> SEQUENCE: 9

Ala Arg Val Gln Thr Thr Thr Gly Gly Gly Ser Cys Cys Pro Phe Asp
1               5                   10                  15

Tyr

<210> SEQ ID NO 10
<211> LENGTH: 18
<212> TYPE: PRT
<213> ORGANISM: Artificial Sequence
<220> FEATURE:
<223> OTHER INFORMATION: Antibody
```

```
<400> SEQUENCE: 10

Ala Arg Val Gln Asp Ser Glu Asp Tyr Gly Gly Asn Ser Gly Val Phe
1               5                   10                  15

Asp Ile

<210> SEQ ID NO 11
<211> LENGTH: 17
<212> TYPE: PRT
<213> ORGANISM: Artificial Sequence
<220> FEATURE:
<223> OTHER INFORMATION: Antibody

<400> SEQUENCE: 11

Ala Lys Val Gly Glu Gly Gln Val Gly Asp Ser Ser Gly Tyr Tyr Asp
1               5                   10                  15

His

<210> SEQ ID NO 12
<211> LENGTH: 60
<212> TYPE: PRT
<213> ORGANISM: Artificial Sequence
<220> FEATURE:
<223> OTHER INFORMATION: Antibody

<400> SEQUENCE: 12

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr
        50                  55                  60

<210> SEQ ID NO 13
<211> LENGTH: 60
<212> TYPE: PRT
<213> ORGANISM: Artificial Sequence
<220> FEATURE:
<223> OTHER INFORMATION: Antibody

<400> SEQUENCE: 13

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr
        50                  55                  60

<210> SEQ ID NO 14
<211> LENGTH: 60
<212> TYPE: PRT
<213> ORGANISM: Artificial Sequence
<220> FEATURE:
<223> OTHER INFORMATION: Antibody

<400> SEQUENCE: 14

Gln Val Gln Leu Val Glu Ser Gly Gly Gly Val Val Gln Pro Gly Arg
1               5                   10                  15
```

```
Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr
    50                  55                  60

<210> SEQ ID NO 15
<211> LENGTH: 60
<212> TYPE: PRT
<213> ORGANISM: Artificial Sequence
<220> FEATURE:
<223> OTHER INFORMATION: Antibody

<400> SEQUENCE: 15

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr
    50                  55                  60

<210> SEQ ID NO 16
<211> LENGTH: 60
<212> TYPE: PRT
<213> ORGANISM: Artificial Sequence
<220> FEATURE:
<223> OTHER INFORMATION: Antibody

<400> SEQUENCE: 16

Gln Val Gln Leu Val Asp Ser Gly Gly Gly Val Val Gln Pro Gly Arg
1               5                   10                  15

Ser Leu Arg Leu Ser Cys Ala Ala Ser Ala Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr
    50                  55                  60

<210> SEQ ID NO 17
<211> LENGTH: 38
<212> TYPE: PRT
<213> ORGANISM: Artificial Sequence
<220> FEATURE:
<223> OTHER INFORMATION: Antibody

<400> SEQUENCE: 17

Ala Asp Ser Val Lys Gly Arg Phe Thr Ile Ser Arg Asp Asn Ser Lys
1               5                   10                  15

Asn Thr Leu Tyr Leu Gln Met Asn Ser Leu Arg Ala Glu Asp Thr Ala
            20                  25                  30

Val Tyr Tyr Cys Ala Arg
        35

<210> SEQ ID NO 18
<211> LENGTH: 38
<212> TYPE: PRT
<213> ORGANISM: Artificial Sequence
<220> FEATURE:
<223> OTHER INFORMATION: Antibody
```

<400> SEQUENCE: 18

Ala Asp Ser Ala Lys Gly Arg Phe Thr Ile Ser Arg Asp Asn Ser Thr
1               5                   10                  15

Asn Thr Leu Phe Leu Gln Met Asn Ser Leu Arg Ala Glu Asp Thr Ala
            20                  25                  30

Val Tyr Tyr Cys Ala Arg
            35

<210> SEQ ID NO 19
<211> LENGTH: 38
<212> TYPE: PRT
<213> ORGANISM: Artificial Sequence
<220> FEATURE:
<223> OTHER INFORMATION: Antibody

<400> SEQUENCE: 19

Ala Asp Ser Val Lys Gly Arg Phe Thr Ile Ser Arg Asp Asn Ser Lys
1               5                   10                  15

Asn Thr Leu Tyr Leu Gln Met Asn Ser Leu Arg Ala Glu Asp Thr Ala
            20                  25                  30

Val Tyr Tyr Cys Ala Lys
            35

<210> SEQ ID NO 20
<211> LENGTH: 38
<212> TYPE: PRT
<213> ORGANISM: Artificial Sequence
<220> FEATURE:
<223> OTHER INFORMATION: Antibody

<400> SEQUENCE: 20

Ala Asp Ser Val Lys Gly Arg Phe Thr Ile Ser Arg Asp Asn Ser Lys
1               5                   10                  15

Asn Thr Leu Tyr Leu Gln Met Asn Ser Leu Arg Ala Glu Gly Thr Ala
            20                  25                  30

Val Tyr Tyr Cys Ala Arg
            35

<210> SEQ ID NO 21
<211> LENGTH: 38
<212> TYPE: PRT
<213> ORGANISM: Artificial Sequence
<220> FEATURE:
<223> OTHER INFORMATION: Antibody

<400> SEQUENCE: 21

Ala Asp Ser Val Lys Gly Arg Phe Ala Ile Ser Arg Asp Asn Ser Lys
1               5                   10                  15

Asn Thr Leu Tyr Leu Gln Met Asn Ser Leu Arg Ala Glu Asp Thr Ala
            20                  25                  30

Val Tyr Tyr Cys Ala Arg
            35

<210> SEQ ID NO 22
<211> LENGTH: 38
<212> TYPE: PRT
<213> ORGANISM: Artificial Sequence
<220> FEATURE:
<223> OTHER INFORMATION: Antibody

<400> SEQUENCE: 22

-continued

```
Thr Asp Ser Val Lys Gly Arg Phe Thr Ile Ser Arg Asp Asn Ser Lys
1               5                   10                  15

Asn Thr Leu Tyr Leu Gln Met Asn Ser Leu Arg Ala Glu Asp Thr Ala
                20                  25                  30

Val Tyr Tyr Cys Ala Arg
            35

<210> SEQ ID NO 23
<211> LENGTH: 38
<212> TYPE: PRT
<213> ORGANISM: Artificial Sequence
<220> FEATURE:
<223> OTHER INFORMATION: Antibody

<400> SEQUENCE: 23

Ala Asp Ser Val Lys Gly Arg Phe Thr Ile Ser Arg Asp Asn Ser Lys
1               5                   10                  15

Asn Arg Leu Tyr Leu Gln Met Asn Ser Leu Arg Ala Glu Asp Thr Ala
                20                  25                  30

Val Tyr Tyr Cys Ala Arg
            35

<210> SEQ ID NO 24
<211> LENGTH: 38
<212> TYPE: PRT
<213> ORGANISM: Artificial Sequence
<220> FEATURE:
<223> OTHER INFORMATION: Antibody

<400> SEQUENCE: 24

Ala Asp Ser Val Lys Gly Arg Phe Thr Ile Ser Arg Asp Asn Ser Lys
1               5                   10                  15

Asn Thr Leu Tyr Leu Gln Met Ser Ser Leu Arg Ala Glu Asp Thr Ala
                20                  25                  30

Val Tyr Tyr Cys Ala Arg
            35

<210> SEQ ID NO 25
<211> LENGTH: 123
<212> TYPE: PRT
<213> ORGANISM: Artificial Sequence
<220> FEATURE:
<223> OTHER INFORMATION: Antibody

<400> SEQUENCE: 25

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Arg Asp Ser Ser Asp Tyr Tyr Gly Asp Ala Phe Asp Ile
                100                 105                 110

Trp Gly Gln Gly Thr Met Val Thr Val Ser Ser
```

<210> SEQ ID NO 26
<211> LENGTH: 123
<212> TYPE: PRT
<213> ORGANISM: Artificial Sequence
<220> FEATURE:
<223> OTHER INFORMATION: Antibody

<400> SEQUENCE: 26

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Arg Asp Ser Ser Asp Tyr Tyr Gly Asp Ala Phe Asp Ile
            100                 105                 110

Trp Gly Gln Gly Thr Met Val Thr Val Ser Ser
        115                 120

<210> SEQ ID NO 27
<211> LENGTH: 123
<212> TYPE: PRT
<213> ORGANISM: Artificial Sequence
<220> FEATURE:
<223> OTHER INFORMATION: Antibody

<400> SEQUENCE: 27

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Ile Ile Trp Tyr Asp Gly Ser Lys Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Arg Asp Ser Ser Asp Tyr Tyr Gly Asp Ala Phe Asp Ile
            100                 105                 110

Trp Gly Gln Gly Thr Met Val Thr Val Ser Ser
        115                 120

<210> SEQ ID NO 28
<211> LENGTH: 123
<212> TYPE: PRT
<213> ORGANISM: Artificial Sequence
<220> FEATURE:
<223> OTHER INFORMATION: Antibody

<400> SEQUENCE: 28

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Lys Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Arg Asp Ser Ser Asp Tyr Tyr Gly Asp Ala Phe Asp Ile
                100                 105                 110

Trp Gly Gln Gly Thr Met Val Thr Val Ser Ser
            115                 120

<210> SEQ ID NO 29
<211> LENGTH: 123
<212> TYPE: PRT
<213> ORGANISM: Artificial Sequence
<220> FEATURE:
<223> OTHER INFORMATION: Antibody

<400> SEQUENCE: 29

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Arg Asp Ser Ser Asp Tyr Tyr Gly Asp Ala Phe Asp Ile
                100                 105                 110

Trp Gly Gln Gly Thr Met Val Thr Val Ser Ser
            115                 120

<210> SEQ ID NO 30
<211> LENGTH: 123
<212> TYPE: PRT
<213> ORGANISM: Artificial Sequence
<220> FEATURE:
<223> OTHER INFORMATION: Antibody

<400> SEQUENCE: 30

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Lys Lys Tyr Tyr Ala Asp Ser Val

```
                50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val Arg Asp Ser Ser Tyr Tyr Tyr Gly Asp Ala Phe Asp Ile
            100                 105                 110

Trp Gly Gln Gly Thr Met Val Thr Val Ser Ser
            115                 120

<210> SEQ ID NO 31
<211> LENGTH: 106
<212> TYPE: PRT
<213> ORGANISM: Artificial Sequence
<220> FEATURE:
<223> OTHER INFORMATION: Antibody

<400> SEQUENCE: 31

Asp Ile Gln Met Thr Gln Ser Pro Ser Thr Leu Ser Ala Ser Val Gly
  1               5                  10                  15

Asp Arg Val Thr Ile Thr Cys Arg Ala Ser Gln Ser Ile Ser Ser Trp
             20                  25                  30

Leu Ala Trp Tyr Gln Gln Lys Pro Gly Lys Ala Pro Lys Leu Leu Ile
         35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Tyr Trp Thr
                 85                  90                  95

Phe Gly Gln Gly Thr Lys Val Glu Ile Lys
            100                 105

<210> SEQ ID NO 32
<211> LENGTH: 106
<212> TYPE: PRT
<213> ORGANISM: Artificial Sequence
<220> FEATURE:
<223> OTHER INFORMATION: Antibody

<400> SEQUENCE: 32

Asp Ile Gln Met Thr Gln Ser Pro Ser Thr Leu Ser Ala Ser Val Gly
  1               5                  10                  15

Asp Arg Val Thr Ile Thr Cys Arg Ala Ser Gln Ser Ile Ser Ser Trp
             20                  25                  30

Leu Ala Trp Tyr Gln Gln Lys Pro Gly Lys Ala Pro Lys Leu Leu Ile
         35                  40                  45

Tyr Lys Ala Ser Asn Leu Glu Ser Gly Val Pro Leu Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Asn Tyr Trp Thr
                 85                  90                  95

Phe Gly Gln Gly Thr Lys Val Glu Ile Lys
            100                 105

<210> SEQ ID NO 33
<211> LENGTH: 106
```

```
<212> TYPE: PRT
<213> ORGANISM: Artificial Sequence
<220> FEATURE:
<223> OTHER INFORMATION: Antibody

<400> SEQUENCE: 33

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Asn Leu Glu Ser Gly Val Pro Leu Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Trp Thr
                85                  90                  95

Phe Gly Gln Gly Thr Lys Val Glu Ile Lys
            100                 105

<210> SEQ ID NO 34
<211> LENGTH: 106
<212> TYPE: PRT
<213> ORGANISM: Artificial Sequence
<220> FEATURE:
<223> OTHER INFORMATION: Antibody

<400> SEQUENCE: 34

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Asn Leu Glu Ser Gly Val Pro Leu Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Tyr Asn Tyr Trp Thr
                85                  90                  95

Phe Gly Gln Gly Thr Lys Val Glu Ile Lys
            100                 105

<210> SEQ ID NO 35
<211> LENGTH: 124
<212> TYPE: PRT
<213> ORGANISM: Artificial Sequence
<220> FEATURE:
<223> OTHER INFORMATION: Antibody

<400> SEQUENCE: 35

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
```

```
                    50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val Gln Thr Thr Thr Gly Gly Gly Ser Cys Cys Pro Phe Asp
                100                 105                 110

Tyr Trp Gly Gln Gly Thr Leu Val Thr Val Ser Ser
            115                 120
```

<210> SEQ ID NO 36
<211> LENGTH: 124
<212> TYPE: PRT
<213> ORGANISM: Artificial Sequence
<220> FEATURE:
<223> OTHER INFORMATION: Antibody

<400> SEQUENCE: 36

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Ile Ile Trp Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val Gln Thr Thr Thr Gly Gly Gly Ser Cys Cys Pro Phe Asp
                100                 105                 110

Tyr Trp Gly Gln Gly Thr Leu Val Thr Val Ser Ser
            115                 120
```

<210> SEQ ID NO 37
<211> LENGTH: 124
<212> TYPE: PRT
<213> ORGANISM: Artificial Sequence
<220> FEATURE:
<223> OTHER INFORMATION: Antibody

<400> SEQUENCE: 37

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Asn Tyr
                 20                  25                  30

Gly Met His Trp Val Arg Gln Ala Pro Gly Lys Gly Leu Glu Trp Val
             35                  40                  45

Ala Val Ile Trp Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val Gln Thr Thr Thr Gly Gly Gly Ser Cys Cys Pro Phe Asp
                100                 105                 110
```

```
Tyr Trp Gly Gln Gly Thr Leu Val Thr Val Ser Ser
            115                 120

<210> SEQ ID NO 38
<211> LENGTH: 124
<212> TYPE: PRT
<213> ORGANISM: Artificial Sequence
<220> FEATURE:
<223> OTHER INFORMATION: Antibody

<400> SEQUENCE: 38

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Lys Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Gln Thr Thr Thr Gly Gly Gly Ser Cys Cys Pro Phe Asp
            100                 105                 110

Tyr Trp Gly Gln Gly Thr Leu Val Thr Val Ser Ser
            115                 120

<210> SEQ ID NO 39
<211> LENGTH: 106
<212> TYPE: PRT
<213> ORGANISM: Artificial Sequence
<220> FEATURE:
<223> OTHER INFORMATION: Antibody

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Trp Thr
                85                  90                  95

Phe Gly Gln Gly Thr Lys Val Glu Ile Lys
            100                 105

<210> SEQ ID NO 40
<211> LENGTH: 106
<212> TYPE: PRT
<213> ORGANISM: Artificial Sequence
<220> FEATURE:
<223> OTHER INFORMATION: Antibody

<400> SEQUENCE: 40

Asp Ile Gln Met Thr Gln Ser Pro Ser Ser Leu Ser Ala Ser Val Gly
```

-continued

```
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Asn Tyr Trp Thr
                85                  90                  95

Phe Gly Gln Gly Thr Lys Val Glu Ile Lys
                100                 105
```

NANOPARTICLE PLATFORM FOR ANTIBODY AND VACCINE DELIVERY

STATEMENT REGARDING ELECTRONIC FILING OF A SEQUENCE LISTING

A Sequence Listing in ASCII text format, submitted under 37 C.F.R. § 1.821, entitled 1360-25_ST25.txt, 22,990 bytes in size, generated on Jun. 9, 2022, and filed via EFS-Web, is provided in lieu of a paper copy. This Sequence Listing is incorporated by reference into the application for its disclosures.

FIELD

The present invention relates to nanoparticles. In particular, the present invention relates to nanoparticle subunit fusion proteins, vaccines comprising the nanoparticles, and related compositions and methods.

BACKGROUND

Nanoparticles have contributed to advancements in various disciplines. Their use has the potential to confer targeted delivery; and allows the engineering of ordered microarrays, slow release and caged micro-environments for catalytic processes.

Nanoparticles can be synthesized from a variety of materials, including polysaccharide, liposomes, or inorganic nanomaterial. However, these delivery platforms are associated with important limitations when fusing biomolecules, such as reduced activity of proteins due to harsh fabrication conditions, unwanted degradation products and low encapsulation efficiency. Inappropriate conditions or formulations can have catastrophic effects on structure, and thus inhibit desired function. For example, the trimeric gp120 glycoprotein—the most-heavily glycosylated known—and antibody domains have strict buffer ranges to be optimally active.

Protein nanoparticles are an attractive alternative to the technologies above; their building blocks are amino acids and genetic engineering enables exquisite control of composition, molecular weight, and function. For the fabrication of nanoparticles that contain sensitive and metastable proteins, protein self-assembly is the method of choice. Indeed, self-assembled nanoparticles form under physiological conditions through non-covalent interactions and reliably yield uniform and often symmetric nanocapsules. Self-assembling protein nanoparticles possess three distinct surfaces that can all be tweaked to convey added functionalities: exterior, interior and inter-subunits surfaces.

Numerous reports exist for the fusion of peptides to self-assembling proteins. Titanium or gold binding peptides can be used to selectively adhere nanoparticles to these metals. However, biological interactions often require ternary and quaternary structure, and thus folded proteins generally confer extended functions over peptides. Moreover, 50% of human proteins are estimated to be glycosylated, and these posttranslational modifications play a key role in upholding the protein structure, convey stability, and provide function. Only a few examples exist for the genetic fusion of glycoproteins to protein nanoparticles.

Nanocages decorated on their surface with antigens for use in vaccines have been described by, e.g., U.S. Pat. No. 8,546,337, U.S. Patent Application Publication No. 2015/0110825, International Patent Application Publication No. 2016/109792, Kanekiyo et al. (*Nature*, 2013, 499:102-106), and Sliepen et al. (*Retrovirology*, 2015, 12:82). We have previously shown that it is possible to genetically fuse cargo to the exterior of the self-assembling lumazine synthase protein for its multimeric (60meric) display (Jardine et al., Science. 2013 May 10; 340 (6133): 711-6).

International Patent Application Publication No. 2010/0222501 describe a method for making composite nanoparticles, in which a moiety such as an antibody can be attached to organic groups protruding from the surface of the nanoparticles.

Choe et al. (*Materials* 2016, 9 (12): 994) provide a review of several methods to isolate and target antibodies using smart biomaterials that mimic the binding of Fc-receptors to antibodies. Fc-binding peptides are applied e.g., to localize antibodies on nanomaterials and to increase the half-life of proteins in serum. In this review, recent developments of Fc-binding peptides are presented and their binding characteristics and diverse applications are discussed.

Khoshnejad et al. (*Bioconjugate Chem.*, 2016, 27 (3): 628-637) describe a study in which monoclonal antibodies to ICAM-1 and PECAM-1 or their single chain antigen-binding fragments (scFv) were conjugated to ferritin nanoparticles. It is suggested that ferritin nanoparticles may provide a platform for targeting endothelial adhesion molecules with carriers in the 20 nm size range.

Kang et al. (Fourth International Conference on Multifunctional, Hybrid and Nanomaterials, Poster programme, 2015, P1.048) describe a chimeric protein nanocage of a scFv variant of Trastuzumab and human ferritin.

Carter et al. (Science., 1992, 256 (5053): 105-7) show that engaging CD19 at the same time as an antigen produces a heightened B cell response to that antigen.

A need exists for the development of a product, composition and/or method that provides the public with a useful alternative.

SUMMARY OF THE INVENTION

In accordance with an aspect, there is provided a fusion protein comprising:
- a nanocage monomer; and
- an antibody or fragment thereof linked to the nanocage monomer, the antibody or fragment thereof comprising a first member of a binding pair;
- wherein a plurality of the fusion proteins self-assemble to form a nanocage in which a plurality of the antibodies or fragments thereof decorate the exterior surface of the nanocage, whereby the first member of the binding pair is exposed for interacting with a second member of the binding pair.

In an aspect, the first member of the binding pair is a Fc portion of an antibody or fragment thereof and the second member of the binding pair is a Fc receptor.

In an aspect, the first member of the binding pair is an antigen-binding epitope and the second member of the binding pair is an antigen.

In an aspect, the nanocage comprises from about 3 to about 100 nanocage monomers, such as 24 or 60 monomers.

In an aspect, the nanocage monomer is selected from ferritin, encapsulin, SOR, lumazine synthase, pyruvate dehydrogenase, carboxysome, vault proteins, GroEL, heat shock protein, E2P, MS2 coat protein, fragments thereof, and variants thereof.

In an aspect, the fusion protein further comprises a linker between the nanocage monomer and the antibody or fragment thereof.

In an aspect, the linker is flexible or rigid and comprises from about 1 to about 30 amino acid residues.

In an aspect, the linker comprises from about 8 to about 16 amino acid residues.

In an aspect, the linker comprises a GGS repeat.

In an aspect, the linker comprises four GGS repeats.

In an aspect, the fusion protein further comprises the antigen.

In an aspect, the antigen comprises a repeat domain.

In an aspect, the antigen is a malaria antigen.

In an aspect, the antigen is a fragment of the malaria CSP protein.

In an aspect, the antigen is a fragment of the NANP repeat domain of the malaria CSP protein.

In an aspect, the antigen comprises 5.5 NANP repeats.

In an aspect, the antigen is NPNANPNANPNANPNANPNANP (SEQ ID NO: 1).

In an aspect, the fusion protein is a Fc domain.

In an aspect, the antibody or fragment thereof is specific for a repeat domain.

In an aspect, the antibody or fragment thereof is specific for a malaria antigen.

In an aspect, the antibody or fragment thereof is specific for the malaria CSP protein.

In an aspect, the antibody or fragment thereof is specific for the NANP repeat domain of the malaria CSP protein.

In an aspect, the antibody or fragment thereof comprises a sequence having at least 90% sequence identity to the sequence:

QVQLVESGGGVVQPGRSLRLSCAASGFTFSNYGMHWVRQAPGKGLEWVAV

IWDGSKKYYADSVKGRFTISRDNSKNTLYLQMNSLRAEDTAVYYCARVRD

SSDYYGDAFDIWGQGTMVTVSS.

or a fragment thereof.

In an aspect, the antibody or fragment thereof comprises the sequence:

QVQLVESGGGVVQPGRSLRLSCAASGFTFSNYGMHWVRQAPGKGLEWVAV

IWDGSKKYYADSVKGRFTISRDNSKNTLYLQMNSLRAEDTAVYYCARVRD

SSDYYGDAFDIWGQGTMVTVSS.

In an aspect, the antibody or fragment thereof consists of the sequence:

QVQLVESGGGVVQPGRSLRLSCAASGFTFSNYGMHWVRQAPGKGLEWVAV

IWDGSKKYYADSVKGRFTISRDNSKNTLYLQMNSLRAEDTAVYYCARVRD

SSDYYGDAFDIWGQGTMVTVSS

In an aspect, the antibody or fragment thereof is specific for a tumour antigen.

In an aspect, the antibody or fragment thereof is specific for an autoantigen.

In an aspect, the antibody or fragment thereof is specific for CD19, CD22, CD79, BCMA, or CD20.

In an aspect, the antibody or fragment thereof is specific for a target organ.

In an aspect, the antibody or fragment thereof comprises a heavy chain and/or light chain of a Fab fragment.

In an aspect, the antibody or fragment thereof comprises a scFv.

In an aspect, the fusion protein further comprises a Fab light chain and/or heavy chain.

In an aspect, the fusion protein is in association with a separately produced Fab light chain and/or heavy chain.

In an aspect, the fusion protein further comprises a detectable moiety.

In an aspect, the detectable moiety is a fluorescent protein, such as GFP, EGFP, Ametrine, and/or a flavin-based fluorescent protein, such as a LOV-protein, such as iLOV.

In accordance with an aspect, there is provided a nanocage comprising at least one fusion protein described herein.

In an aspect, each nanocage monomer comprises the fusion protein described herein.

In an aspect, from about 20% to about 80% of the nanocage monomers comprise the fusion protein described herein.

In an aspect, the nanocage is multivalent.

In an aspect, the nanocage is carrying a cargo molecule, such as a pharmaceutical agent, a diagnostic agent, and/or an imaging agent.

In an aspect, the cargo molecule is a protein and is fused to the fusion protein such that the cargo molecule is contained in the nanocage internally.

In an aspect, the cargo molecule is a fluorescent protein, such as GFP, EGFP, Ametrine, and/or a flavin-based fluorescent protein, such as a LOV-protein, such as iLOV.

In an aspect, the cargo molecule is not fused to the fusion protein and is contained in the nanocage internally.

In an aspect, the cargo molecule is contained internally to provide T-cell epitopes, but optionally not B-cell epitopes.

In an aspect, the cargo molecule is fused to the fusion protein and contained internally to provide T-cell epitopes, but optionally not B-cell epitopes.

In an aspect, the cargo molecule is a small molecule, radioisotope, or magnetic particle.

In an aspect, the fusion protein further comprises an antigen on the surface.

In an aspect, the antigen is expressed as a fusion protein with a nanocage monomer.

In accordance with an aspect, there is provided a vaccine comprising the nanocage of described herein.

In accordance with an aspect, there is provided a nucleic acid molecule encoding the fusion protein described herein.

In accordance with an aspect, there is provided a vector comprising the nucleic acid molecule described herein.

In accordance with an aspect, there is provided a host cell comprising the vector of c described herein and producing the fusion protein described herein.

In accordance with an aspect, there is provided a method of immunizing a subject, the method comprising administering the nanocage described herein or the vaccine described herein.

In accordance with an aspect, there is provided a method for treating and/or preventing a disease or condition, the method comprising administering the nanocage described herein or the vaccine described herein.

In an aspect, the disease or condition is cancer, HIV, malaria, or an autoimmune disease.

In accordance with an aspect, there is provided a method for diagnostic imaging, the method comprising administering the nanocage described herein to a subject, tissue, or sample, wherein the nanocage comprises an diagnostic label, such as a fluorescent protein or magnetic imaging moiety, and imaging the subject, tissue, or sample.

In accordance with an aspect, there is provided a use of the fusion protein described herein or the nanocage described herein as a research tool, such as in FACS or in an ELISA.

The novel features of the present invention will become apparent to those of skill in the art upon examination of the following detailed description of the invention. It should be understood, however, that the detailed description of the invention and the specific examples presented, while indicating certain aspects of the present invention, are provided for illustration purposes only because various changes and modifications within the spirit and scope of the invention will become apparent to those of skill in the art from the detailed description of the invention and claims that follow.

BRIEF DESCRIPTION OF THE DRAWINGS

The present invention will be further understood from the following description with reference to the Figures, in which:

FIGS. 1A and 1B show naturally occurring self-assembling nanoparticle backbones of human Ferritin (FIG. 1A) or *Aquifex aeolicus* Lumazine synthase (FIG. 1B) described herein; FIG. 1C shows a schematic for generating single-chain Fab-ferritin nanoparticles that only require transfection of one plasmid.

FIG. 2C shows a schematic representation of an antibody expression nanoparticle described herein;

FIG. 10 shows the sequences of fusion proteins comprising a CSP NANP repeat domain antigen fused to a Fab heavy chain with a linker of varying lengths;

FIG. 21 shows that bi-specific nanoparticles are well folded and display high density of Fabs and antigens;

FIGS. 25A, 25B, 25C, 25D, 25E, 25F, 25G, and 25H show affinity maturation of high-affinity human PfCSP NANP antibodies. (A) Surface plasmon resonance (SPR) affinity and SHM of selected (labeled) VH3-33/Vκ1-5/KCDR3:8 (dark circles) and non-VH3-33/Vκ1-5/KCDR3:8 anti-PfCSP antibodies (light circles) (9). (B to D) Original and mutated antibodies. [(B) and (C)] PfCSP ELISA reactivity. (D) Mean (bars) Pf liver-cell traversal inhibition from two-to-four independent experiments (symbols).  significant (a=0.01) for two-tailed Student's t test. (E) Silent (light) and replacement (dark) SHM (bars) in VH3-33/Vκ1-5 antibodies (n=63). (F) Observed (obs) aa usage compared to baseline (base) model (22, 23). (G and H) Independent NANP3 SPR affinity measurements (dots) and mean (line).  significant (a=0.01) and not significant (ns) for Bonferroni multiple comparisons test. (A), (B), and (C), one representative of at least two independent experiments.

Figure 28:
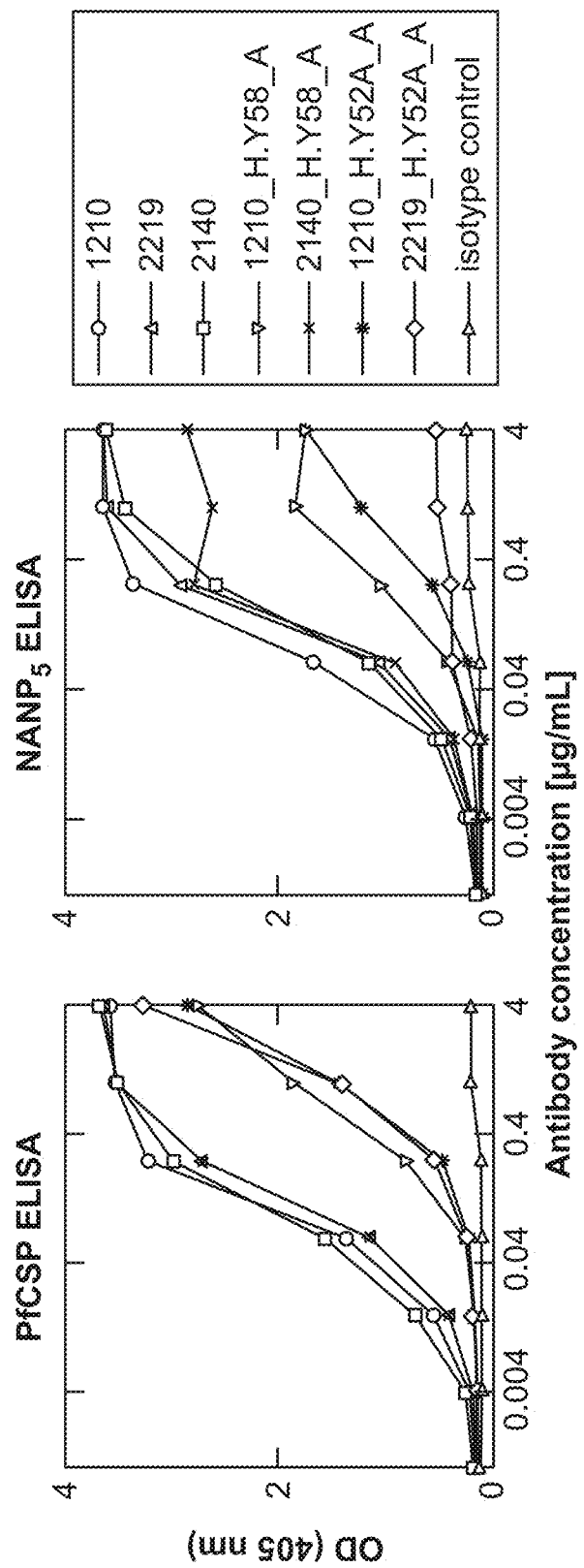
Figure 29A:
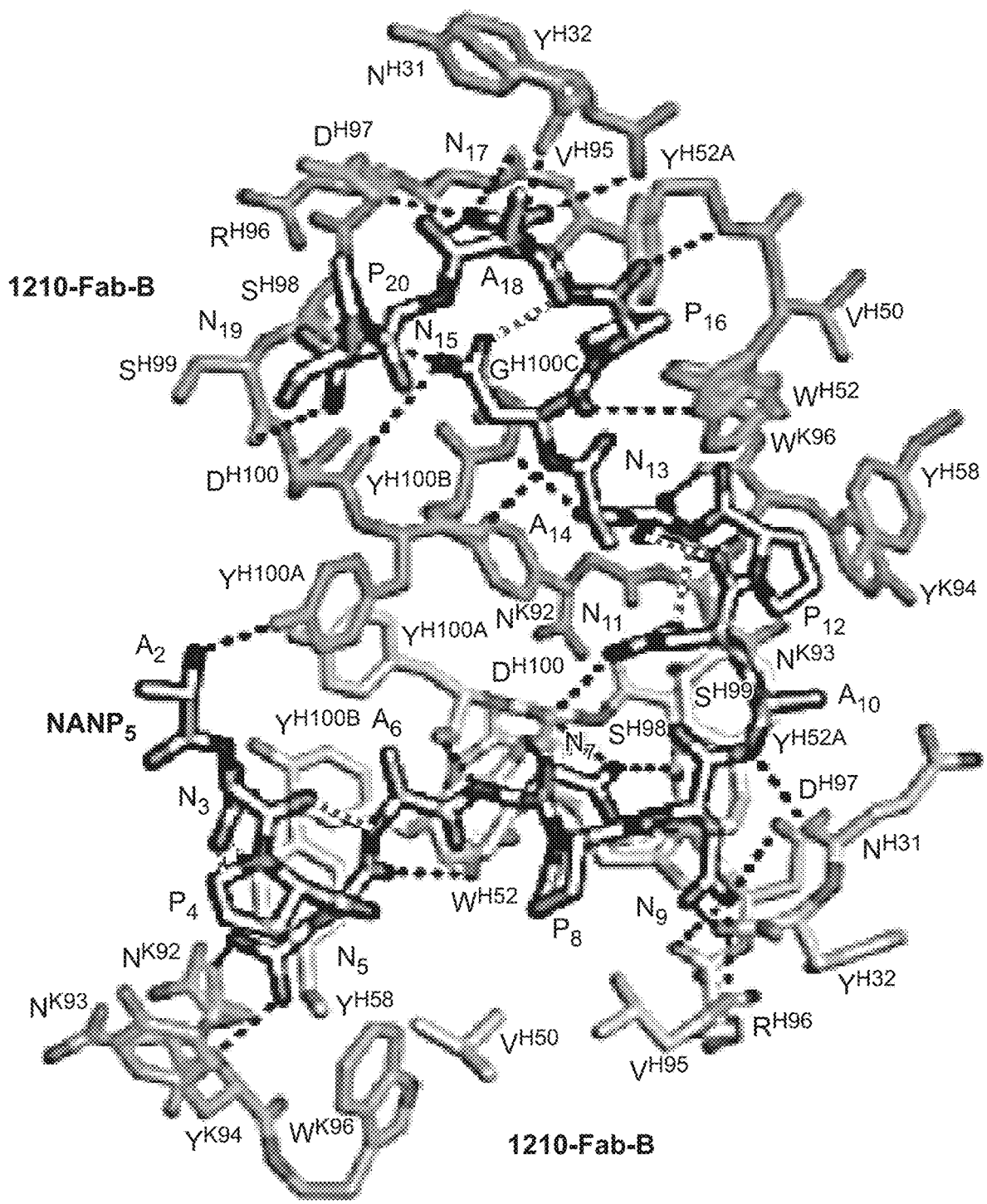
Figure 29B:
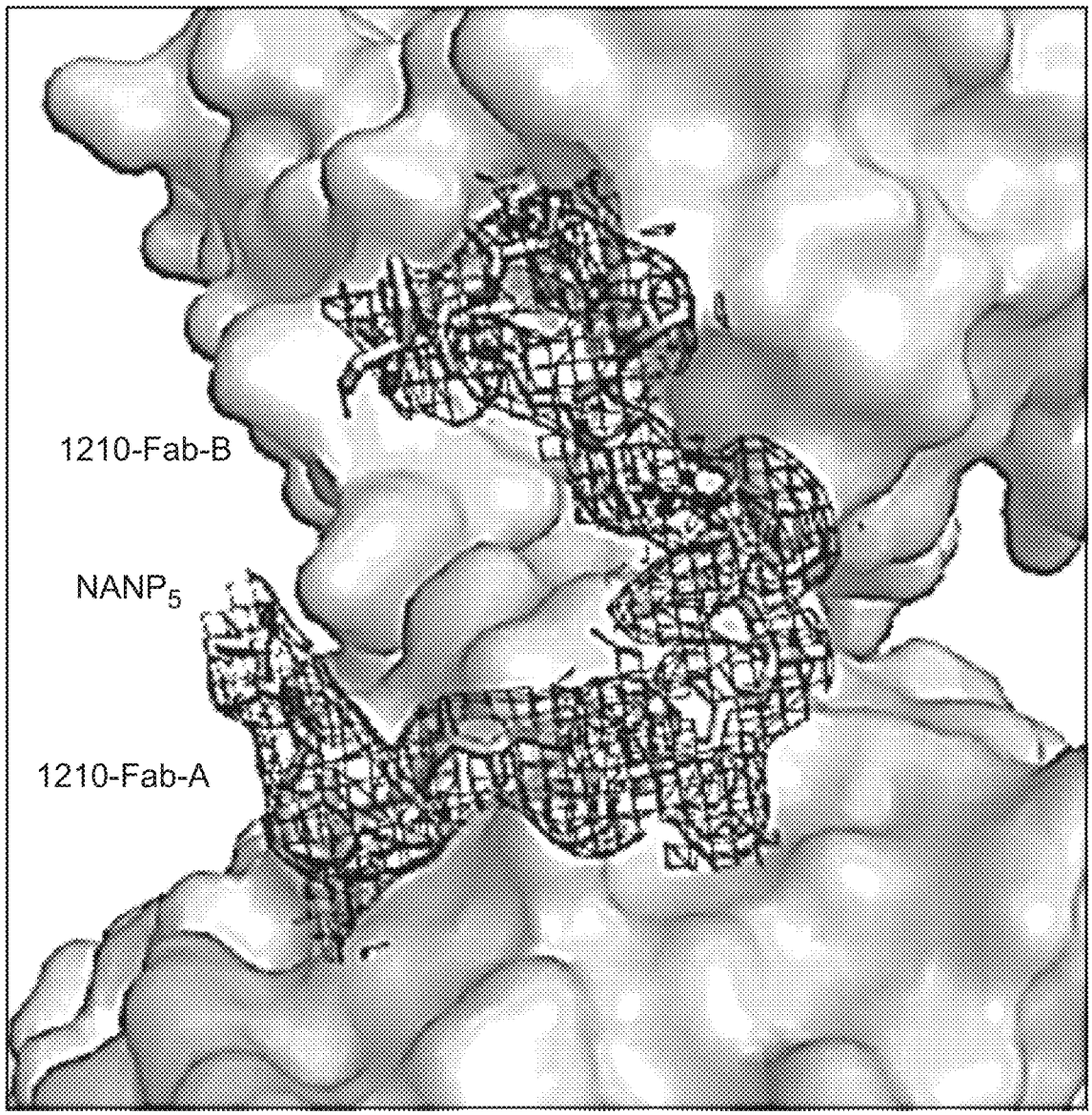
Figure 29C:
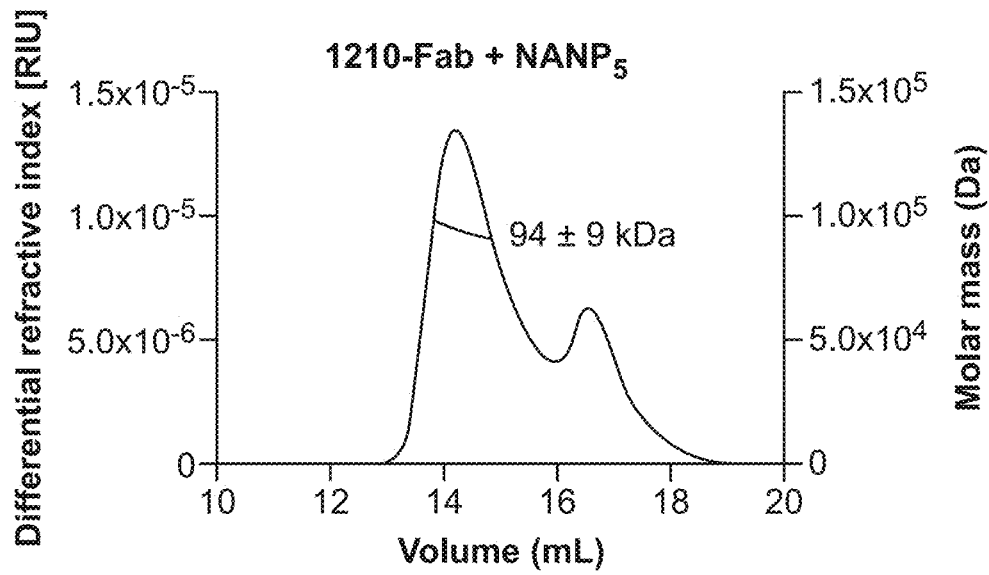
Figure 29D:
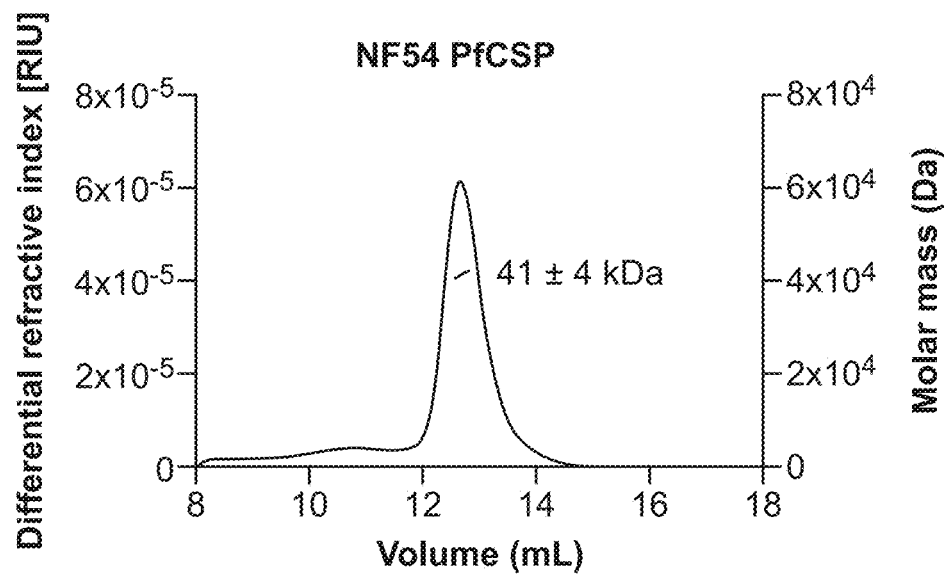

FIG. 28 shows effect of alanine exchange of residues H.Y52A and H.Y58 on antigen binding. PfCSP and NANP5 ELISA reactivity of antibodies 1210, 2140, 2219 and respective mutants with alanine exchanges at positions H.Y52A and H.Y58. One out of three representative experiments is shown.

FIGS. 29A, 29B, 29C, and 29D show 1210-NANP5 crystal structure. A, Detailed interactions of 1210 with NANP5. Intermolecular H-bonds are colored as black dashes and intramolecular H-bonds are colored as gray dashes. B, Unbiased electron density omit map (black mesh) contoured to 1.0 σ for the NANP5 peptide bound to two 1210 Fabs. C, Elution profile of 1210-NANP5 examined by SEC/MALS. The horizontal line corresponds to the calculated molar mass for two 1210 Fabs bound to NANP5. D, Elution profile of full-length PfCSP examined by SEC/MALS. The horizontal line corresponds to the calculated molar mass of the eluting antigen.

Figure 30A:
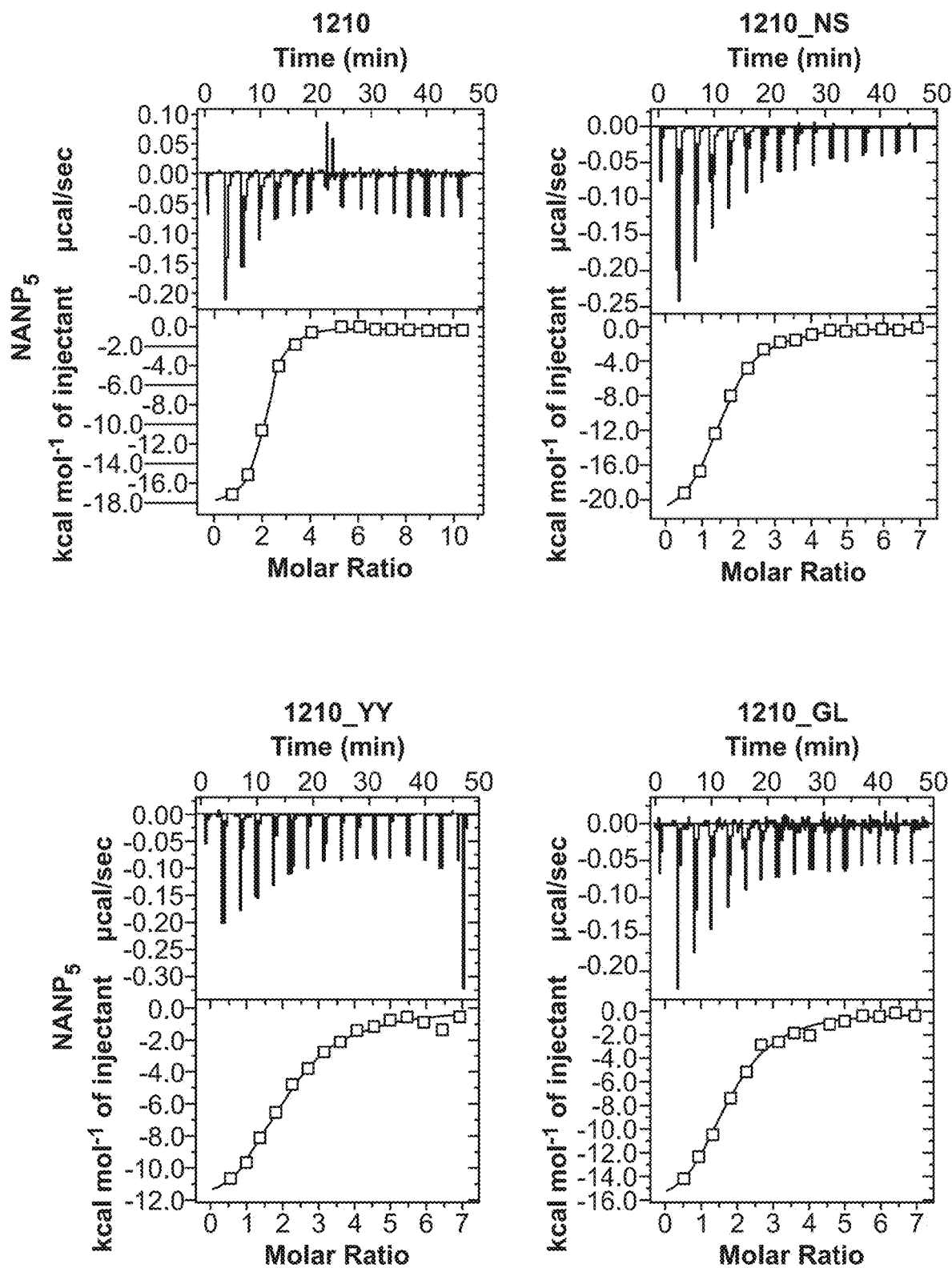
Figure 30B:
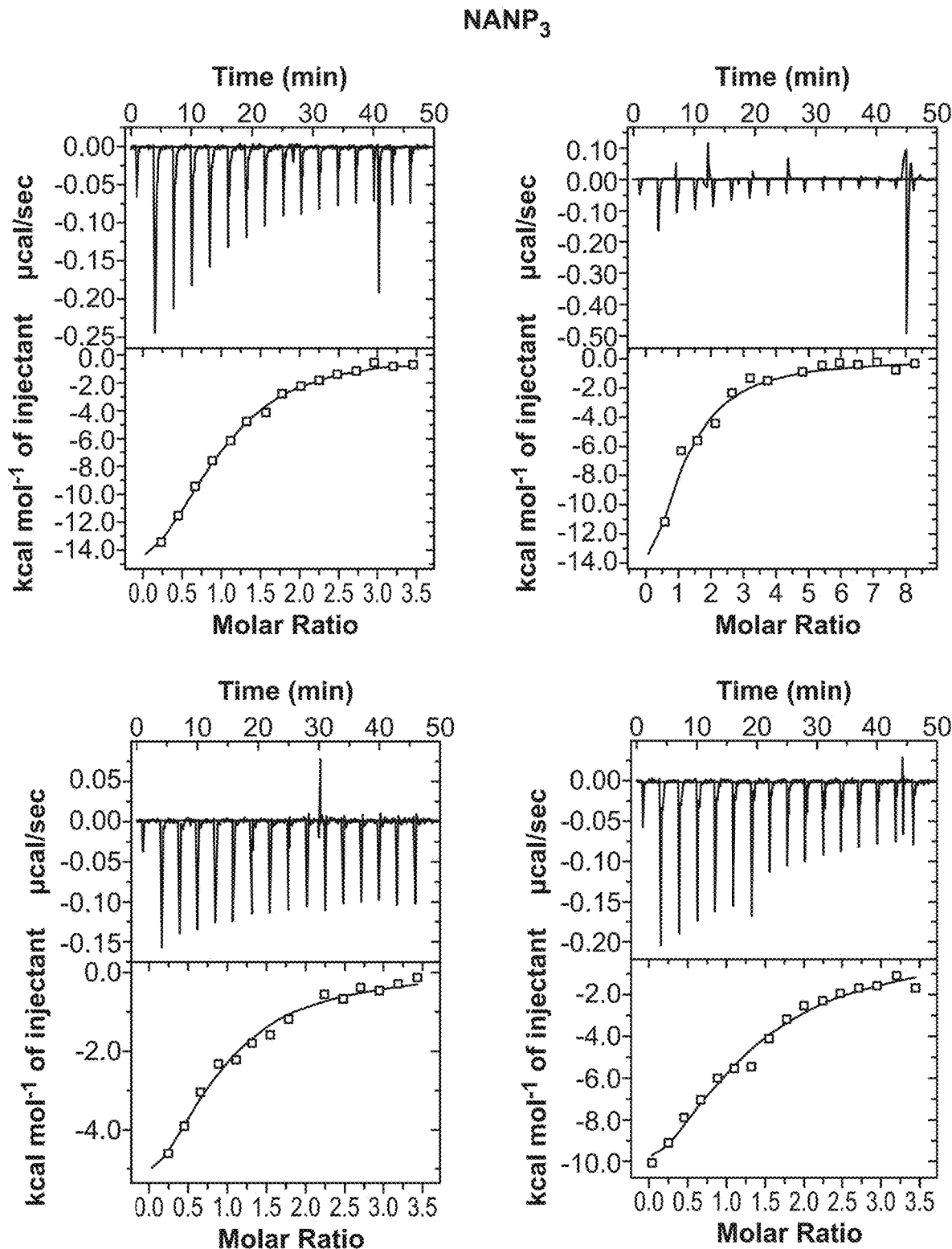

FIGS. 30A, 30B, and 30C show isothermal titration calorimetry of 1210 binding to NANP repeat peptides. A, B, Representative raw ITC data (top panel) and fitted binding curves (bottom panel) are shown for 1210, 1210_NS, 1210_YY and 1210_GL binding to NANP5 (A) and NANP3 (B). C, Summary of measured binding thermodynamic values for these interactions observed in (A) and (B). Mean±SEM for at least three independent experiments is reported.

FIG. 31 shows binding avidity of 1210 and 1210_YY to PfCSP. Representative biolayer interferometry sensorgrams (thick line), 1:1 model best fits (thin line) and calculated binding avidity for (A) 1210 IgG and (B) 1210_YY IgG binding to full length PfCSP.

FIGS. 32A, 32B, 32C, 32D, 32E, and 32F show B cell activation and parasite inhibition. (A to D) NANP5-induced calcium signaling of 1210 and variants. [(A) and (B)] Reaction kinetic and percent activated cells (A), and overlay of median signal intensities (B) to 1 μg/mL NANP5 for one of at least six representative experiments. [(C) and (D)] Percent activated cells and median activation time after 1 μg/ml (C) (n=6 or 7) and 0.1 μg/mL (D) (n=3) NANP5. Symbols indicate independent experiments, lines and error bars indicate mean±SD. ** significant (a=0.01) and not significant (ns) for Bonferroni multiple comparisons test. (E and F) Parasite inhibition. (E) Mean±SD IC50 values from at least three independent experiments for 1210 (circles) and 2163 (squares) antibodies with indicated NANP3 affinities. No significant differences between IC50 values due to extensively overlapping confidence intervals. (F) Parasite-free mice after passive immunization with 30 μg or 100 μg of 1210 or variants 24 hours before subcutaneous injection with Pb-PfCSP sporozoites. Data show one (100 μg) or two (30 μg) independent experiments with five mice per group. No significant differences in survival for 1210 variants (Mantel-Cox test).

Figure 33A:
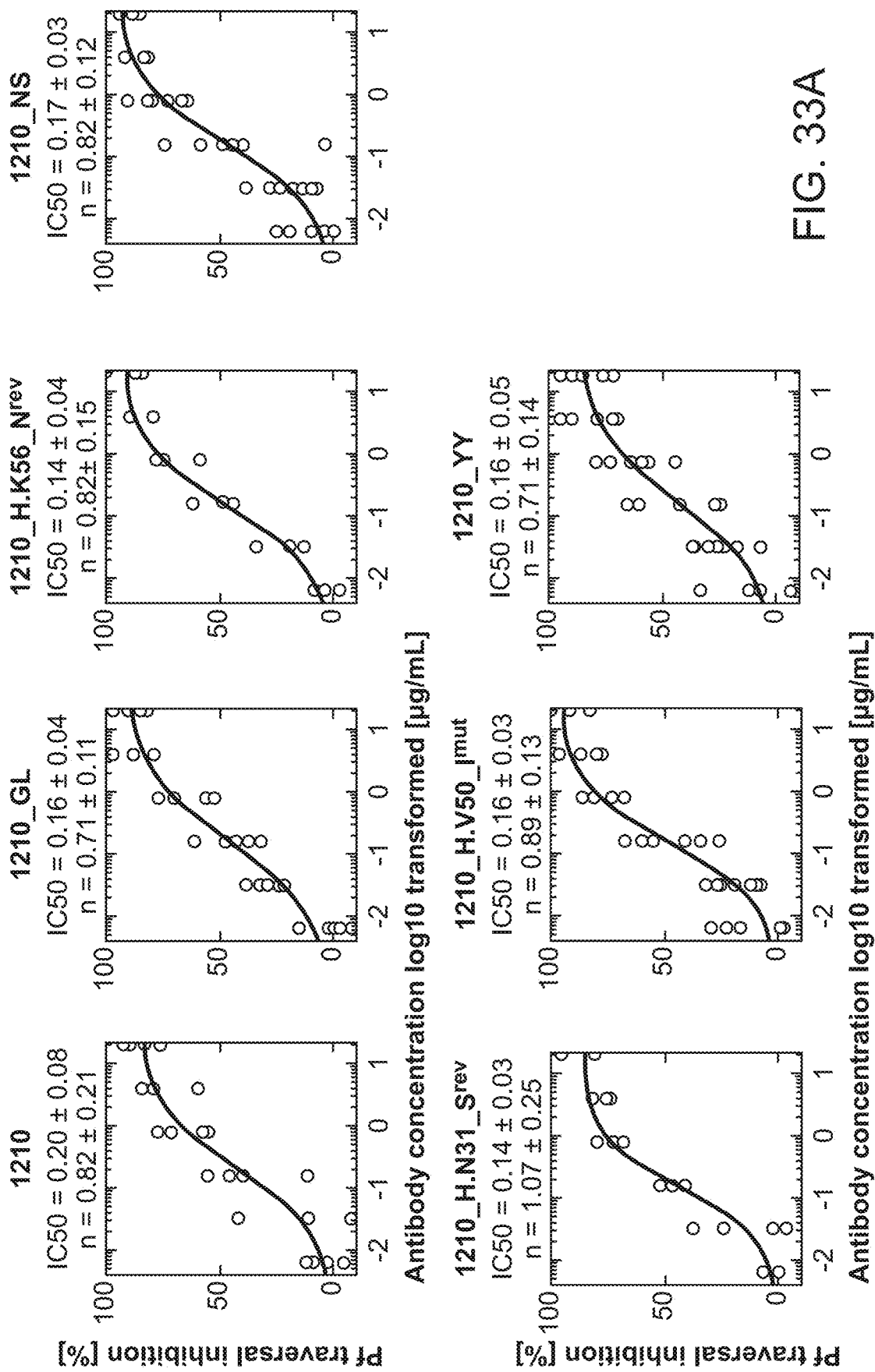
Figure 33B:
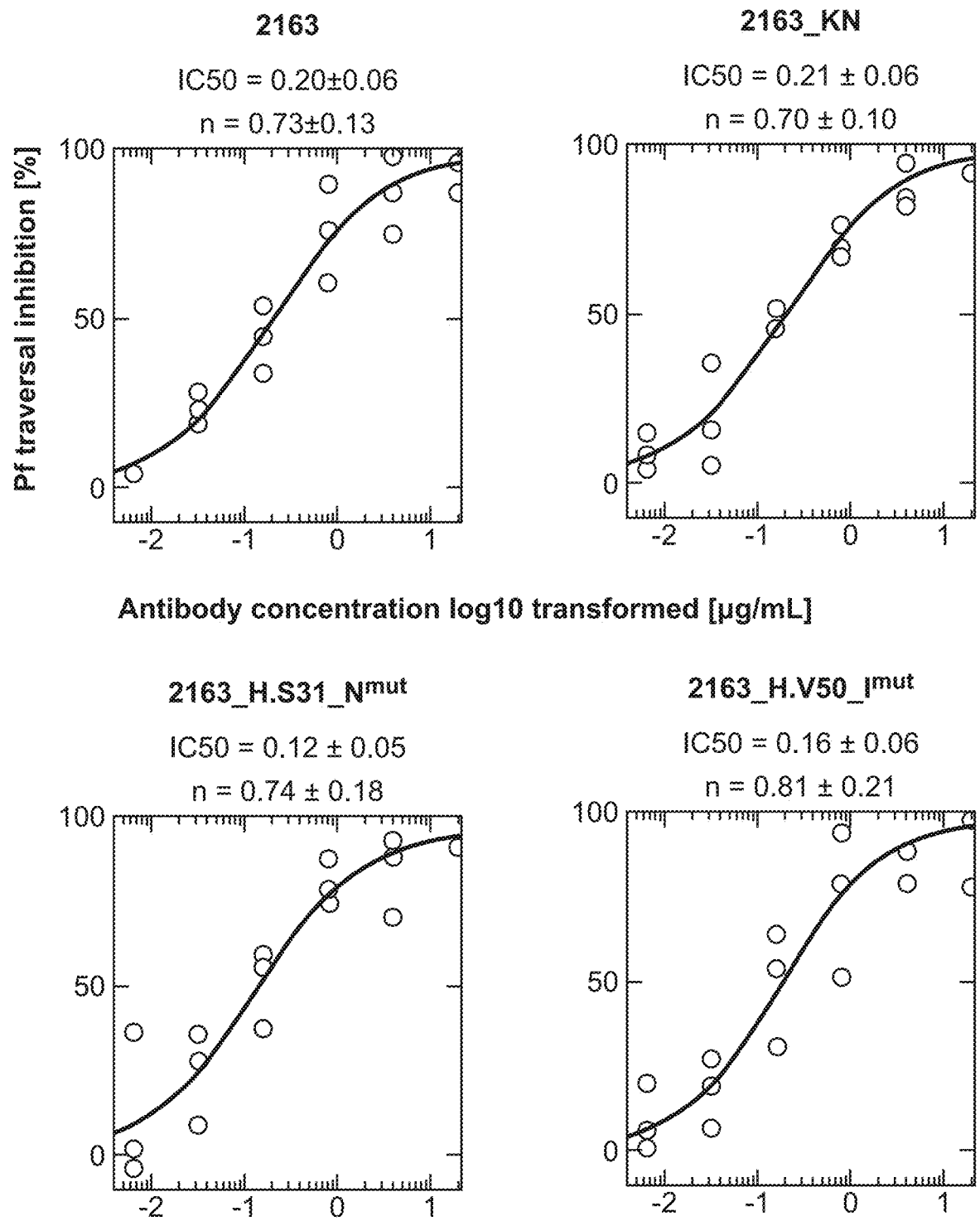
Figure 33C:
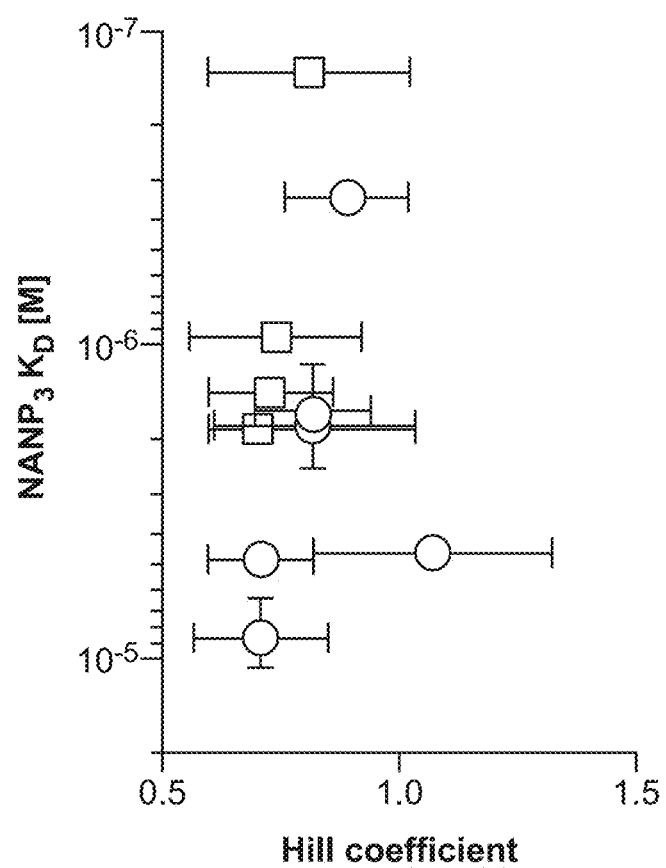

FIGS. 33A, 33B, and 33C show antibody mediated inhibition of Pf hepatocyte traversal. A, B, Pf hepatocyte traversal inhibition for 1210 (A), 2163 (B), as well as the indicated variants. The IC50 values (in g/mL) and Hill coefficient (n) values and their standard deviations are indicated above each plot. C, NANP3 affinities and Hill coefficient for 1210 (circles) and 2163 (squares) as well as the respective variants as shown in (A and B). Error bars indicate standard deviation.

FIGS. 34A, 34B, 34C, 34D, 34E, 34F, and 34G show antihomotypic affinity maturation in IGHV3-23-encoded PfCSP NANP antibodies. (A) SPR affinity and SHM of 1450 out of all VH3-23/Vκ1-5 (dark circles) and non-VH3-23/Vκ1-5 anti-PfCSP antibodies (light circles) (9). (B) Silent (light) and replacement (dark) SHM (bars) in VH3-23/Vκ1-5 antibodies (n=100). (C to E) Fab 1450-NANP5 co-crystal structure. Head-to-head binding mode (C), Fab-Fab (D), and Fab-NANP5 (E) interactions. Black dashes indicate H-bonds. Affinity-matured residues are colored according to SHM aa usage scheme and labeled with bold and underlined font. Observed (obs) aa usage compared to baseline (base) model (22, 23). (F) VH3-33/Vκ1-5/KCDR3: 8 or VH3-23/Vκ1-5 antibodies in total memory B cells (18) and CD19+CD27hiCD38hiplasmablasts (PB) and CD19+CD27+PfCSP-reactive memory B cells (CSPmem) (8, 9). Dots represent subsamples of n=1500 sequences. Boxplots show median, standard deviation, max and min of the distribution. *** significant (a=0.001) for two-tailed Student's t test. (G) Frequency of VH3-33/Vκ1-5/KCDR3: 8 and VH3-23/Vκ1-5 antibodies among clonally expanded vs. singlet pooled PB and CSPmem (9).

Figure 35A:
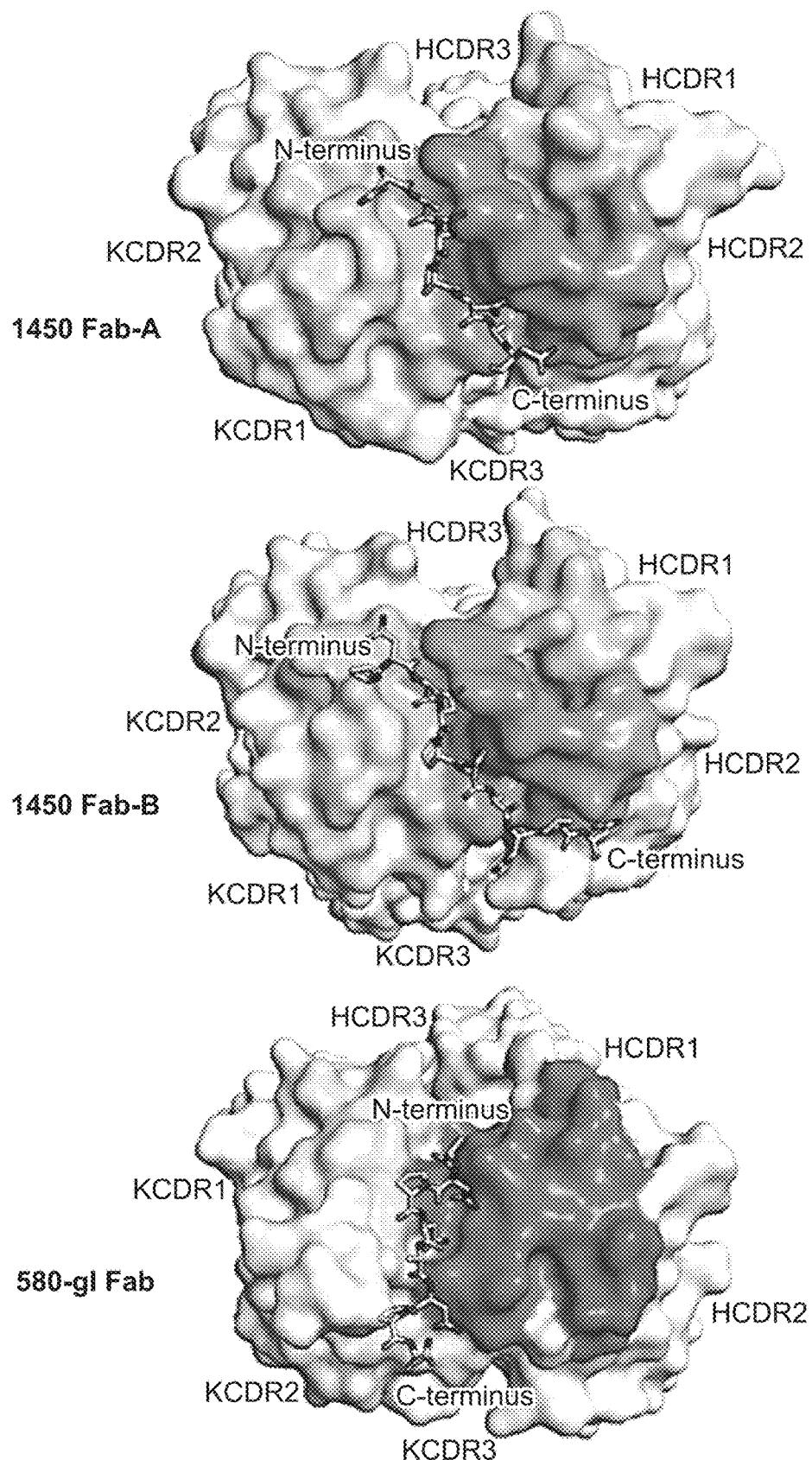
Figure 35B:
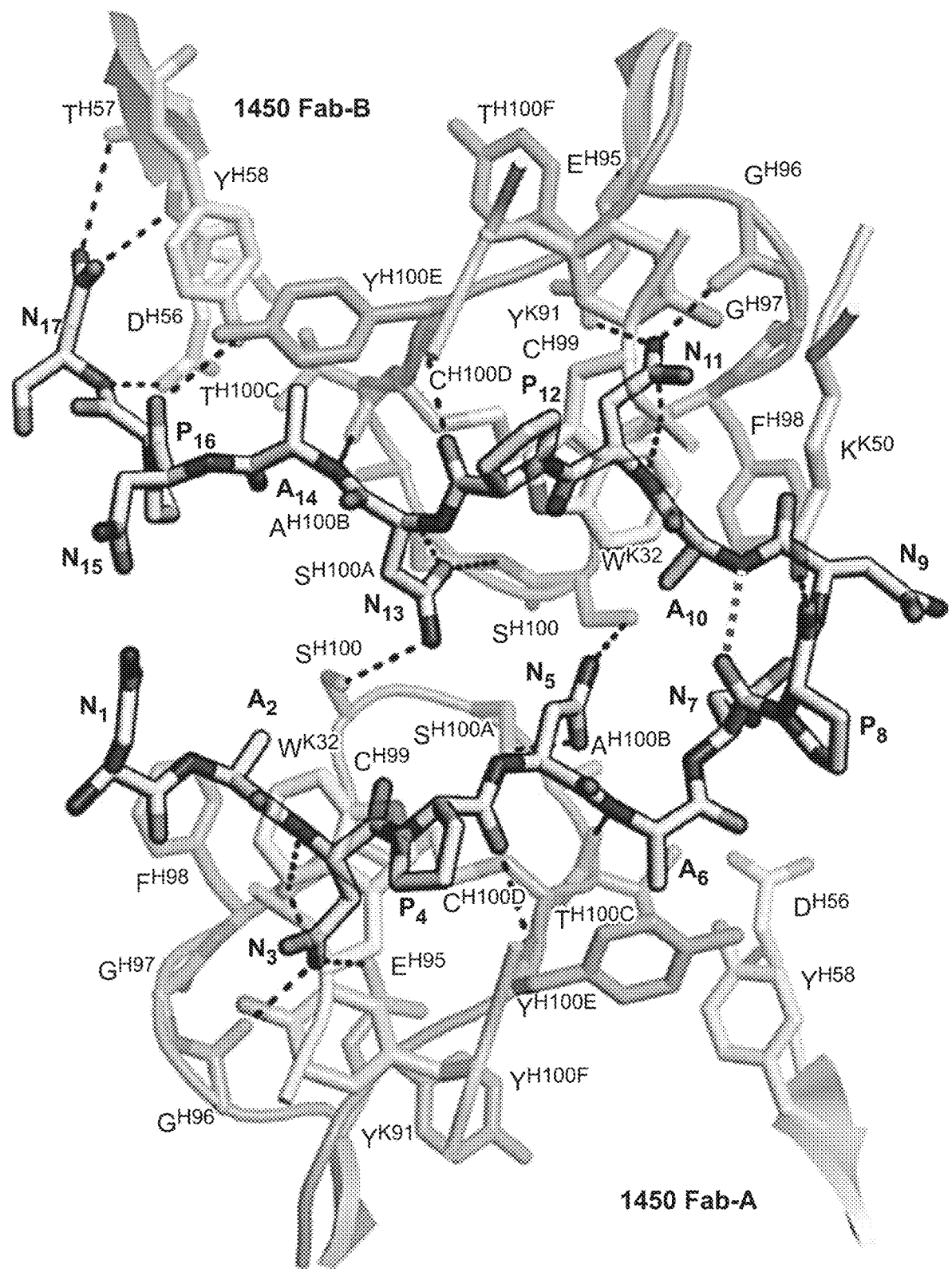
Figure 36A:
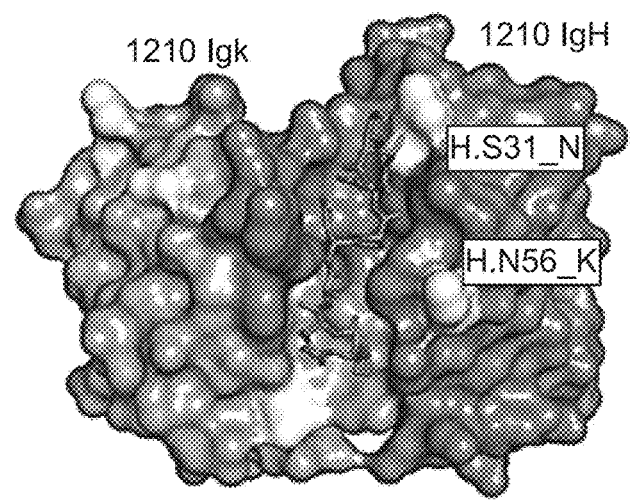
Figure 36B:
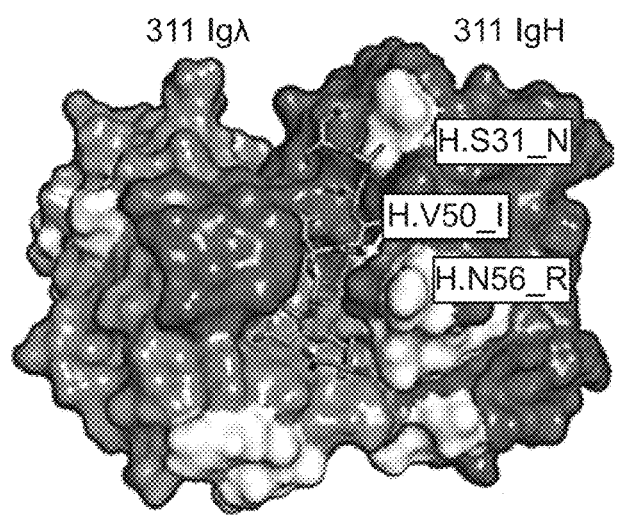
Figure 36C:
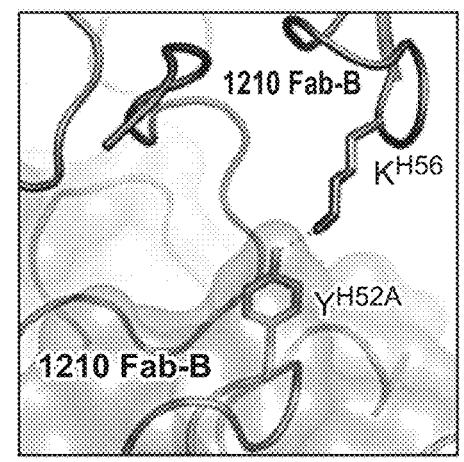
Figure 36D:
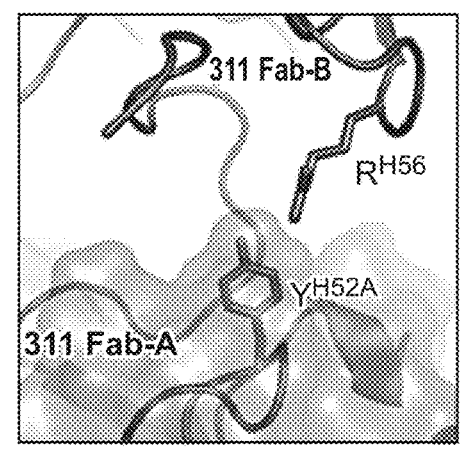

FIGS. 35A and 35B show NANP5 repeat binding by antibodies 1450 and 580-gl. A, Surface representation of the 1450 and 580-gl (PDB 6AZM, (10)) paratopes bound to NANP5. B, Detailed interactions of 1450 with NANP5. Intermolecular H-bonds are colored as black dashes and intramolecular H-bonds are colored as gray dashes.

FIGS. 36A, 36B, 36C, and 36D show structure comparison of 1210 and the RTS,S vaccine-induced NANP antibody 311 (encoded by IGHV3-33 and IGLV1-40). Similar antigen-binding conformations are observed for recognition of the minimal NPNANPNANA repeat epitope. Analogous to the anti-homotypic mutation H.N56_K in 1210, 311 possesses H.N56_R, suggesting that it may also have undergone anti-homotypic affinity maturation. A, 1210 Igκ chain is shown in light gray, 1210 IgH chain is shown in dark gray. B, 311 IgA chain is shown in light gray, 311 IgH chain is shown in dark gray. NANP repeat antigens are shown as a branched structure. Mutated residues are colored in white. AA-exchanges at positions H.31, H.50 and H.56 are highlighted. C, D, Detailed representation of homotypic HCDR2 interactions between 1210 (C) and 311 (D) Fabs binding neighboring repeat epitopes. For D the structure of the 311-NANP complex was duplicated and structurally aligned to both Fab-A and Fab-B of the 1210_NANP5 complex. Affinity matured residues H.K56 (C, 1210 Fab) and H.R56 (D, 311 Fab, (11)) are labeled in red.

Figure 37:
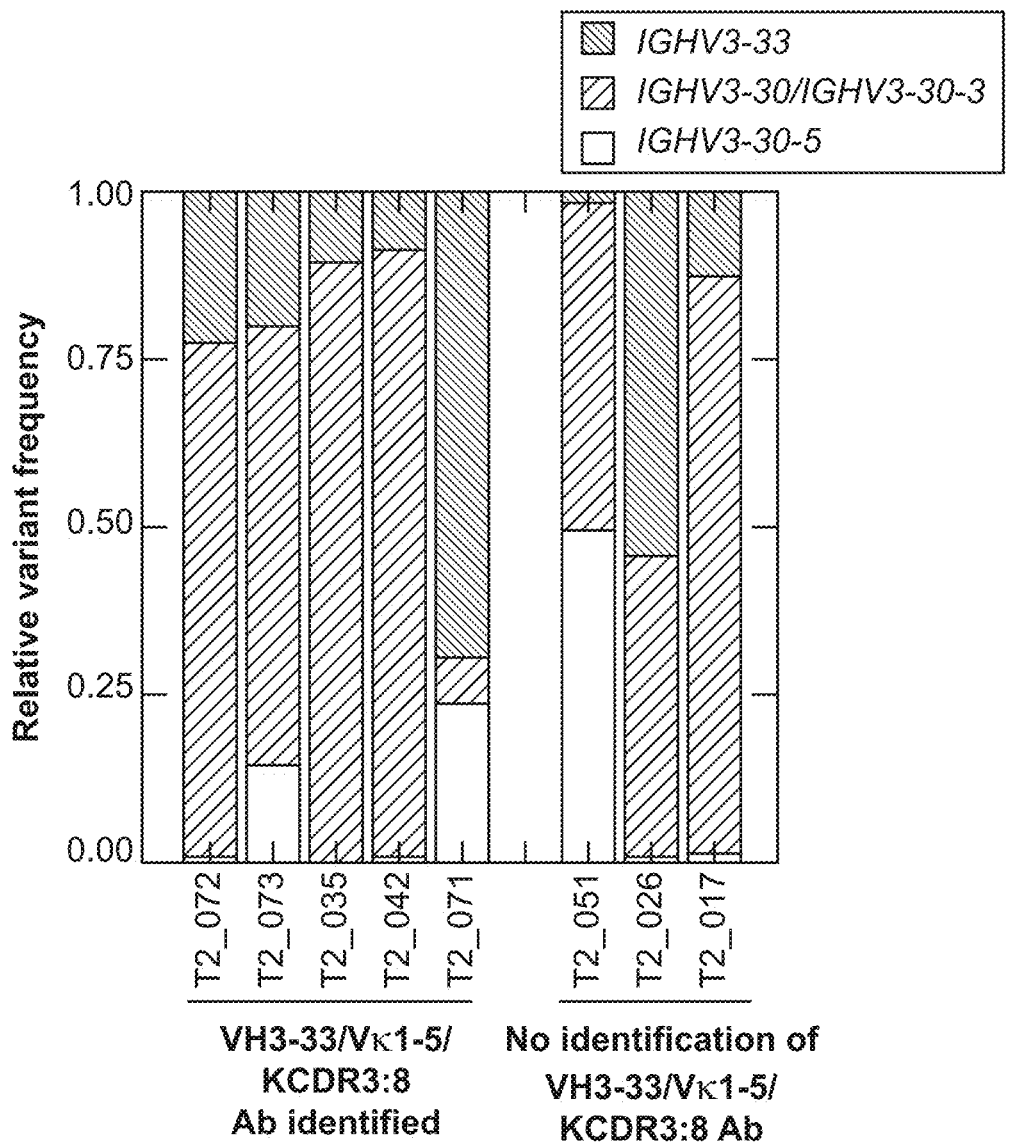

FIG. 37 shows IGHV3-33, IGHV3-30/IGHV3-30-3, IGHV3-30-5 gene frequency. Frequency of IGHV3-33, IGHV3-30/IGHV3-30-3, IGHV3-30-5 germline gene segments (8,9) as determined by genomic sequencing of peripheral blood mononuclear cells. Sequences were assigned to the respective germline gene based on their CDR2 sequence as shown in Table 1.

Figure 38:
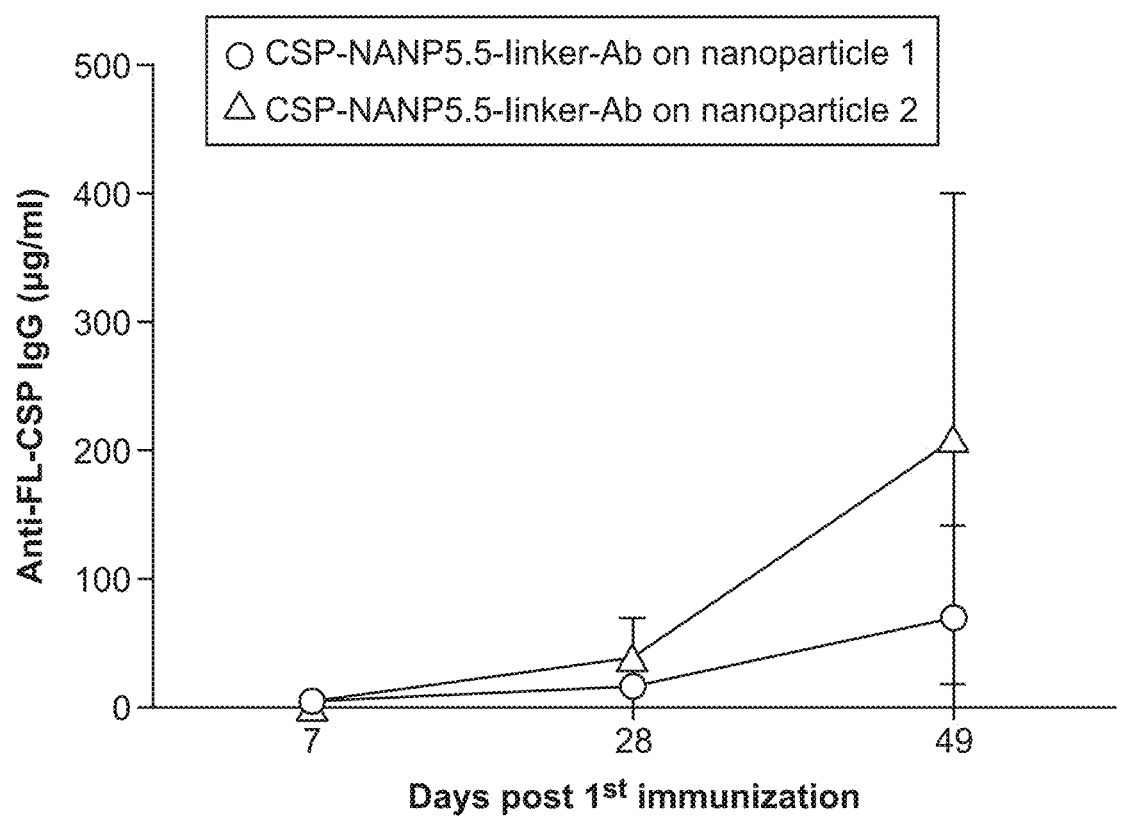

FIG. 38 shows that the malaria vaccine antigen (CSP-NANP5.5-linker-antibody) elicits IgG titers that can recognize the full-length PfCSP antigen.

Figure 25D:
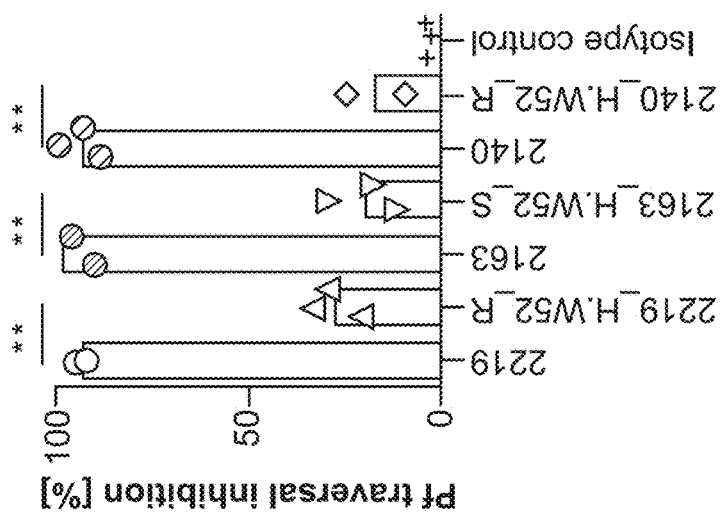
Figure 25C:
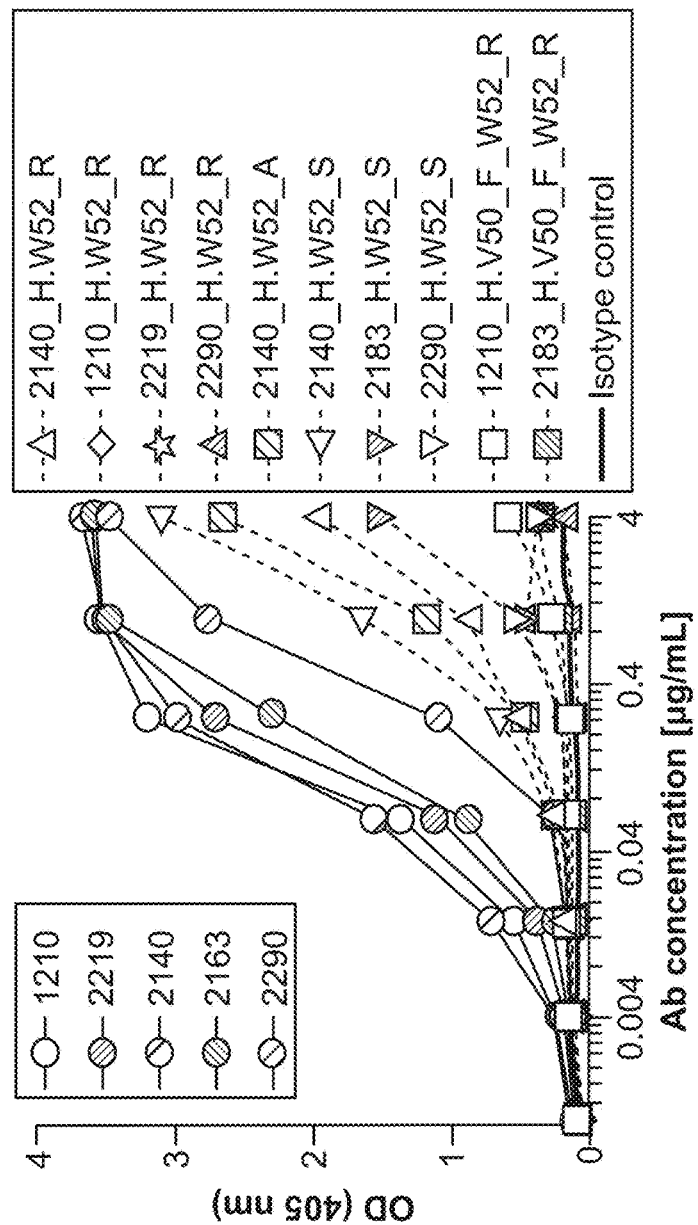
Figures 25G, 25H:
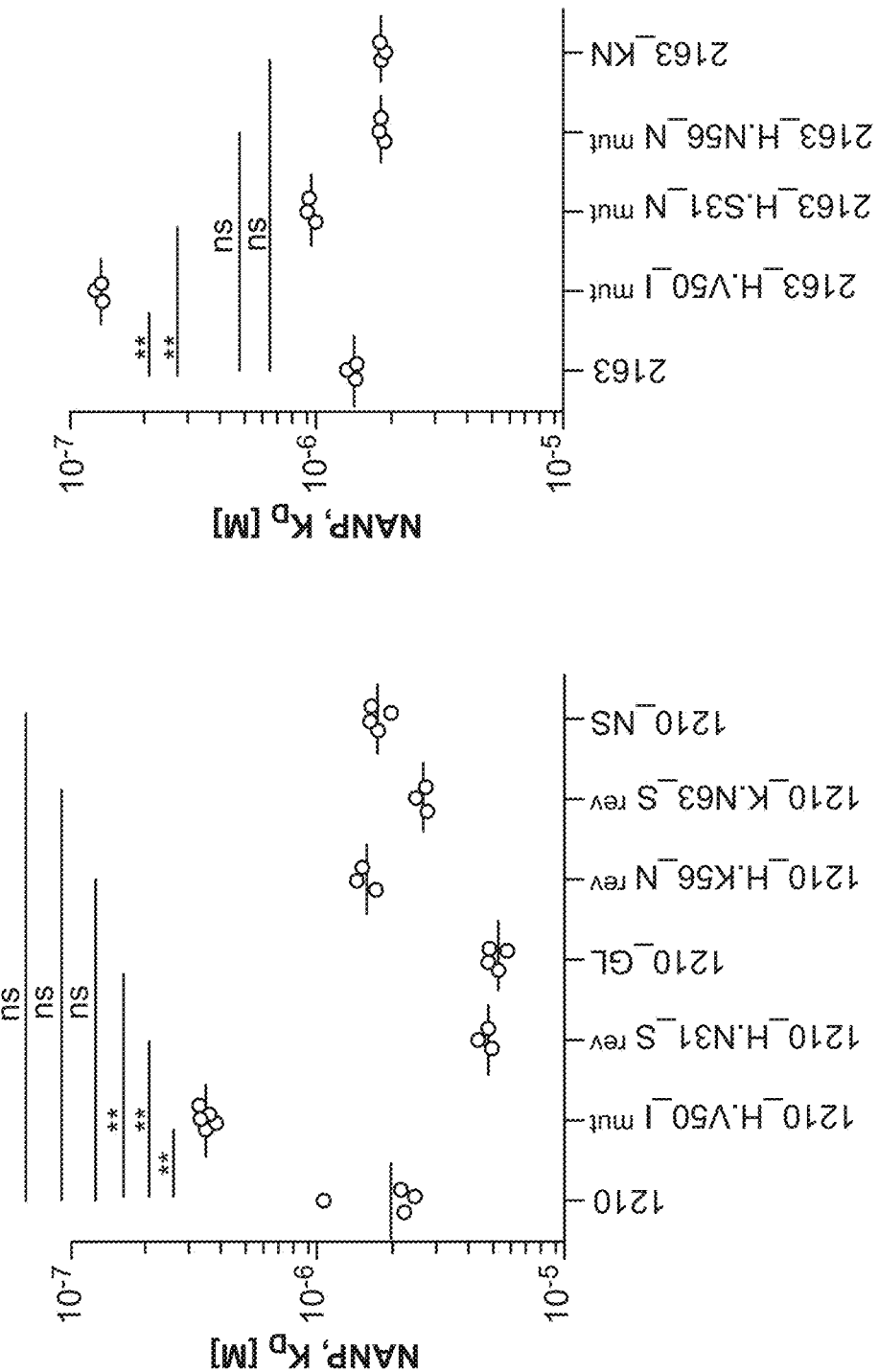
Figure 39:
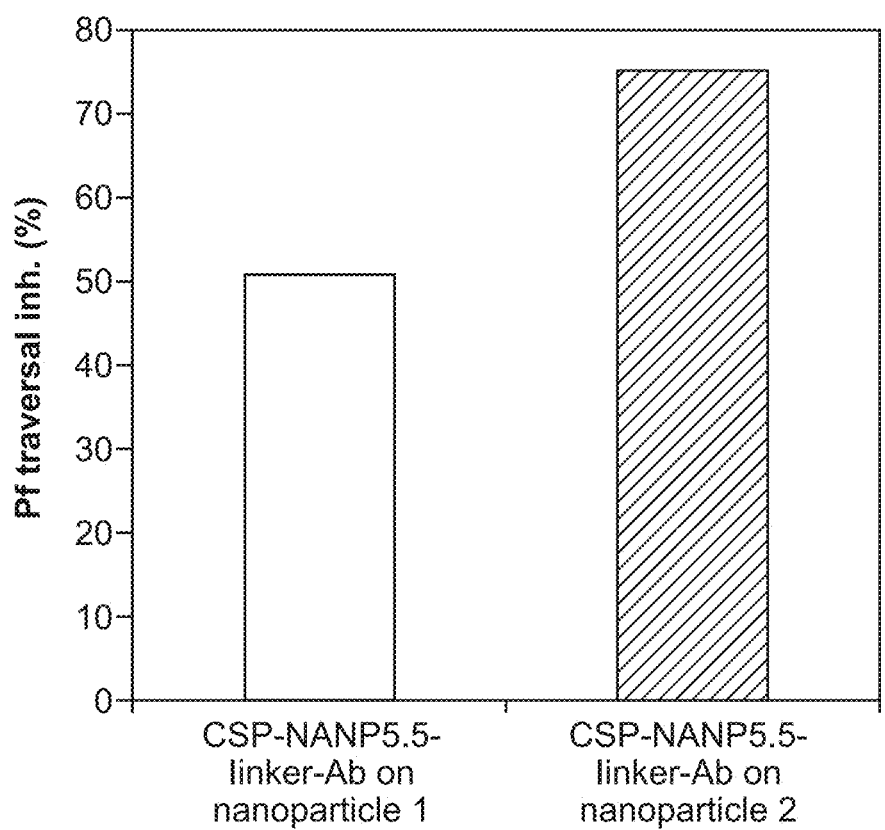

FIG. 39 shows the activity/function of the elicited anti-PfCSP sera from the immunizations in FIG. 25.

DETAILED DESCRIPTION OF CERTAIN ASPECTS

Definitions

Unless otherwise explained, all technical and scientific terms used herein have the same meaning as commonly understood by one of ordinary skill in the art to which this disclosure belongs. Definitions of common terms in molecular biology may be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8). Although any methods and materials similar or equivalent to those described herein can be used in the practice for testing of the present invention, the typical materials and methods are described herein. In describing and claiming the present invention, the following terminology will be used.

It is also to be understood that the terminology used herein is for the purpose of describing particular aspects only, and is not intended to be limiting. Many patent applications, patents, and publications are referred to herein to assist in understanding the aspects described. Each of these references are incorporated herein by reference in their entirety.

In understanding the scope of the present application, the articles "a", "an", "the", and "said" are intended to mean that there are one or more of the elements. Additionally, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

It will be understood that any aspects described as "comprising" certain components may also "consist of" or "consist essentially of," wherein "consisting of" has a closed-ended or restrictive meaning and "consisting essentially of" means including the components specified but excluding other components except for materials present as impurities, unavoidable materials present as a result of processes used to provide the components, and components added for a purpose other than achieving the technical effect of the invention.

For example, a composition defined using the phrase "consisting essentially of" encompasses any known acceptable additive, excipient, diluent, carrier, and the like. Typically, a composition consisting essentially of a set of components will comprise less than 5% by weight, typically less than 3% by weight, more typically less than 1%, and even more typically less than 0.1% by weight of non-specified component(s).

It will be understood that any component defined herein as being included may be explicitly excluded from the claimed invention by way of proviso or negative limitation.

In addition, all ranges given herein include the end of the ranges and also any intermediate range points, whether explicitly stated or not.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example." The word "or" is intended to include "and" unless the context clearly indicates otherwise.

The terms "protein nanoparticle" and "nanocage" are used interchangeably herein and refer to a multi-subunit, protein-based polyhedron shaped structure. The subunits or nanocage monomers are each composed of proteins or polypeptides (for example a glycosylated polypeptide), and, optionally of single or multiple features of the following: nucleic acids, prosthetic groups, organic and inorganic compounds. Non-limiting examples of protein nanoparticles include ferritin nanoparticles (see, e.g., Zhang, Y. Int. J. Mol. Sci., 12:5406-5421, 2011, incorporated by reference herein), encapsulin nanoparticles (see, e.g., Sutter et al., Nature Struct, and Mol. Biol., 15:939-947, 2008, incorporated by reference herein), Sulfur Oxygenase Reductase (SOR) nanoparticles (see, e.g., Urich et al., Science, 311:996-1000, 2006, incorporated by reference herein), lumazine synthase nanoparticles (see, e.g., Zhang et al., J. Mol. Biol., 306: 1099-1114, 2001) or pyruvate dehydrogenase nanoparticles (see, e.g., Izard et al., PNAS 96:1240-1245, 1999, incorporated by reference herein). Ferritin, encapsulin, SOR, lumazine synthase, and pyruvate dehydrogenase are monomeric proteins that self-assemble into a globular protein complexes that in some cases consists of 24, 60, 24, 60, and 60 protein subunits, respectively. Carboxysome, vault proteins, GroEL, heat shock protein, E2P and MS2 coat protein also produce nanocages are contemplated for use herein. In addition, fully or partially synthetic self-assembling monomers are also contemplated for use herein.

A "vaccine" is a pharmaceutical composition that induces a prophylactic or therapeutic immune response in a subject. In some cases, the immune response is a protective immune response. Typically, a vaccine induces an antigen-specific immune response to an antigen of a pathogen, for example a viral pathogen, or to a cellular constituent correlated with a pathological condition. A vaccine may include a polynucleotide (such as a nucleic acid encoding a disclosed antigen), a peptide or polypeptide (such as a disclosed antigen), a virus, a cell or one or more cellular constituents. In one specific, non-limiting example, a vaccine induces an immune response that reduces the severity of the symptoms associated with malaria infection and/or decreases the parasite load compared to a control. In another non-limiting example, a vaccine induces an immune response that reduces and/or prevents malaria infection compared to a control.

The term "antibody", also referred to in the art as "immunoglobulin" (Ig), used herein refers to a protein constructed from paired heavy and light polypeptide chains; various Ig isotypes exist, including IgA, IgD, IgE, IgG, such as $IgG_1$, $IgG_2$, $IgG_3$, and $IgG_4$, and IgM. It will be understood that the antibody may be from any species, including human, mouse, rat, monkey, llama, or shark. When an antibody is correctly folded, each chain folds into a number of distinct globular domains joined by more linear polypeptide sequences. For example, the immunoglobulin light chain folds into a variable ($V_L$) and a constant (CL) domain, while the heavy chain folds into a variable ($V_H$) and three constant ($C_H$, $C_{H2}$, $C_{H3}$) domains. Interaction of the heavy and light chain variable domains ($V_H$ and $V_L$) results in the formation of an antigen binding region (Fv). Each domain has a well-established structure familiar to those of skill in the art.

The light and heavy chain variable regions are responsible for binding the target antigen and can therefore show significant sequence diversity between antibodies. The constant regions show less sequence diversity, and are responsible for binding a number of natural proteins to elicit important immunological events. The variable region of an antibody contains the antigen binding determinants of the molecule, and thus determines the specificity of an antibody for its target antigen. The majority of sequence variability occurs in six hypervariable regions, three each per variable heavy and light chain; the hypervariable regions combine to form the antigen-binding site, and contribute to binding and recognition of an antigenic determinant. The specificity and affinity of an antibody for its antigen is determined by the structure of the hypervariable regions, as well as their size, shape and chemistry of the surface they present to the antigen.

An "antibody fragment" as referred to herein may include any suitable antigen-binding antibody fragment known in the art. The antibody fragment may be a naturally-occurring antibody fragment, or may be obtained by manipulation of a naturally-occurring antibody or by using recombinant methods. For example, an antibody fragment may include, but is not limited to a Fv, single-chain Fv (scFv; a molecule consisting of $V_L$ and $V_H$ connected with a peptide linker), Fc, single-chain Fc, Fab, F(ab')$_2$, single domain antibody (sdAb; a fragment composed of a single $V_L$ or $V_H$), and multivalent presentations of any of these.

By the term "synthetic antibody" as used herein, is meant an antibody which is generated using recombinant DNA technology. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "epitope" refers to an antigenic determinant. An epitope is the particular chemical groups or peptide sequences on a molecule that are antigenic, that is, that elicit a specific immune response. An antibody specifically binds a particular antigenic epitope, e.g., on a polypeptide. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, about 11, or about 8 to about 12 amino acids in a unique spatial conformation. Methods of determining spatial conformation of epitopes include, for example, x-ray crystallography and 2-dimensional nuclear magnetic resonance. See, e.g., "Epitope Mapping Protocols" in *Methods in Molecular Biology*, Vol. 66, Glenn E. Morris, Ed (1996).

The term "antigen" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequence or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the aspects described herein include, but are not limited to, the use of partial nucleotide sequences of more than one gene and that these nucleotide sequences could be arranged in various combinations to elicit the desired immune response. Moreover, a skilled artisan will understand that an antigen need not be encoded by a "gene" at all. It is readily apparent that an antigen can be synthesized or can be derived from a biological sample. Such a biological sample can include, but is not limited to a tissue sample, a cell, or a biological fluid.

Thus, the compositions described herein may be suitable for protection or treatment of vertebrate subjects against a variety of disease states such as, for example, viral, bacterial, fungal or parasitic infections, cancer, and autoimmune disorders. It is to be recognized that these specific disease states have been referred to by way of example only and are not intended to be limiting.

Suitable antigens useful in combination with the compositions described herein include any antigen as defined herein. Antigens are commercially available or one of skill in the art is capable of producing them. The antigen can be either a modified-live or killed microorganism, or a natural product purified from a microorganism or other cell including, but not limited to, tumor cell, a synthetic product, a genetically engineered protein, peptide, polysaccharide or similar product, or an allergen. The antigenic moiety can also be a subunit of a protein, peptide, polysaccharide or similar product. The antigen may also be a genetic antigen, i.e., DNA or RNA that engenders an immune response.

Representative of the antigens that can be used include, but are not limited to, natural, recombinant or synthetic products derived from viruses, bacteria, fungi, parasites and other infectious agents in addition to autoimmune diseases, hormones, or tumor antigens which might be used in prophylactic or therapeutic vaccines and allergens. In one embodiment, the antigen comprises virus-like particles (VLPs) from various viruses such as influenza, HIV, RSV, Newcastle disease virus (NDV) etc. See PCT/US2006/40862, PCT/US2004/022001, U.S. Ser. No. 11/582,540, U.S. 60/799,343, U.S. 60/817,402, U.S. 60/859,240, all of which are herein incorporated by reference in their entirety. In another embodiment, the antigen comprises chimeric VLPs. "Chimeric VLPs" refer to VLPs that contain proteins, or portions thereof, from at least two different sources (organisms). Usually, one protein is derived from a virus that can drive the formation of VLPs from host cells. Thus, in one embodiment, said chimeric VLP comprises an RSV M protein. In another embodiment, said chimeric VLP comprises a NDV M protein. In another embodiment, said chimeric VLP comprises an influenza virus M protein.

The viral or bacterial products can be components which the organism produced by enzymatic cleavage or can be components of the organism that were produced by recombinant DNA techniques that are well known to those of ordinary skill in the art.

Some specific examples of antigens are antigens derived from viral infections caused by hepatitis viruses A, B, C, D & E3, human immunodeficiency virus (HIV), herpes viruses 1, 2, 6 & 7, cytomegalovirus, varicella zoster, papilloma virus, Epstein Barr virus, para-influenza viruses, adenoviruses, bunya viruses (e.g. hanta virus), coxsakie viruses, picoma viruses, rotaviruses, respiratory syncytial viruses, rhinoviruses, rubella virus, papovavirus, mumps virus, measles virus, polio virus (multiple types), adeno virus (multiple types), parainfluenza virus (multiple types), avian or pandemic influenza (various types), seasonal influenza, shipping fever virus, Western and Eastern equine encephalomyelitis, Japanese B. encephalomyelitis, Russian Spring Summer encephalomyelitis, hog cholera virus, Newcastle disease virus, fowl pox, rabies, feline and canine distemper and the like viruses, slow brain viruses, rous sarcoma virus (RSV), Papovaviridae, Parvoviridae, Picornaviridae, Poxyiridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, encephalitis, eye infections (e.g., conjunctivitis, keratitis), chronic fatigue syndrome, Japanese B encephalitis, Junin, Chikungunya, Rift Valley fever, yellow fever, meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia.

The antigens may also be derived from bacterial and fungal infections for example: antigens derived from infections caused by Mycobacteria causing TB and leprosy, pneumocci, aerobic gram negative bacilli, *mycoplasma*, staphyloccocal infections, streptococcal infections, salmonellae and chlamydiae, *B. pertussis, Leptospira pomona*, and icterohaemorrhagiae. Specific embodiments comprise S. paratyphi A and B, *C. diphtheriae, C. tetani, C. botulinum, C. perfringens, C. feseri* and other gas gangrene bacteria, *B. anthracis, P. pestis, P. multocida, Neisseria meningitidis, N. gonorrheae, Hemophilus influenzae, Actinomyces* (e.g., Norcardia), *Acinetobacter*, Bacillaceae (e.g., *Bacillus* anthrasis), *Bacteroides* (e.g., *Bacteroides fragilis*), Blastomycosis, *Bordetella, Borrelia* (e.g., *Borrelia burgdorferi*), *Brucella, Candidia, Campylobacter, Chlamydia, Coccidioides, Corynebacterium* (e.g., *Corynebacterium* diptheriae), *Cryptococcus*, Dermatocycoses, *E. coli* (e.g., Enterotoxigenic *E. coli* and Enterohemorrhagic *E. coli*), *Enterobacter* (e.g. *Enterobacter aerogenes*), Enterobacteriaceae (*Klebsiella, Salmonella* (e.g., *Salmonella typhi, Salmonella enteritidis, Serratia, Yersinia, Shigella*), Erysipelothrix, *Haemophilus* (e.g., *Haemophilus* influenza type B), *Helicobacter, Legionella* (e.g., *Legionella pneumophila*), *Leptospira, Listeria* (e.g., *Listeria monocytogenes*), *Mycoplasma, Mycobacterium* (e.g., *Mycobacterium leprae* and *Mycobacterium tuberculosis*), *Vibrio* (e.g., *Vibrio cholerae*), Pasteurellacea, *Proteus, Pseudomonas* (e.g., *Pseudomonas aeruginosa*), Rickettsiaceae, Spirochetes (e.g., *Treponema* spp., *Leptospira* spp., *Borrelia* spp.), *Shigella* spp., Meningiococcus, Pneumococcus and *Streptococcus* (e.g., *Streptococcus pneumoniae* and Groups A, B, and C Streptococci), Ureaplasmas, *Treponema pollidum*, and the like; *Staphylococcus aureus, Plasmodium* sp. (*Pl. falciparum, Pl. vivax*, etc.), *Aspergillus* sp., *Candida albicans, Pasteurella haemolytica, Corynebacterium* diptheriae toxoid, Meningococcal polysaccharide, *Bordetella pertusis, Streptococcus pneumoniae* (pneumococcus) polysaccharide, *Clostridium tetani* toxoid, *Mycobacterium bovis*, killed cells of *Salmonella typhi, Cryptococcus neoformans*, and *Aspergillus*.

The antigens may also be derived from parasitic malaria, leishmaniasis, trypanosomiasis, toxoplasmosis, schistosomiasis, filariasis malaria, Amebiasis, Babesiosis, Coccidiosis, Cryptosporidiosis, Dientamoebiasis, Dourine, Ectoparasitic, Giardias, Helminthiasis, Theileriasis, *Trichomonas* and Sporozoans (e.g., *Plasmodium virax, Plasmodium fakiparium, Plasmodium malariae* and *Plasmodium ovale*). These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), malaria, pregnancy complications, and toxoplasmosis.

Tumor-associated antigens suitable for use in compositions described herein include both mutated and non-mutated molecules which may be indicative of single tumor type, shared among several types of tumors, and/or exclusively expressed or overexpressed in tumor cells in comparison with normal cells. In addition to proteins and glycoproteins, tumor-specific patterns of expression of carbohydrates, gangliosides, glycolipids and mucins have also been documented. Exemplary tumor-associated antigens for use in the subject cancer vaccines include protein products of oncogenes, tumor suppressor genes and other genes with mutations or rearrangements unique to tumor cells, reactivated embryonic gene products, oncofetal antigens, tissue-specific (but not tumor-specific) differentiation antigens, growth factor receptors, cell surface carbohydrate residues, foreign viral proteins and a number of other self proteins. Specific embodiments of tumor-associated antigens include, e.g., mutated antigens such as the protein products of the Ras p21 protooncogenes, tumor suppressor p53 and HER-2/neu and BCR-ab1 oncogenes, as well as CDK4, MUM1, Caspase 8, and Beta catenin; overexpressed antigens such as galectin 4, galectin 9, carbonic anhydrase, Aldolase A, PRAME, Her2/neu, ErbB-2 and KSA, oncofetal antigens such as alpha fetoprotein (AFP), human chorionic gonadotropin (hCG); self antigens such as carcinoembryonic antigen (CEA) and melanocyte differentiation antigens such as Mart 1/Melan A, gp100, gp75, Tyrosinase, TRP1 and TRP2; prostate associated antigens such as PSA, PAP, PSMA, PSM-P1 and PSM-P2; reactivated embryonic gene products such as MAGE 1, MAGE 3, MAGE 4, GAGE 1, GAGE 2, BAGE, RAGE, and other cancer testis antigens such as NY-ESO1, SSX2 and SCP1; mucins such as Muc-1 and Muc-2; gangliosides such as GM2, GD2 and GD3, neutral glycolipids and glycoproteins such as Lewis (y) and globo-H; and glycoproteins such as Tn, Thompson-Freidenreich antigen (TF) and sTn. Also included as tumor-associated antigens herein are whole cell and tumor cell lysates as well as immunogenic portions thereof, as well as immunoglobulin idiotypes expressed on monoclonal proliferations of B lymphocytes for use against B cell lymphomas. Tumor-associated antigens and their respective tumor cell targets include, e.g., cytokeratins, particularly cytokeratin 8, 18 and 19, as antigens for carcinoma. Epithelial membrane antigen (EMA), EphA1, EphA2, EphA3, EphA4, EphA5, EphA6, EphA7, EphA8, EphA10, EphB1, EphB2, EphB3, EphB4, EphB6, human embryonic antigen (HEA-125), human milk fat globules, MBr1, MBr8, Ber-EP4, 17-1A, C26 and T16 are also known carcinoma antigens. Desmin and muscle-specific actin are antigens of myogenic sarcomas. Placental alkaline phosphatase, beta-human chorionic gonadotropin, and alpha-fetoprotein are antigens of trophoblastic and germ cell tumors. Prostate specific antigen is an antigen of prostatic carcinomas, carcinoembryonic antigen of colon adenocarcinomas. HMB-45 is an antigen of melanomas. In cervical cancer, useful antigens could be encoded by human papilloma virus. Chromagranin-A and synaptophysin are antigens of neuroendocrine and neuroectodermal tumors. Of particular interest are aggressive tumors that form solid tumor masses having necrotic areas. The lysis of such necrotic cells is a rich source of antigens for antigen-presenting cells, and thus the subject therapy may find advantageous use in conjunction with conventional chemotherapy and/or radiation therapy. The antigens can be derived from any tumor or malignant cell line.

Antigens may also be derived from common allergens that cause allergies. Allergens include organic or inorganic materials derived from a variety of man-made or natural sources such as plant materials, metals, ingredients in cosmetics or detergents, latexes, or the like. Classes of suitable allergens for use in the compositions and methods described herein can include, but are not limited to, pollens, animal dander, grasses, molds, dusts, antibiotics, stinging insect venoms, and a variety of environmental (including chemicals and metals) drug and food allergens. Common tree allergens include pollens from cottonwood, popular, ash, birch, maple, oak, elm, hickory, and pecan trees; common plant allergens include those from rye, ragweed, English plantain, sorrel-dock and pigweed; plant contact allergens include those from poison oak, poison ivy and nettles; common grass allergens include Timothy, Johnson, Bermuda, fescue and bluegrass allergens; common allergens can also be obtained from molds or fungi such as *Alternaria, Fusarium, Hormodendrum, Aspergillus, Micropolyspora, Mucor* and thermophilic actinomycetes; penicillin and tetracycline are common antibiotic allergens; epidermal allergens can be obtained from house or organic dusts (typically fungal in origin), from insects such as house mites (dermalphagoides pterosinyssis), or from animal sources such as feathers, and cat and dog dander; common food allergens include milk and cheese (diary), egg, wheat, nut (e.g., peanut), seafood (e.g., shellfish), pea, bean and gluten allergens; common environmental allergens include metals (nickel and gold), chemicals (formaldehyde, trinitrophenol and turpentine), Latex, rubber, fiber (cotton or wool), burlap, hair dye, cosmetic, detergent and perfume allergens; common drug allergens include local anesthetic and salicylate allergens; antibiotic allergens include penicillin and sulfonamide allergens; and common insect allergens include bee, wasp and ant venom, and cockroach calyx allergens. Particularly well characterized allergens include, but are not limited to, the major and cryptic epitopes of the Der pl allergen (Hoyne et al. (1994) Immunology 83, 190-195), bee venom phospholipase A2 (PLA) (Akdis et al. (1996) J. Clin. Invest. 98, 1676-1683), birch pollen allergen Bet v 1 (Bauer et al. (1997) Clin. Exp. Immunol. 107, 536-541), and the multi-epitopic recombinant grass allergen rKBG8.3 (Cao et al. (1997) Immunology 90, 46-51). These and other suitable allergens are commercially available and/or can be readily prepared as extracts following known techniques.

The antigen may be in the form of purified or partially purified antigen and can be derived from any of the above antigens, an antigenic peptide, proteins that are known and available in the art, and others that can identified using conventional techniques. The antigens will typically be in the form in which their toxic or virulent properties have been reduced or destroyed and which when introduced into a suitable, will either induce and immune response against the specific microorganisms, extract, or products of microorganisms used in the preparation of the antigen, or, in the case of allergens, they will aid in alleviating the symptoms of the allergy due to the specific allergen. The antigens can be used either singly or in combination; for example, multiple bacterial antigens, multiple viral antigens, multiple bacterial antigens, multiple parasitic antigens, multiple bacterial, viral toxoids, multiple tumor antigens, multiple allergens or combinations of any of the foregoing products can be combined with adjuvant compositions to create a polyvalent antigenic composition and/or a vaccine. In the compositions described herein, the antigen may be antigen entrapped in, adsorbed to, or in an admixture with the vesicle component of the composition.

In one embodiment, suitable antigens for use with the compositions described herein include antigens which are poorly immunogenic, for example malaria antigens, dengue antigens and HIV antigens, or antigens intended to confer immunity against pandemic diseases, for example influenza antigens.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (e.g., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

The term "expression" as used herein is defined as the transcription and/or translation of a particular nucleotide sequence driven by its promoter.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, typically, a human.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The terms "therapeutically effective amount", "effective amount" or "sufficient amount" mean a quantity sufficient, when administered to a subject, including a mammal, for example a human, to achieve a desired result, for example an amount effective to cause a protective immune response. Effective amounts of the compounds described herein may vary according to factors such as the immunogen, age, sex, and weight of the subject.

Dosage or treatment regimes may be adjusted to provide the optimum therapeutic response, as is understood by a skilled person. For example, administration of a therapeutically effective amount of the fusion proteins described herein is, in aspects, sufficient to increase immunity against a pathogen, such as *Plasmodium*. In other aspects, administration of a therapeutically effective amount of the fusion proteins described herein is sufficient to treat a disease or condition, such as cancer, HIV, malaria, or an autoimmune disease. In still other aspects, administration of a therapeutically effective amount of the fusion proteins described herein is sufficient to act as an adjuvant to increase effectiveness of a vaccine.

Moreover, a treatment regime of a subject with a therapeutically effective amount may consist of a single administration, or alternatively comprise a series of applications. The length of the treatment period depends on a variety of factors, such as the immunogen, the age of the subject, the concentration of the agent, the responsiveness of the patient to the agent, or a combination thereof. It will also be appreciated that the effective dosage of the agent used for the treatment may increase or decrease over the course of a particular. treatment regime. Changes in dosage may result and become apparent by standard diagnostic assays known in the art. The fusion proteins described herein may, in aspects, be administered before, during or after treatment with conventional therapies for the disease or disorder in question, such as malaria, HIV or cancer. For example, the fusion proteins described herein may find particular use in combination with immunotherapies for treating cancer.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses.

Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

The term "subject" as used herein refers to any member of the animal kingdom, typically a mammal. The term "mammal" refers to any animal classified as a mammal, including humans, other higher primates, domestic and farm animals, and zoo, sports, or pet animals, such as dogs, cats, cattle, horses, sheep, pigs, goats, rabbits, etc. Typically, the mammal is human.

Administration "in combination with" one or more further therapeutic agents includes simultaneous (concurrent) and consecutive administration in any order.

The term "pharmaceutically acceptable" means that the compound or combination of compounds is compatible with the remaining ingredients of a formulation for pharmaceutical use, and that it is generally safe for administering to humans according to established governmental standards, including those promulgated by the United States Food and Drug Administration.

The term "pharmaceutically acceptable carrier" includes, but is not limited to solvents, dispersion media, coatings, antibacterial agents, antifungal agents, isotonic and/or absorption delaying agents and the like. The use of pharmaceutically acceptable carriers is well known.

The term "adjuvant" refers to a compound or mixture that is present in a vaccine and enhances the immune response to an antigen present in the vaccine. For example, an adjuvant may enhance the immune response to a polypeptide present in a vaccine as contemplated herein, or to an immunogenic fragment or variant thereof as contemplated herein. An adjuvant can serve as a tissue depot that slowly releases the antigen and also as a lymphoid system activator that non-specifically enhances the immune response. Examples of adjuvants which may be employed include MPL-TDM adjuvant (monophosphoryl Lipid A/synthetic trehalose dicorynomycolate, e.g., available from GSK Biologics). Another suitable adjuvant is the immunostimulatory adjuvant AS021/AS02 (GSK). These immunostimulatory adjuvants are formulated to give a strong T cell response and include QS-21, a saponin from Quillay saponaria, the TL4 ligand, a monophosphoryl lipid A, together in a lipid or liposomal carrier. Other adjuvants include, but are not limited to, nonionic block co-polymer adjuvants (e.g., CRL 1005), aluminum phosphates (e.g., AIPO.sub.4), R-848 (a Th1-like adjuvant), imiquimod, PAM3CYS, poly(I:C), loxoribine, BCG (bacille Calmette-Guerin) and *Corynebacterium parvum*, CpG oligodeoxynucleotides (ODN), cholera toxin derived antigens (e.g., CTA 1-DD), lipopolysaccharide adjuvants, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions in water (e.g., MF59 available from Novartis Vaccines or Montanide ISA 720), keyhole limpet hemocyanins, and dinitrophenol.

"Variants" are biologically active fusion proteins, antibodies, or fragments thereof having an amino acid sequence that differs from a comparator sequence by virtue of an insertion, deletion, modification and/or substitution of one or more amino acid residues within the comparative sequence. Variants generally have less than 100% sequence identity with the comparative sequence. Ordinarily, however, a biologically active variant will have an amino acid sequence with at least about 70% amino acid sequence identity with the comparative sequence, such as at least about 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity. The variants include peptide fragments of at least 10 amino acids that retain some level of the biological activity of the comparator sequence. Variants also include polypeptides wherein one or more amino acid residues are added at the N- or C-terminus of, or within, the comparative sequence. Variants also include polypeptides where a number of amino acid residues are deleted and optionally substituted by one or more amino acid residues. Variants also may be covalently modified, for example by substitution with a moiety other than a naturally occurring amino acid or by modifying an amino acid residue to produce a non-naturally occurring amino acid.

"Percent amino acid sequence identity" is defined herein as the percentage of amino acid residues in the candidate sequence that are identical with the residues in the sequence of interest, such as the polypeptides of the invention, after aligning the sequences and introducing gaps, if necessary, to achieve the maximum percent sequence identity, and not considering any conservative substitutions as part of the sequence identity. None of N-terminal, C-terminal, or internal extensions, deletions or insertions into the candidate sequence shall be construed as affecting sequence identity or homology. Methods and computer programs for the alignment are well known in the art, such as "BLAST".

"Active" or "activity" for the purposes herein refers to a biological and/or an immunological activity of the fusion proteins described herein, wherein "biological" activity refers to a biological function (either inhibitory or stimulatory) caused by the fusion proteins. The fusion proteins described herein may include modifications. Such modifications include, but are not limited to, conjugation to an effector molecule such as an anti-malaria agent or an adjuvant. Modifications further include, but are not limited to conjugation to detectable reporter moieties. Modifications that extend half-life (e.g., pegylation) are also included. Proteins and non-protein agents may be conjugated to the fusion proteins by methods that are known in the art. Conjugation methods include direct linkage, linkage via covalently attached linkers, and specific binding pair members (e.g., avidin-biotin). Such methods include, for example, that described by Greenfield et al., Cancer Research 50, 6600-6607 (1990), which is incorporated by reference herein and those described by Amon et al., Adv. Exp. Med. Biol. 303, 79-90 (1991) and by Kiseleva et al, Mol. Biol. (USSR) 25, 508-514 (1991), both of which are incorporated by reference herein.

Fusion Proteins

Described herein are fusion proteins. The fusion proteins comprise a nanocage monomer and an antibody or fragment thereof linked to the nanocage monomer, the antibody or fragment thereof comprising an antigen-binding epitope. A plurality of the fusion proteins self-assemble to form a nanocage in which a plurality of the antibodies or fragments thereof decorate the exterior surface of the nanocage, whereby the antigen-binding epitope is exposed for interacting with an antigen.

In other aspects, the fusion proteins comprise a nanocage monomer and an antibody or fragment thereof linked to the nanocage monomer, the antibody or fragment thereof comprising a Fc portion of an antibody or fragment thereof. A plurality of the fusion proteins self-assemble to form a nanocage in which a plurality of the antibodies or fragments thereof decorate the exterior surface of the nanocage, whereby Fc portion of an antibody or fragment thereof is exposed for interacting with a Fc receptor.

In typical aspects, the nanocage comprises from about 3 to about 100 nanocage monomers, such as from about 3, 4, 5, 6, 7, 8, 9, 10, 12, 14, 16, 18, 20, 22, 24, 26, 28, 30, 32, 34, 36, 38, 40, 42, 44, 46, 48, 50, 52, 55, 56, 58, 60, 62, 64, 66, 68, 70, 72, 74, 76, 78, 80, 82, 84, 86, 88, 90, 92, 94, 96, or 98 to about 4, 5, 6, 7, 8, 9, 10, 12, 14, 16, 18, 20, 22, 24, 26, 28, 30, 32, 34, 36, 38, 40, 42, 44, 46, 48, 50, 52, 55, 56, 58, 60, 62, 64, 66, 68, 70, 72, 74, 76, 78, 80, 82, 84, 86, 88, 90, 92, 94, 96, 98, or 100 nanocage monomers, such as 24 or 60 monomers. The nanocage monomer may be any known nanocage monomer, natural, synthetic, or partly synthetic and is, in aspects, selected from ferritin, encapsulin, SOR, lumazine synthase, pyruvate dehydrogenase, carboxysome, vault proteins, GroEL, heat shock protein, E2P, MS2 coat protein, fragments thereof, and variants thereof. FIGS. 1A and 1B show images of self-assembling nanocages.

In certain aspects, the fusion proteins described herein comprise a linker between the nanocage monomer and the antibody or fragment thereof. This linker allows both the nanocage monomer and the antibody or fragment thereof to adopt favourable conformations for self-assembly and antibody function, once the protein is expressed. The linker may be flexible or rigid.

The linker is generally long enough to impart some flexibility to the fusion protein, although it will be understood that linker length will vary depending upon the nanocage monomer and antibody sequences and the three-dimensional conformation of the fusion protein. Thus, the linker is typically from about 1 to about 30 amino acid residues, such as from about 1, 2, 3, 4, 5, 6, 7, 8, 9, 10, 11, 12, 13, 14, 15, 16, 17, 18, 19, 20, 21, 22, 23, 24, 25, 26, 27, 28, or 29 to about 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid residues, such as from about 8 to about 16 amino acid residues, such as 8, 10, or 12 amino acid residues.

The linker may be of any amino acid sequence that does not interfere with the binding of the antigen to its antigen binding site on the antibody. In one typical example, the linker comprises a GGS repeat and, more typically, the linker comprises about 2, 3, 4, 5, or 6 GGS repeats, such as about 4 GGS repeats.

Typically, the antibody comprises a heavy chain and/or light chain of a Fab fragment, although it will be understood that any antibody or fragment thereof, such as one of those listed above, may be used in the fusion proteins described herein. In other typical aspects, the antibody or fragment thereof comprises an scFv or an scFc.

In certain aspects, the fusion protein may further comprise an antigen. Such aspects are described explicitly in U.S. Application No. 62/541,211, which is incorporated herein by reference in its entirety. Briefly, in such aspects, the antigen has at least a first and a second antibody-binding epitope; and an antibody or fragment thereof that is specific for at least the first antigen epitope. Binding of the antibody or fragment thereof to the first antigen epitope presents the second antigen epitope for binding to an antigen-binding moiety and/or the first antibody-binding epitope binds to the antibody or fragment thereof and wherein said binding presents said second antibody-binding epitope in the context of the antibody or fragment thereof.

In aspects, the antigen typically comprises a repeat domain. This facilitates inclusion of two identical antibody binding epitopes in a single entity. Of course, the antigen, as has been described above, may have different antibody binding epitopes, in which case a repeat domain would not be appropriate. In related aspects, the antibody is specific for a repeat domain.

In typical aspects, the antigen is a malaria antigen, such as a fragment of the malaria CSP protein. More typically, the antigen is a fragment of the NANP repeat domain of the malaria CSP protein and comprises 5.5 NANP repeats. In typical aspects, the antigen is NPNANPNANPNANPNANPNANP (SEQ ID NO: 1). In related aspects, the antibody is specific for a malaria antigen, such as the malaria CSP protein and, more typically, the NANP repeat domain of the malaria CSP protein.

It will be understood that the malaria CSP protein may have other repeating amino acids besides or in addition to NANP, including NPDP, NVDP, and NANA. These, repeated alone or in any combination with or without NANP, may form the antigen or part of the antigen and, for the sake of clarity, are encompassed by the phrase "NANP repeat domain" even if NANP is not present. The unique location of the NPDP motif at the junction between the N-terminal domain and the central repeat region is conserved in almost all Pf isolates (>99.8%) (Kisalu et al., 2018). In contrast, although an NANP-NVDP alternating sequence is generally located immediately after the NPDP motif, NANP motifs can be repeated >40 times, and the length can differ widely between Pf field isolates. As such, repeat-targeting mAbs have been shown to bind many copies of their epitope even within a single PfCSP molecule. mAbs MGG4 and CIS43 bind promiscuously to NPDP, NVDP, and NANP yet also demonstrate distinctive preferences for specific repeating motifs. Importantly, the described mAbs have the ability to engage the NPDP motif (termed the junctional epitope,

KQPADGNPDPNANPNVDPN), which may confer increased potency to inhibit Pf sporozoites. The paratopes of mAbs MGG4 and CIS43 have the ability to accommodate the interchangeable nature of certain amino acids in the repeating motifs (NPDP versus NVDP versus NANP).

Typically, the antibody or fragment thereof comprises a sequence having at least 90% sequence identity to the sequence:

QVQLVESGGGVVQPGRSLRLSCAASGFTFSNYGMHWVRQAPGKGLEWVAV

IWDGSKKYYADSVKGRFTISRDNSKNTLYLQMNSLRAEDTAVYYCARVRD

SSDYYGDAFDIWGQGTMVTVSS or a fragment thereof, such as sequence having at least 91%, 92%, 93%, 94%, 95%, 96%, 97%, 98%, or 99% sequence identity, such as a sequence comprising or consisting of 100% sequence identity to this sequence.

In other aspects, the antibody or fragment thereof is an anti-CD22 or anti-CD19 antibody, such as Epratuzumab or Denintuzumab. In certain aspects, an antigen may be co-displayed on the surface of the nanocages, either as a separate subunit fusion protein or bound by any other known method to the surface of the nanocages. By co-displaying an antigen and an anti-CD19 antibody or fragment thereof, an adjuvant effect specifically linked to the antigen is provided. It is specifically contemplated that the antigen being co-displayed with anti-CD19 may be either bound to the nanoparticle surface directly or indirectly and may be displayed in the context of an antibody or fragment thereof as described above.

In other aspects, the antibody or fragment thereof may be directed to any antigen, such as those listed above. Typically, the antigen is derived from a cancer or an infectious agent such as hepatitis A, B, C, HIV, mycobacteria, malaria pathogens, SARS pathogens, herpesvirus, influenzavirus, poliovirus or from bacterial pathogens such as *chlamydia* and mycobacteria, or from autoreactive B cells or any T cells for co-recruitment and cytotoxic killing.

Generally, the fusion protein described herein is associated with a Fab light chain and/or heavy chain, which may be produced separately or contiguously with the fusion protein.

The fusion proteins described herein may alternatively find use as therapeutics or diagnostic agents. Thus, the antibody or fragment thereof in aspects may be specific for a tumour antigen or an autoantigen, for example.

A substantially identical sequence may comprise one or more conservative amino acid mutations. It is known in the art that one or more conservative amino acid mutations to a reference sequence may yield a mutant peptide with no substantial change in physiological, chemical, or functional properties compared to the reference sequence; in such a case, the reference and mutant sequences would be considered "substantially identical" polypeptides. Conservative amino acid mutation may include addition, deletion, or substitution of an amino acid; a conservative amino acid substitution is defined herein as the substitution of an amino acid residue for another amino acid residue with similar chemical properties (e.g. size, charge, or polarity).

In a non-limiting example, a conservative mutation may be an amino acid substitution. Such a conservative amino acid substitution may substitute a basic, neutral, hydrophobic, or acidic amino acid for another of the same group. By the term "basic amino acid" it is meant hydrophilic amino acids having a side chain pK value of greater than 7, which are typically positively charged at physiological pH. Basic amino acids include histidine (His or H), arginine (Arg or R), and lysine (Lys or K). By the term "neutral amino acid" (also "polar amino acid"), it is meant hydrophilic amino acids having a side chain that is uncharged at physiological pH, but which has at least one bond in which the pair of electrons shared in common by two atoms is held more closely by one of the atoms. Polar amino acids include serine (Ser or S), threonine (Thr or T), cysteine (Cys or C), tyrosine (Tyr or Y), asparagine (Asn or N), and glutamine (Gln or Q). The term "hydrophobic amino acid" (also "non-polar amino acid") is meant to include amino acids exhibiting a hydrophobicity of greater than zero according to the normalized consensus hydrophobicity scale of Eisenberg (1984). Hydrophobic amino acids include proline (Pro or P), isoleucine (Ile or I), phenylalanine (Phe or F), valine (Val or V), leucine (Leu or L), tryptophan (Trp or W), methionine (Met or M), alanine (Ala or A), and glycine (Gly or G).

"Acidic amino acid" refers to hydrophilic amino acids having a side chain pK value of less than 7, which are typically negatively charged at physiological pH. Acidic amino acids include glutamate (Glu or E), and aspartate (Asp or D).

Sequence identity is used to evaluate the similarity of two sequences; it is determined by calculating the percent of residues that are the same when the two sequences are aligned for maximum correspondence between residue positions. Any known method may be used to calculate sequence identity; for example, computer software is available to calculate sequence identity. Without wishing to be limiting, sequence identity can be calculated by software such as NCBI BLAST2 service maintained by the Swiss Institute of Bioinformatics (and as found at ca.expasy.org/tools/blast/), BLAST-P, Blast-N, or FASTA-N, or any other appropriate software that is known in the art.

The substantially identical sequences of the present invention may be at least 85% identical; in another example, the substantially identical sequences may be at least 70, 75, 80, 85, 90, 95, 96, 97, 98, 99, or 100% (or any percentage there between) identical at the amino acid level to sequences described herein. In specific aspects, the substantially identical sequences retain the activity and specificity of the reference sequence. In a non-limiting embodiment, the difference in sequence identity may be due to conservative amino acid mutation(s).

The polypeptides or fusion proteins of the present invention may comprise additional sequences to aid in their expression, detection or purification. Any such sequences or tags known to those of skill in the art may be used. For example, and without wishing to be limiting, the fusion proteins may comprise a targeting or signal sequence (for example, but not limited to ompA), a detection tag, exemplary tag cassettes include Strep tag, or any variant thereof; see, e.g., U.S. Pat. No. 7,981,632, His tag, Flag tag having the sequence motif DYKDDDDK (SEQ ID NO: 4), Xpress tag, Avi tag, Calmodulin tag, Polyglutamate tag, HA tag, Myc tag, Nus tag, S tag, SBP tag, Softag 1, Softag 3, V5 tag, CREB-binding protein (CBP), glutathione S-transferase (GST), maltose binding protein (MBP), green fluorescent protein (GFP), Thioredoxin tag, or any combination thereof; a purification tag (for example, but not limited to a Hiss or His6), or a combination thereof.

In another example, the additional sequence may be a biotin recognition site such as that described by Cronan et al in WO 95/04069 or Voges et al in WO/2004/076670. As is also known to those of skill in the art, linker sequences may be used in conjunction with the additional sequences or tags.

More specifically, a tag cassette may comprises an extracellular component that can specifically bind to an antibody with high affinity or avidity. Within a single chain fusion protein structure, a tag cassette may be located (a) immediately amino-terminal to a connector region, (b) interposed between and connecting linker modules, (c) immediately carboxy-terminal to a binding domain, (d) interposed between and connecting a binding domain (e.g., scFv) to an effector domain, (e) interposed between and connecting subunits of a binding domain, or (f) at the amino-terminus of a single chain fusion protein. In certain embodiments, one or more junction amino acids may be disposed between and connecting a tag cassette with a hydrophobic portion, or disposed between and connecting a tag cassette with a connector region, or disposed between and connecting a tag cassette with a linker module, or disposed between and connecting a tag cassette with a binding domain.

Also encompassed herein are isolated or purified fusion proteins, polypeptides, or fragments thereof immobilized onto a surface using various methodologies; for example, and without wishing to be limiting, the polypeptides may be linked or coupled to the surface via His-tag coupling, biotin binding, covalent binding, adsorption, and the like. The solid surface may be any suitable surface, for example, but not limited to the well surface of a microtiter plate, channels of surface plasmon resonance (SPR) sensorchips, membranes, beads (such as magnetic-based or sepharose-based beads or other chromatography resin), glass, a film, or any other useful surface.

In other aspects, the fusion proteins may be linked to a cargo molecule; the fusion proteins may deliver the cargo molecule to a desired site and may be linked to the cargo molecule using any method known in the art (recombinant technology, chemical conjugation, chelation, etc.). The cargo molecule may be any type of molecule, such as a therapeutic or diagnostic agent. For example, and without wishing to be limiting in any manner, the therapeutic agent may be a radioisotope, which may be used for radioimmunotherapy; a toxin, such as an immunotoxin; a cytokine, such as an immunocytokine; a cytotoxin; an apoptosis inducer; an enzyme; an anti-cancer antibody for immunotherapy; or any other suitable therapeutic molecule known in the art. In the alternative, a diagnostic agent may include, but is by no means limited to a radioisotope, a paramagnetic label such as gadolinium or iron oxide, a fluorophore, a Near Infra-Red (NIR) fluorochrome or dye (such as Cy3, Cy5.5, Alexa680, Dylight680, or Dylight800), an affinity label (for example biotin, avidin, etc), fused to a detectable protein-based molecule, or any other suitable agent that may be detected by imaging methods. In a specific, non-limiting example, the fusion protein may be linked to a fluorescent agent such as FITC or may genetically be fused to the Enhanced Green Fluorescent Protein (EGFP).

In some aspects, the cargo molecule is a protein and is fused to the fusion protein such that the cargo molecule is contained in the nanocage internally. In other aspects, the cargo molecule is not fused to the fusion protein and is contained in the nanocage internally. The cargo molecule is typically a protein, a small molecule, a radioisotope, or a magnetic particle.

The fusion proteins described herein specifically bind to their targets. Antibody specificity, which refers to selective recognition of an antibody for a particular epitope of an antigen, of the antibodies or fragments described herein can be determined based on affinity and/or avidity. Affinity, represented by the equilibrium constant for the dissociation of an antigen with an antibody ($K_D$), measures the binding strength between an antigenic determinant (epitope) and an antibody binding site. Avidity is the measure of the strength of binding between an antibody with its antigen. Antibodies typically bind with a $K_D$ of $10^{-5}$ to $10^{-11}$ M. Any $K_D$ greater than $10^{-4}$ M is generally considered to indicate non-specific binding. The lesser the value of the $K_D$, the stronger the binding strength between an antigenic determinant and the antibody binding site. In aspects, the antibodies described herein have a $K_D$ of less than $10^{-4}$ M, $10^{-5}$ M, $10^{-6}$ M, $10^{-7}$ M, $10^{-8}$ M, or $10^{-9}$ M.

Also described herein are nanocages comprising at least one fusion protein described herein. It will be understood that the nanocages may self-assemble from multiple identical fusion proteins, from multiple different fusion proteins (and therefore be multivalent), from a combination of fusion proteins and wild-type proteins, and any combination thereof. For example, the nanocages may be decorated with at least one of the fusion proteins described herein in combination with at least one anti-cancer antibody for immunotherapy. In typical aspects, from about 20% to about 80% of the nanocage monomers comprise the fusion protein described herein.

Also described herein are nucleic acid molecules encoding the fusion proteins and polypeptides described herein, as well as vectors comprising the nucleic acid molecules and host cells comprising the vectors.

Polynucleotides encoding the fusion proteins described herein include polynucleotides with nucleic acid sequences that are substantially the same as the nucleic acid sequences of the polynucleotides of the present invention. "Substantially the same" nucleic acid sequence is defined herein as a sequence with at least 70%, at least 75%, at least 80%, at least 85%, at least 90%, at least 91%, at least 92%, at least 93%, at least 94%, at least 95% identity to another nucleic acid sequence when the two sequences are optimally aligned (with appropriate nucleotide insertions or deletions) and compared to determine exact matches of nucleotides between the two sequences.

Suitable sources of DNAs that encode fragments of antibodies include any cell, such as hybridomas and spleen cells, that express the full-length antibody. The fragments may be used by themselves as antibody equivalents, or may be recombined into equivalents, as described above. The DNA deletions and recombinations described in this section may be carried out by known methods, such as those described in the published patent applications listed above in the section entitled "Functional Equivalents of Antibodies" and/or other standard recombinant DNA techniques, such as those described below. Another source of DNAs are single chain antibodies produced from a phage display library, as is known in the art.

Additionally, expression vectors are provided containing the polynucleotide sequences previously described operably linked to an expression sequence, a promoter and an enhancer sequence. A variety of expression vectors for the efficient synthesis of antibody polypeptide in prokaryotic, such as bacteria and eukaryotic systems, including but not limited to yeast and mammalian cell culture systems have been developed. The vectors of the present invention can comprise segments of chromosomal, non-chromosomal and synthetic DNA sequences.

Any suitable expression vector can be used. For example, prokaryotic cloning vectors include plasmids from E. coli, such as colEI, pCRI, pBR322, pMB9, pUC, pKSM, and RP4. Prokaryotic vectors also include derivatives of phage DNA such as MI3 and other filamentous single-stranded DNA phages. An example of a vector useful in yeast is the 2p plasmid. Suitable vectors for expression in mammalian cells include well-known derivatives of SV-40, adenovirus, retrovirus-derived DNA sequences and shuttle vectors derived from combination of functional mammalian vectors, such as those described above, and functional plasmids and phage DNA.

Additional eukaryotic expression vectors are known in the art (e.g., P J. Southern & P. Berg, J. Mol. Appl. Genet, 1:327-341 (1982); Subramani et al, Mol. Cell. Biol, 1:854-864 (1981); Kaufinann & Sharp, "Amplification And Expression of Sequences Cotransfected with a Modular Dihydrofolate Reductase Complementary DNA Gene," J. Mol. Biol, 159:601-621 (1982); Kaufhiann & Sharp, Mol. Cell. Biol, 159:601-664 (1982); Scahill et al., "Expression And Characterization Of The Product Of A Human Immune Interferon DNA Gene In Chinese Hamster Ovary Cells," Proc. Nat'l Acad. Sci USA, 80:4654-4659 (1983); Urlaub & Chasin, Proc. Nat'l Acad. Sci USA, 77:4216-4220, (1980), all of which are incorporated by reference herein).

The expression vectors typically contain at least one expression control sequence that is operatively linked to the DNA sequence or fragment to be expressed. The control sequence is inserted in the vector in order to control and to regulate the expression of the cloned DNA sequence. Examples of useful expression control sequences are the lac system, the trp system, the tac system, the trc system, major operator and promoter regions of phage lambda, the control region of fd coat protein, the glycolytic promoters of yeast, e.g., the promoter for 3-phosphoglycerate kinase, the promoters of yeast acid phosphatase, e.g., Pho5, the promoters of the yeast alpha-mating factors, and promoters derived from polyoma, adenovirus, retrovirus, and simian virus, e.g., the early and late promoters or SV40, and other sequences known to control the expression of genes of prokaryotic or eukaryotic cells and their viruses or combinations thereof.

Also described herein are recombinant host cells containing the expression vectors previously described. The fusion proteins described herein can be expressed in cell lines other than in hybridomas. Nucleic acids, which comprise a sequence encoding a polypeptide according to the invention, can be used for transformation of a suitable mammalian host cell.

Cell lines of particular preference are selected based on high level of expression, constitutive expression of protein of interest and minimal contamination from host proteins. Mammalian cell lines available as hosts for expression are well known in the art and include many immortalized cell lines, such as but not limited to, Chinese Hamster Ovary (CHO) cells, Baby Hamster Kidney (BHK) cells and many others. Suitable additional eukaryotic cells include yeast and other fungi. Useful prokaryotic hosts include, for example, *E. coli*, such as *E. coli* SG-936, *E. coli* HB 101, *E. coli* W3110, *E. coli* X1776, *E. coli* X2282, *E. coli* DHI, and *E. coli* MRC1, *Pseudomonas, Bacillus*, such as *Bacillus subtilis*, and *Streptomyces*.

These present recombinant host cells can be used to produce fusion proteins by culturing the cells under conditions permitting expression of the polypeptide and purifying the polypeptide from the host cell or medium surrounding the host cell. Targeting of the expressed polypeptide for secretion in the recombinant host cells can be facilitated by inserting a signal or secretory leader peptide-encoding sequence (See, Shokri et al, (2003) Appl Microbiol Biotechnol. 60 (6): 654-664, Nielsen et al, Prot. Eng., 10:1-6 (1997); von Heinje et al., Nucl. Acids Res., 14:4683-4690 (1986), all of which are incorporated by reference herein) at the 5' end of the antibody-encoding gene of interest. These secretory leader peptide elements can be derived from either prokaryotic or eukaryotic sequences. Accordingly suitably, secretory leader peptides are used, being amino acids joined to the N-terminal end of a polypeptide to direct movement of the polypeptide out of the host cell cytosol and secretion into the medium.

The fusion proteins described herein can be fused to additional amino acid residues. Such amino acid residues can be a peptide tag to facilitate isolation, for example. Other amino acid residues for homing of the antibodies to specific organs or tissues are also contemplated.

It will be understood that an Fab-nanocage can be generated by co-transfection of HC-ferritin and LC. Alternatively, single-chain Fab-ferritin nanocages can be used that only require transfection of one plasmid, as shown in FIG. 1C. This can be done with linkers of different lengths between the LC and HC for example 60 or 70 amino acids. When single-chain Fabs are used, it can be ensured that the heavy chain and light chain are paired. Tags (e.g. Flag, HA, myc, His6x, Strep, etc.) can also be added at the N terminus of the construct or within the linker for ease of purification as described above. Further, a tag system can be used to make sure many different Fabs are present on the same nanoparticle using serial/additive affinity chromatography steps when different Fab-nanoparticle plasmids are co-transfected. This provides multi-specificity to the nanoparticles. Protease sites (e.g. TEV, 3C, etc.) can be inserted to cleave linkers and tags after expression and/or purification, if desired. An example of such a construct is for anti-HIV broadly neutralizing Fab 10E8:

```
YELTQETGVSVALGRTVTITCRGDSLRSHYASWYQKKPGQAPILLFYGKN

NRPSGVPDRFSGSASGNRASLTISGAQAEDDAEYYCSSRDKSGSRLSVFG

GGTKLTVLSQPKAAPSVTLFPPSSEELQANKATLVCLISDFYPGAVTVAW

KADSSPVKAGVETTTPSKQSNNKYAASSYLSLTPEQWKSHRSYSCQVTHE

GSTVEKTVAPTECGGSSGSGSGSTGENLYFQGSAGTTGTSASTSGYPYDV

PDYAGGGGSAGGTATLEVLFQGPSSGSSSSGGTGEVQLVESGGGLVKPGG
```

-continued
```
SLRLSCSASGFDFDNAWMTWVRQPPGKGLEWVGRITGPGEGWSVDYAAPV

EGRFTISRLNSINFLYLEMNNLRMEDSGLYFCARTGKYYDFWSGYPPGEE

YFQDWGRGTLVTVSSASTKGPSVFPLAPSSKSTSGGTAALGCLVKDYFPE

PVTVSWNSGALTSGVHTFPAVLQSSGLYSLSSVVTVPSSSLGTQTYICNV

NHKPSNTKVDKRVEPKSCSRGGGGSGGSGGSGGSMSSQIRQNYSTDVEA

AVNSLVNLYLQASYTYLSLGFYFDRDDVALEGVSHFFRELAEEKREGYER

LLKMQNQRGGRALFQDIKKPAEDEWGKTPDAMKAAMALEKKLNQALLDLH

ALGSARTDPHLCDFLETHFLDEEVKLIKKMGDHLTNLHRLGGPEAGLGEY

LFERLTLRHD
```

In another aspect, described herein are methods of vaccinating subjects by administering a therapeutically effective amount of the fusion proteins described herein to a mammal in need thereof, typically a young, juvenile, or neonatal mammal. Therapeutically effective means an amount effective to produce the desired therapeutic effect, such as providing a protective immune response against the antigen in question.

Any suitable method or route can be used to administer the fusion proteins and vaccines described herein. Routes of administration include, for example, oral, intravenous, intraperitoneal, subcutaneous, or intramuscular administration.

It is understood that the fusion proteins described herein, where used in a mammal for the purpose of prophylaxis or treatment, will be administered in the form of a composition additionally comprising a pharmaceutically acceptable carrier. Suitable pharmaceutically acceptable carriers include, for example, one or more of water, saline, phosphate buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the binding proteins. The compositions of the injection may, as is well known in the art, be formulated so as to provide quick, sustained or delayed release of the active ingredient after administration to the mammal.

Although human antibodies are particularly useful for administration to humans, they may be administered to other mammals as well. The term "mammal" as used herein is intended to include, but is not limited to, humans, laboratory animals, domestic pets and farm animals.

Also included herein are kits for vaccination, comprising a therapeutically or prophylactically effective amount of a fusion protein described herein. The kits can further contain any suitable adjuvant for example. Kits may include instructions.

The above disclosure generally describes the present invention. A more complete understanding can be obtained by reference to the following specific examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

The following examples do not include detailed descriptions of conventional methods, such as those employed in the construction of vectors and plasmids, the insertion of genes encoding polypeptides into such vectors and plasmids, or the introduction of plasmids into host cells. Such methods are well known to those of ordinary skill in the art and are described in numerous publications including Sambrook, J., Fritsch, E. F. and Maniatis, T. (1989), Molecular Cloning: A Laboratory Manual, 2nd edition, Cold Spring Harbor Laboratory Press, which is incorporated by reference herein.

Without further description, it is believed that one of ordinary skill in the art can, using the preceding description and the following illustrative examples, make and utilize the compounds of the present invention and practice the claimed methods. The following working examples therefore, specifically point out the typical aspects of the present invention, and are not to be construed as limiting in any way the remainder of the disclosure.

EXAMPLES

Figure 2A:
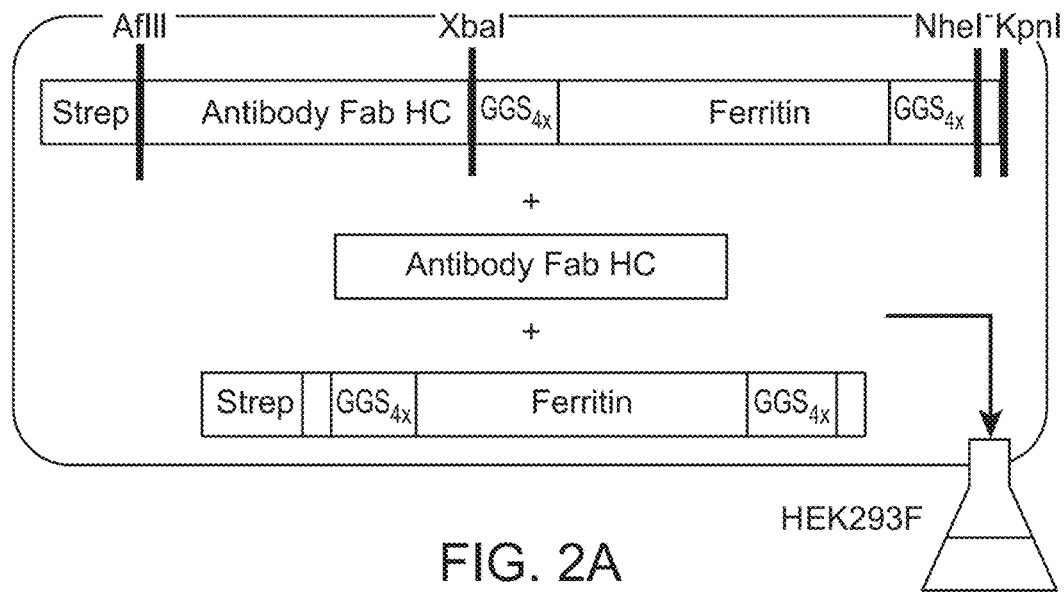
FIGS. 2A, 2B, and 2C show a schematic of the constructs used to produce the antibody Fabs expressing Ferritin (FIG. 2A) or Lumazine synthase (FIG. 2B) nanoparticles of the present invention.
Figure 2B:
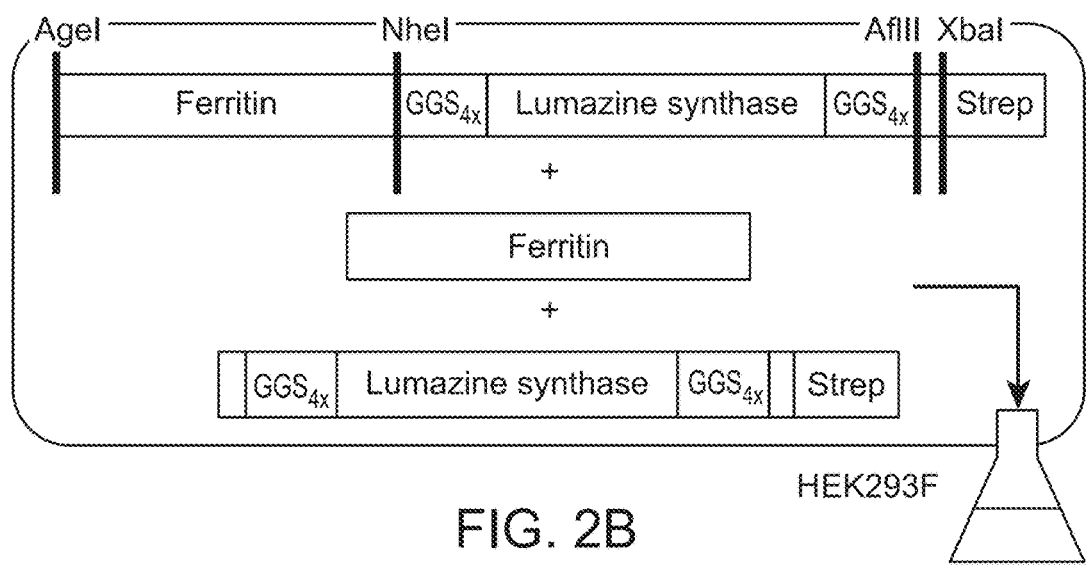
Figure 2C:
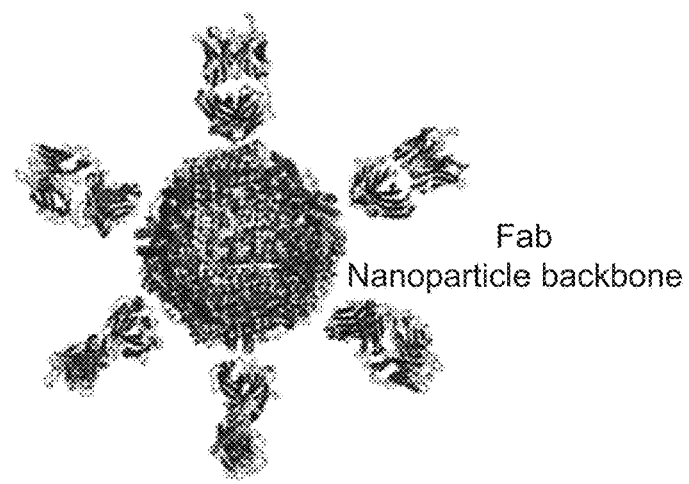

Example 1: Construct Design, Cloning, Expression and Purification of Nanoparticles of the Present Invention Construct Design and Cloning The amino acid sequence for human ferritin L chain (Uniprot: P02792) was obtained, and a 12 amino acid $GGS_{4x}$ linker was added to the N- and C-terminus. Upstream of the N-terminal linker, a StrepTag II affinity tag was added to facilitate affinity purification, and AflIII and XbaI restriction sites were added to facilitate downstream cloning. Furthermore, NheI and KpnI restriction sites were added downstream to the C-terminal linker (FIG. 2A). Similarly, the amino acid sequence of *Thermotoga maritima* lumazine synthase (Uniprot: Q9X2E5) was obtained and flanked with N- and C-terminal $GGS_{4x}$ linkers. AgeI and NheI restriction sites were added to the N-terminus of this construct, and AflIII and XbaI sites were added to the C-terminus, followed by a StrepTag II (FIG. 2B). Both constructs were codon optimized for human expression, synthesized, and cloned into pHLsec expression vector. The heavy chain of Epratuzumab Fab (Epratuzumab HC) or Denintuzumab Fab (Denintuzumab HC) was cloned to the N-terminus of ferritin (FIG. 2A) and lumazine synthase (FIG. 2B) constructs using the above-mentioned restriction sites. In addition, eGFP and iLOV were cloned to the C-terminus of ferritin using NheI and KpnI restriction sites.

Expression and Purification of Nanoparticles

Fab HC-nanoparticle constructs, Fab LC and unconjugated nanoparticle (where Fab is either denintuzumab or epratuzumab as examples, and nanoparticle is either ferritin (FIG. 2A) or lumazine synthase (FIG. 2B)) were transiently co-transfected into HEK293F (Thermo Fisher Scientific) cells in a 1:1:1 ratio. Cells were split in 200 mL cultures at $0.8 \times 10^6$ cells $mL^{-1}$. 50 µg of DNA was filtered and mixed in a 1:1 ratio with transfection reagent FectoPRO (Polyplus Transfections), and incubated at room temperature for 10 min. The DNA: FectoPRO solution was then added directly to the cells, and cells were incubated at 37° C., 180 rpm, 8% $CO_2$ in a Multitron Pro shaker (Infors HT) for 6-7 days.

Figures 3A, 3B:
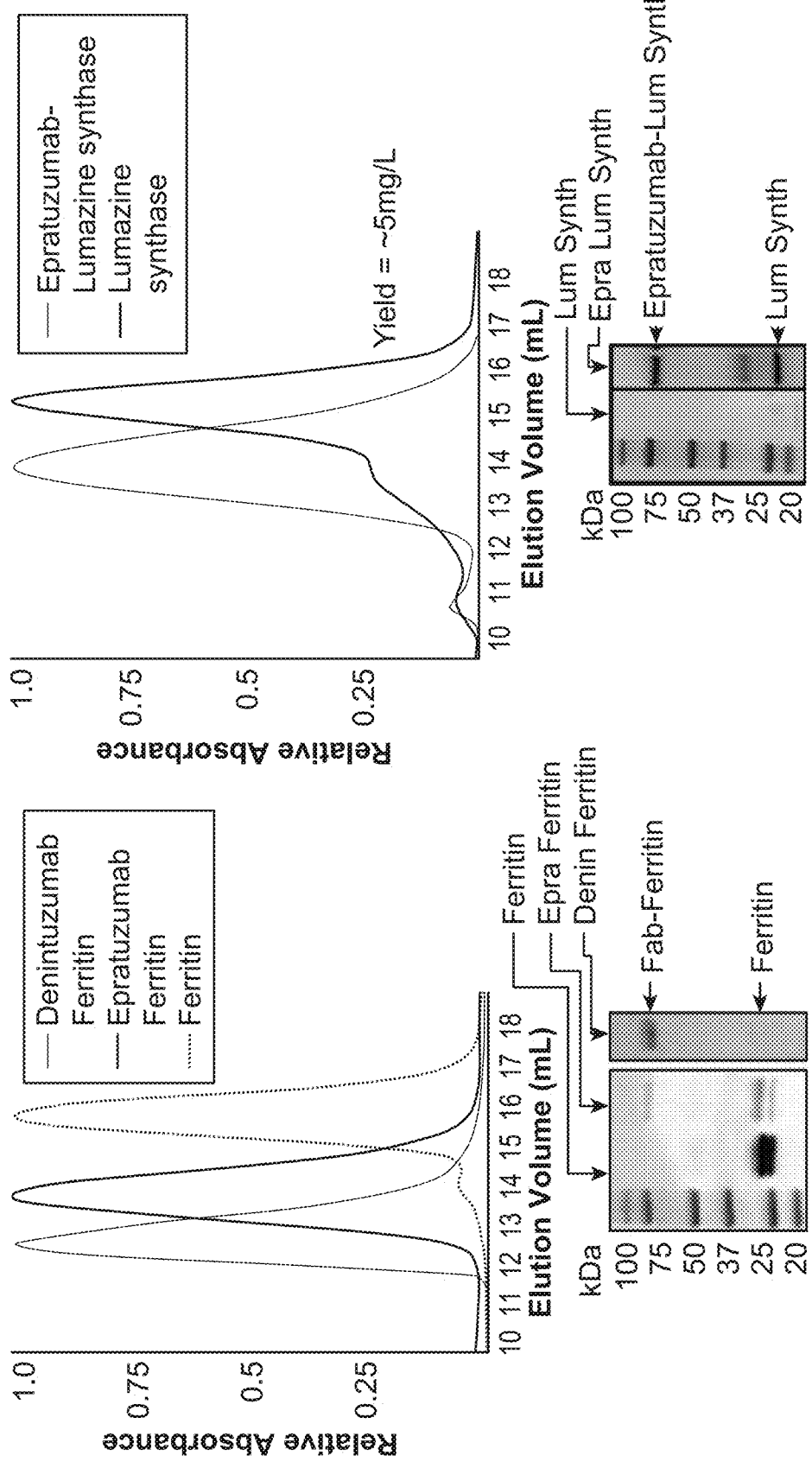
FIGS. 3A and 3B show data representing the purity of the antibody Fab expressing Ferritin (FIG. 3A) or Lumazine synthase (FIG. 3B) nanoparticles produced in accordance with the methods of FIGS. 2A and 2B as determined by affinity chromatography and SDS-PAGE analysis.

Cells were harvested by centrifugation at 6,371×g for 20 min, and supernatants were retained and filtered using a 0.22 µm Steritop filter (EMD Millipore). Supernatants were passed through a StrepTrap affinity column (GE Healthcare) at 4 mL min-1. The column was washed with 20 mM Tris pH 9.0, 150 mM NaCl, 1 mM EDTA buffer prior to elution with 20 mM Tris pH 9.0, 150 mM NaCl, 1 mM EDTA, and 10 mM desthiobiotin. Fractions containing eluted nanoparticles were pooled, concentrated, and separated on a Superose 6 Increase size exclusion column (GE Healthcare) at 0.5 mL min-1 in 20 mM Tris pH 9.0, 150 mM NaCl buffer to achieve size homogeneity. Data demonstrating the purity of antibody Fab expressing Ferritin (FIG. 3A) and Lumazine synthase (FIG. 3B) nanoparticles is shown by elution profiles (top) and western blots (bottom).

The same protocol was used to produce Ferritin-GFP/iLOV particles, with the exception that HEK293F cells were transfected with the Ferritin-GFP/iLOV constructs alone.

Figure 4B:
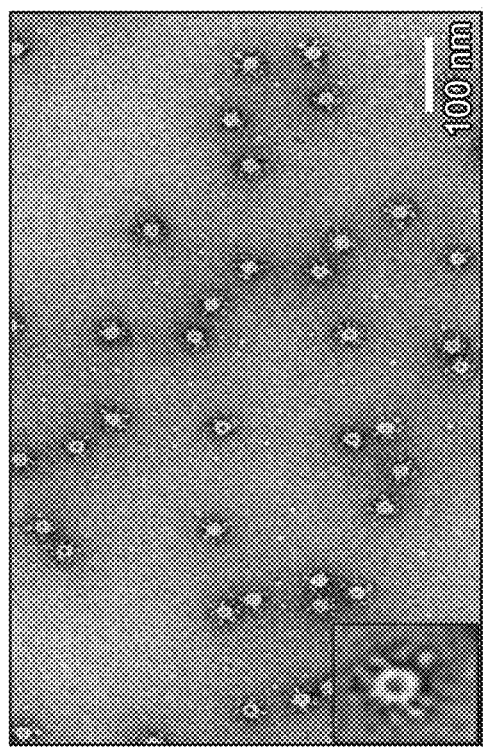
FIGS. 4A and 4B show electron micrographs of the antibody Fab expressing Ferritin (FIG. 4A) or Lumazine synthase (FIG. 4B) nanoparticles described herein.
Figure 4A:
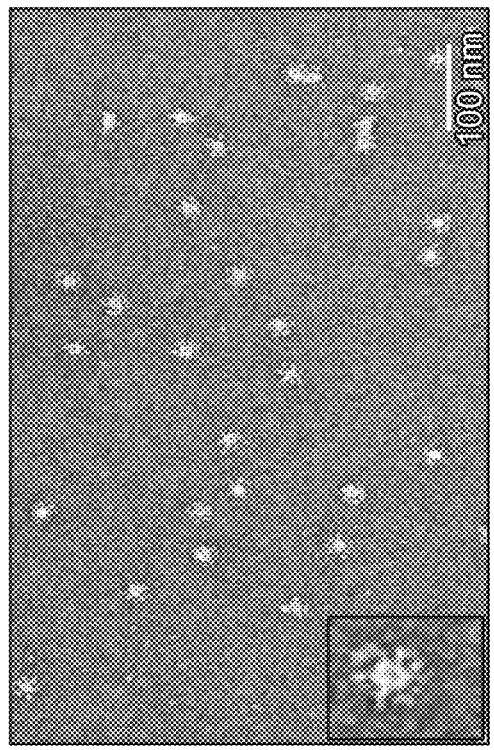

Example 2: Negative Stain Electron Microscopy of Antibody Fab Expressing Ferritin and Lumazine Synthase Nanoparticles The production of electron micrographs of the antibody Fab expressing Ferritin (FIG. 4A) and Lumazine synthase (FIG. 4B) nanoparticles of the present invention is described. Purified nanoparticles were stained with 2% uranyl formate. A dataset consisting of 20-50 images was collected manually with a field-emission FEI Tecnai F20 electron microscope operating at 200 kV and an electron exposure of 30 $e^- Å^{-2}$. Images were acquired with an Orius charge-coupled device (CCD) camera (Gatan Inc.) at a calibrated magnification of 34,483×, resulting in a pixel size of 2.61 A at the specimen and a defocus range of approximately 0.75 to 2 µm was used. A total of ~1,000 particle images were manually selected with EMAN2. 2D classification of particle images was performed with 50 classes allowed.

Figures 5A, 5B, 5C:
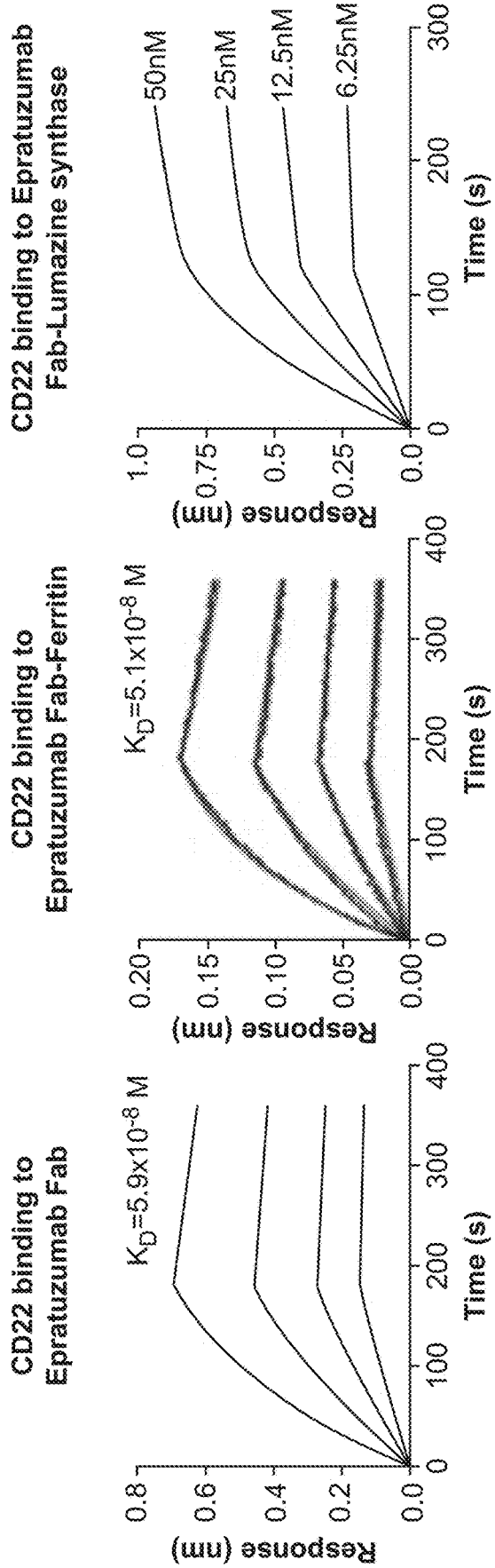
FIGS. 5A, 5B, and 5C show data representing the binding affinity of CD22 to antibody Fab without a nanoparticle backbone (FIG. 5A), antibody Fab expressing Ferritin (FIG. 5B) or Lumazine synthase (FIG. 5C) nanoparticles described herein.

Example 3: Binding Affinities of Antibody Fab Expressing Ferritin and Lumazine Synthase Nanoparticles The binding affinities of epratuzumab Fab (FIG. 5A), epratuzumab-ferritin (FIG. 5B) and epratuzumab-lumazine synthase (FIG. 5C) to CD22 were measured by biolayer interferometry (BLI) using the Octet RED96 BLI system (Pall ForteBio). Ni-NTA biosensors were hydrated in 1× kinetics buffer (1×PBS, pH 7.4, 0.002% Tween, 0.01% BSA) and loaded with 25 ng $µL^{-1}$ CD22 (Uniprot: P20273) for 300 s at 1,000 rpm. Biosensors were then transferred into wells containing 1× kinetics buffer to baseline for 60 s before being transferred into wells containing a serial dilution of Fab/nanoparticles. The 180 s association phase was subsequently followed by a 180 s dissociation step in 1× kinetics. Analysis was performed using the Octet software, with a 1:1 fit model.

Figures 6A, 6B, 6C:
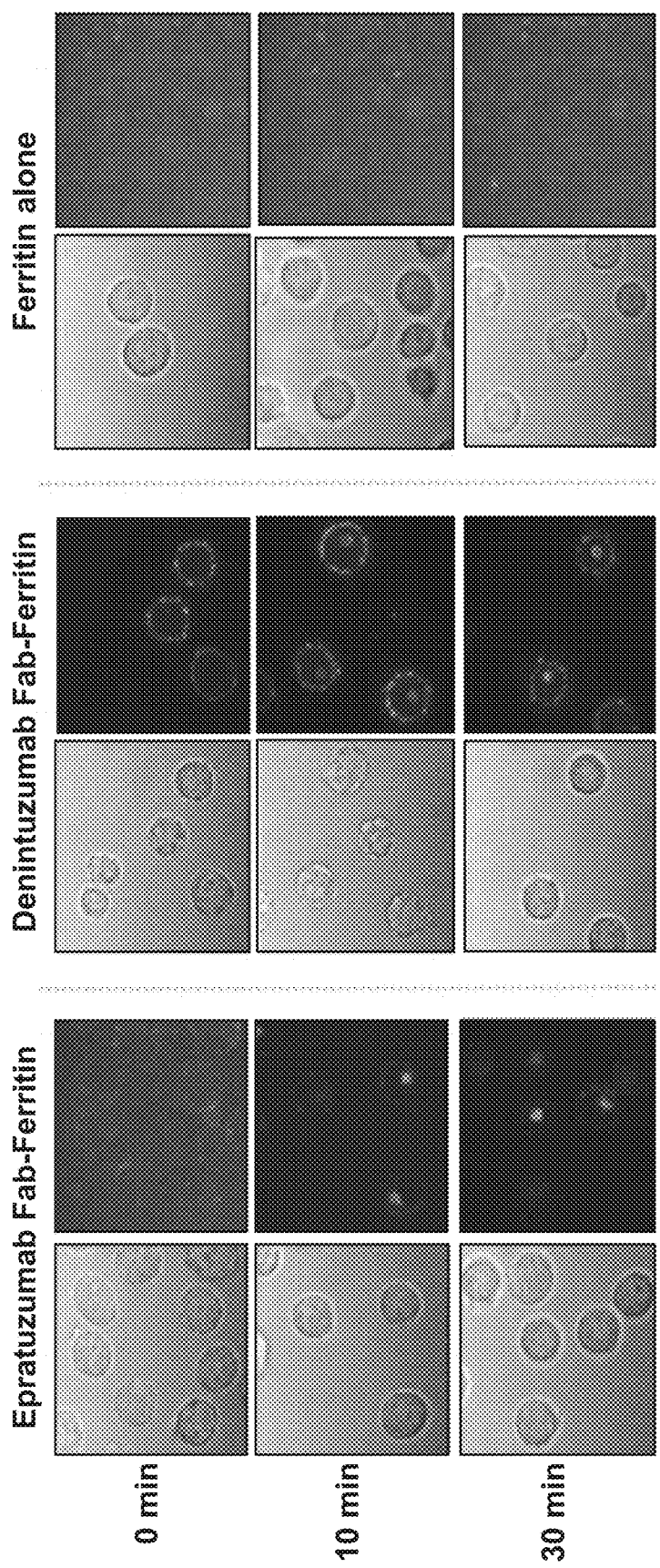
FIGS. 6A, 6B, and 6C show data demonstrating the receptor mediated endocytosis of two different antibody Fab expressing Ferritin nanoparticles (FIGS. 6A and 6B) as compared to the absence of endocytosis with a Ferritin nanoparticle alone (FIG. 6C)

Example 4: Receptor Mediated Endocytosis of Antibody Expressing Fab Nanoparticles Antibody-ferritin (FIGS. 6A and 6B) or ferritin alone (FIG. 6C) nanoparticles (0.5 mg $ml^{-1}$-1 mg $mL^{-1}$) were labeled at a ratio of 10:1 v/v with Alexa Fluor-647 (4 mg $mL^{-1}$) (Thermo Fisher Scientific) for 1 h. Nanoparticles were then dialyzed over 8 h in 2 L of 1×PBS, changing the dialysis buffer 3 times. 5 µg $mL^{-1}$ of dialyzed, labeled nanoparticles were used to treat human Bjab cells ($1 \times 10^6$ cells $mL^{-1}$) for 5, 10 or 30 min. Following desired internalization time, cells were washed 3 times and dispensed into a Lab-Tek II chamber (Nalge Nunc International). Images were captured using a WaveFX-XI spinning disc confocal microscope (Quorum Technologies) equipped with a 63× oil-immersion objective and an EM-CCD camera (Hamamatsu Photonics). Images of the center plane of the cells were acquired and images were processed and analyzed using Volocity software (Improvision).

Figure 7:
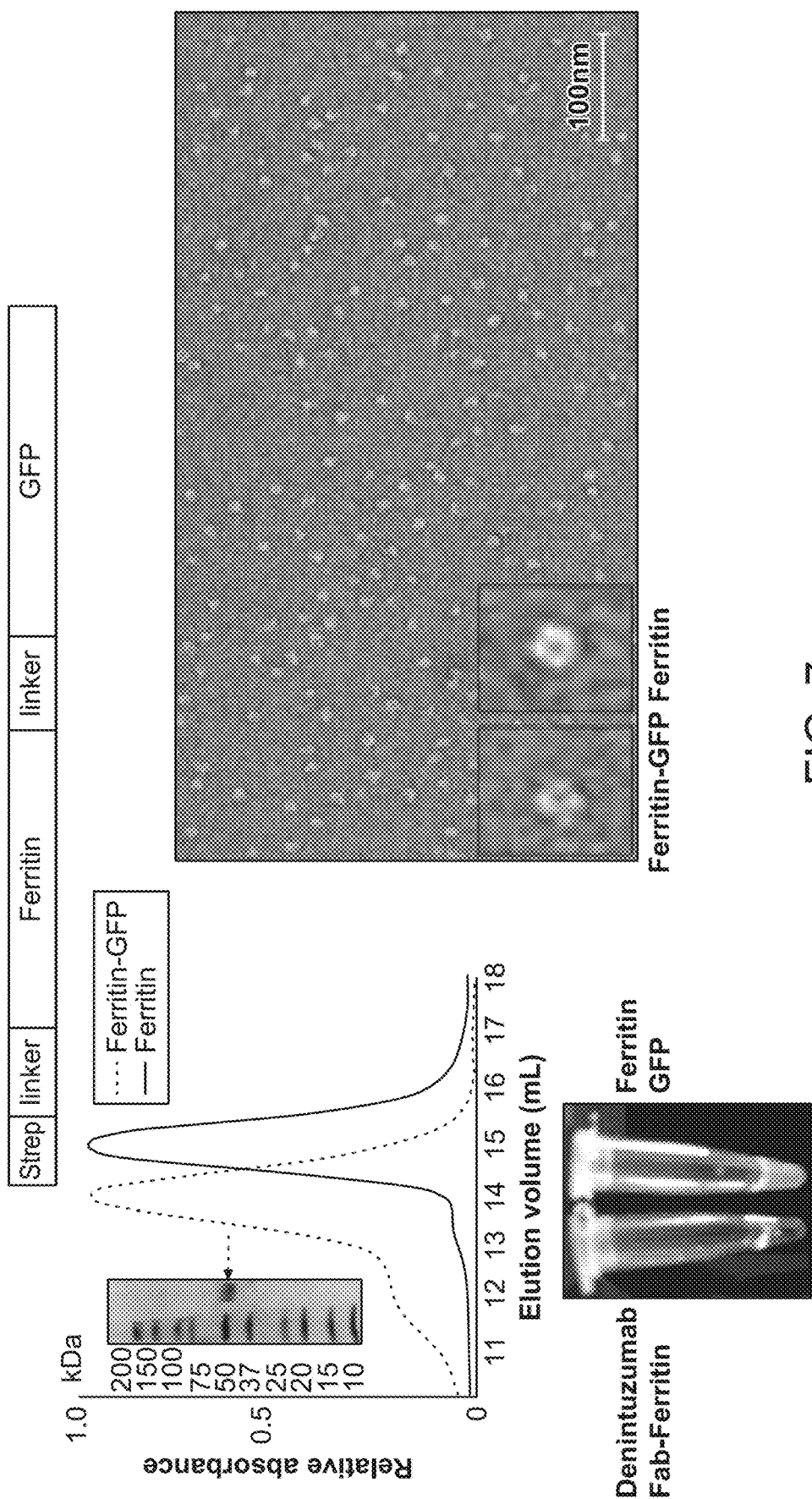
FIG. 7 shows data representing the fluorescent capabilities of the Ferritin nanoparticles described herein.
Figure 8:
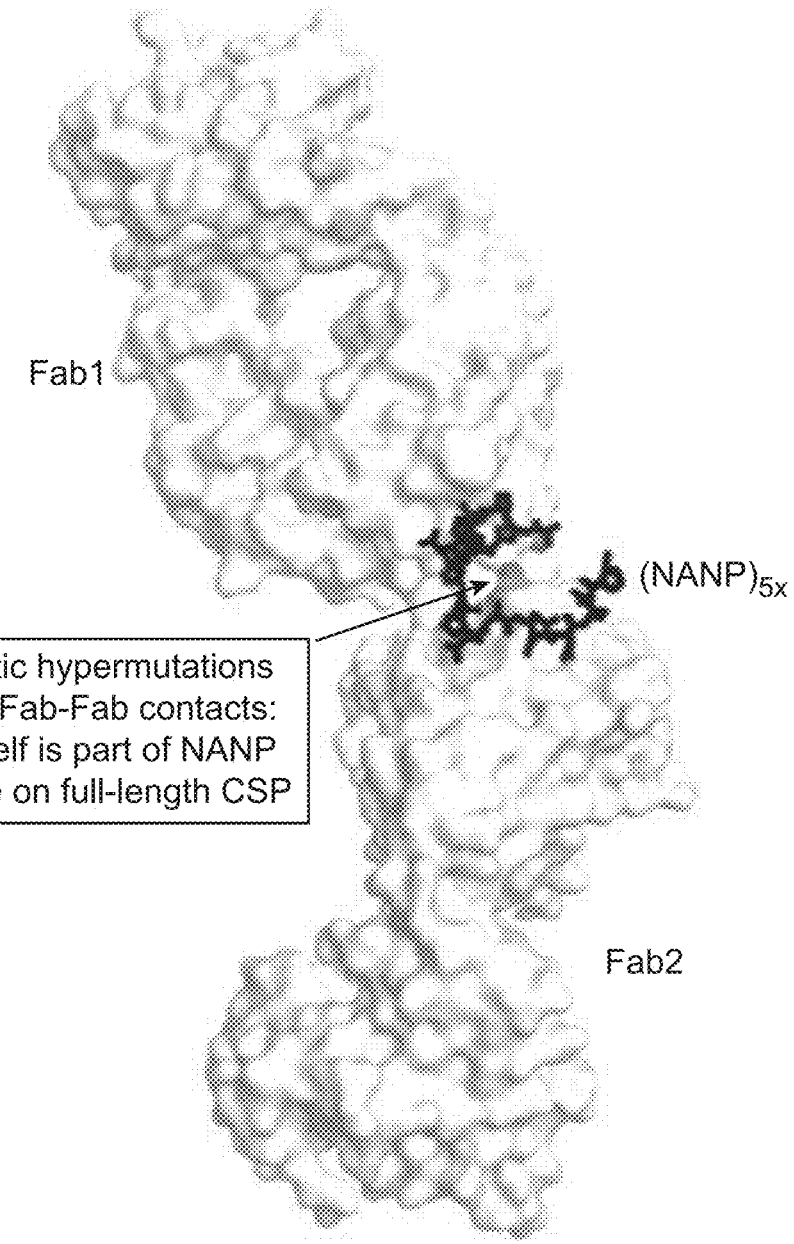
FIG. 8 shows the crystal structure of the interactions between a CSP NANP repeat domain antigen and two Fab antibody fragments.
Figure 9:
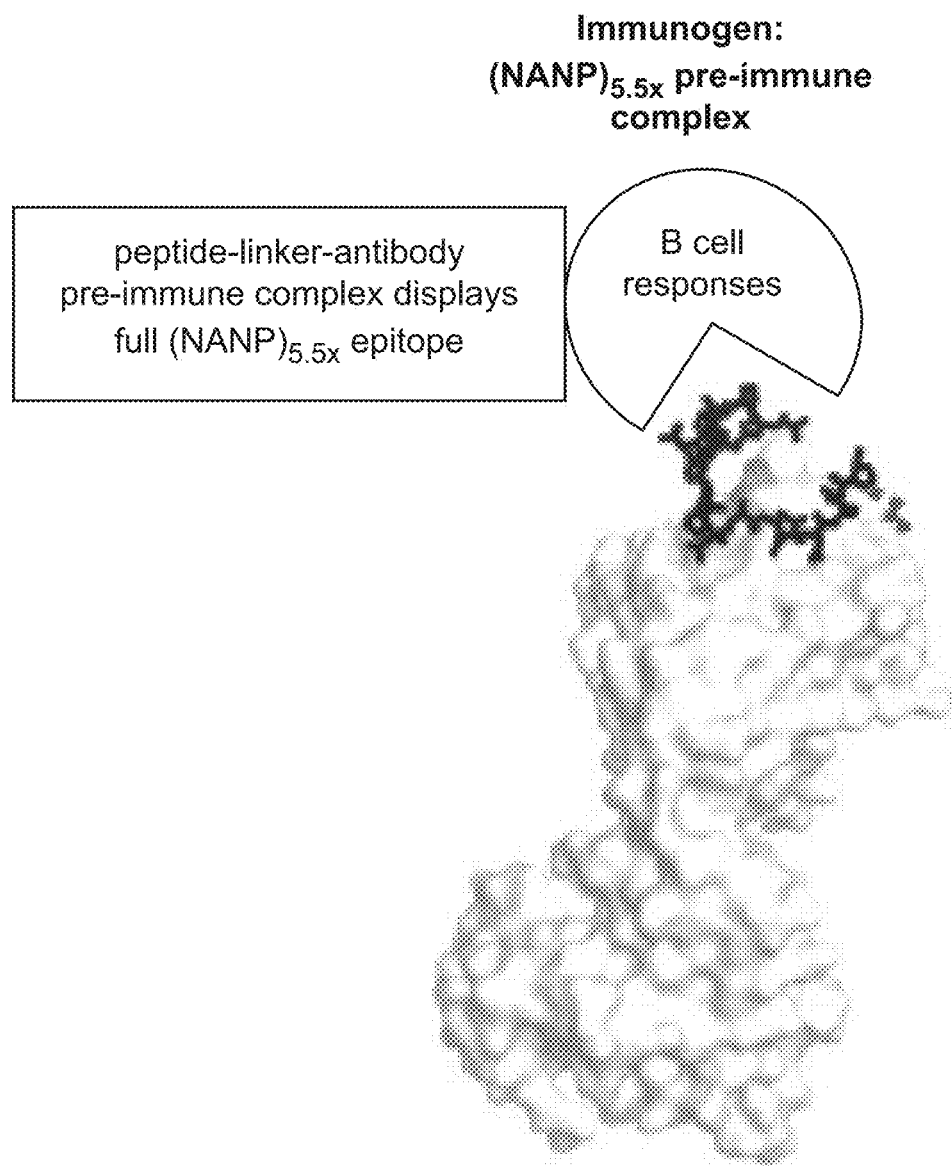
FIG. 9 shows schematic modeling of the interactions between a CSP NANP repeat domain antigen, and Fab antibody fragment, and a B cell.

Example 5. Nanoparticles can be Made Fluorescent by Internal Conjugation of Fluorescent Protein The cloning, expression, purification and EM is as described above. In addition, eGFP and iLOV were cloned to the C-terminus of ferritin using NheI and KpnI restriction sites. With respect to producing Ferritin-GFP/iLOV particles, the protocol is as described above, with the exception that HEK293F cells were transfected with the Ferritin-GFP/iLOV constructs alone. Staining was done as described above in Example 2. Fluorescence of Ferritin-GFP/iLOV nanoparticles was measured with a transilluminator at a wavelength of 365 nm (FIG. 7).

Figure 11:
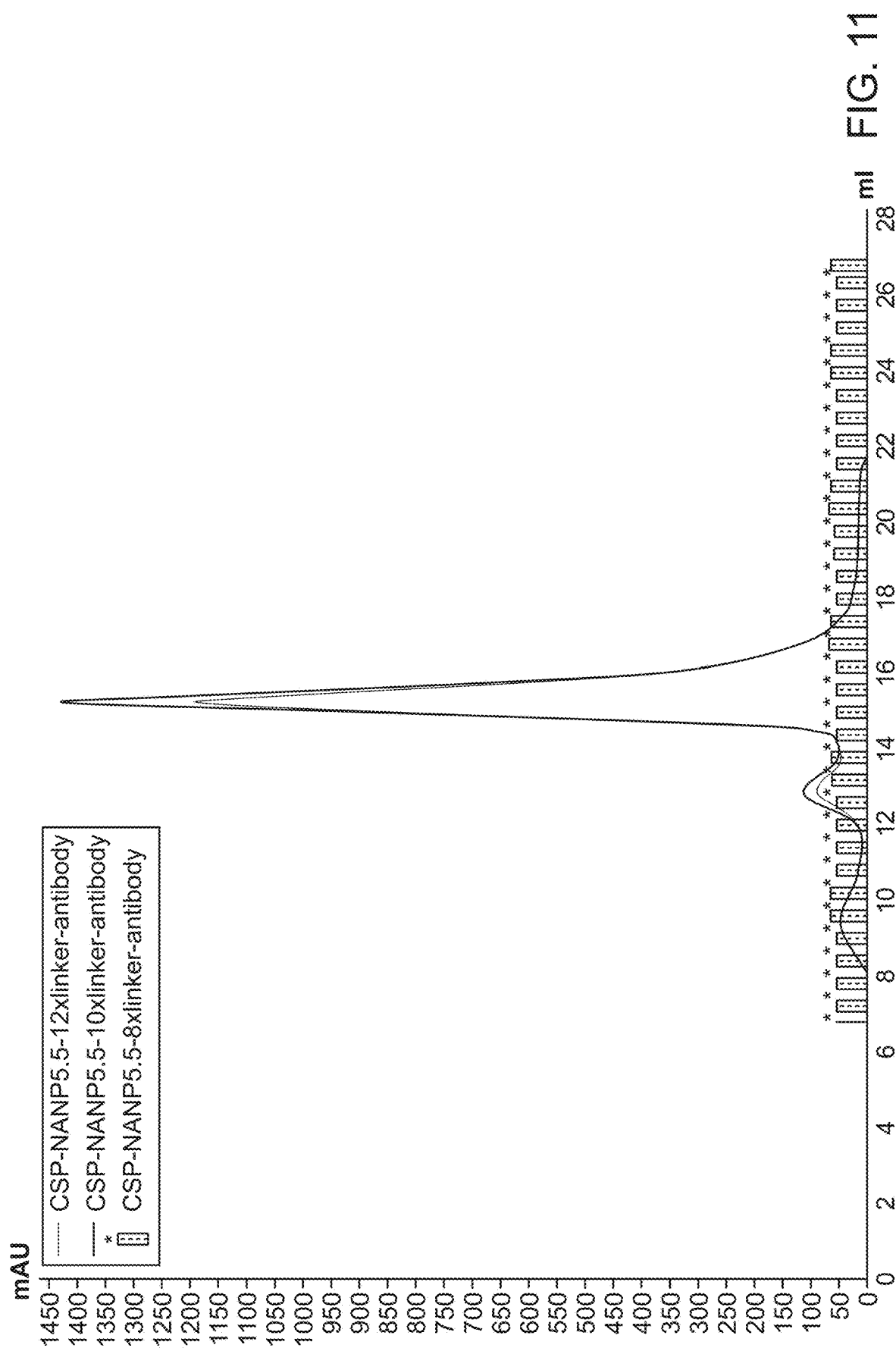
FIG. 11 shows data from size exclusion chromatography purification of the fusion proteins of FIG. 10.
Figure 12:
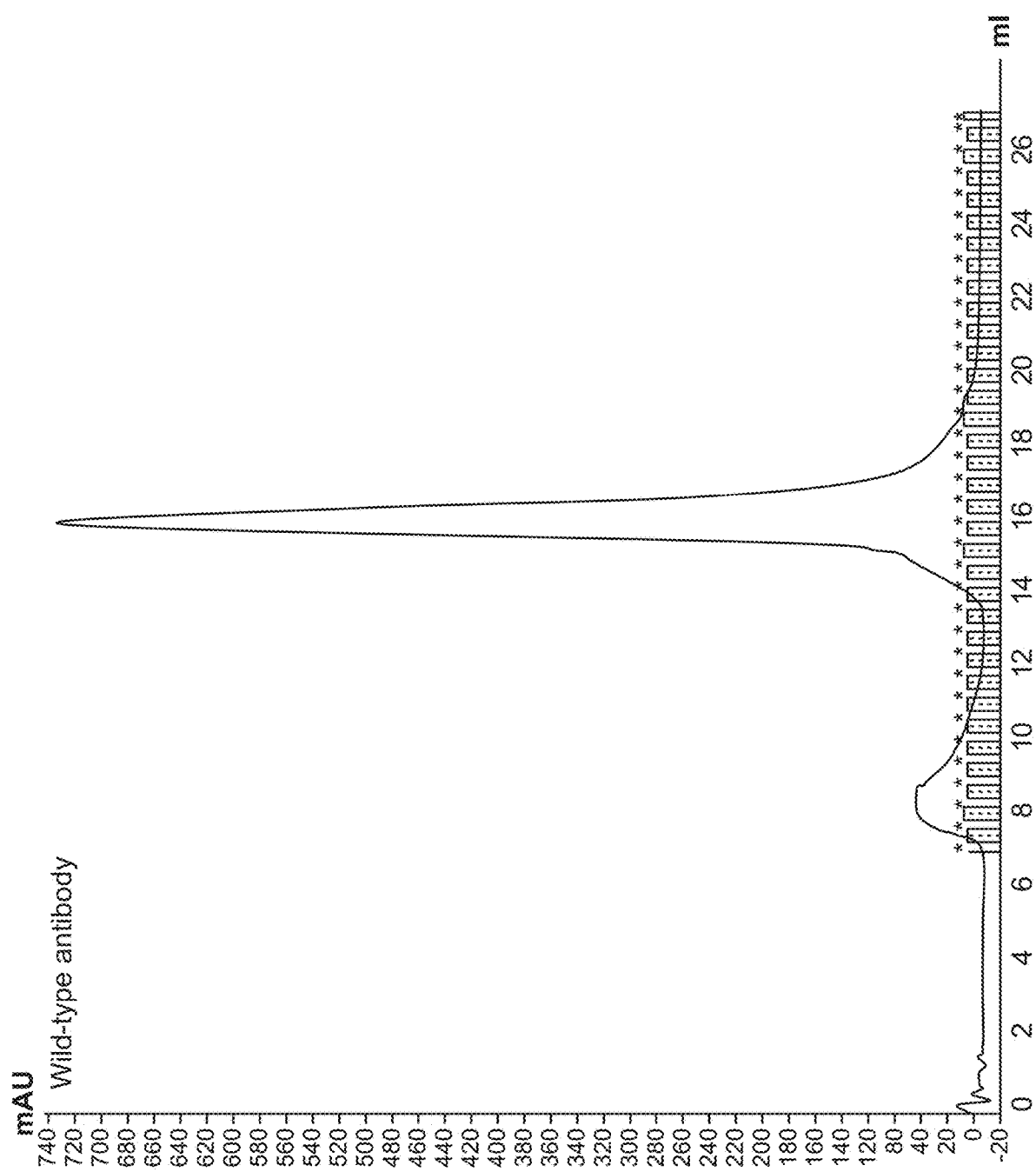
FIG. 12 shows data from size exclusion chromatography purification of a wild-type antibody corresponding to the fusion proteins of FIG. 10 but lacking the CSP NANP repeat domain and the linker.

Example 6: CSP-NPNA5.5-linker-1210 fusion protein expression and purification The fusion proteins were constructed and purified as follows. To begin, 5.5×CSP NPNA repeats followed by either an 8, 10 or 12 residue flexible GGS linker were cloned at the N-terminus of the 1210-HC-Fab sequence in a pcDNA3.4 TOPO expression vector. CSP-NPNA5.5-8x-1210 Fab (FIG. 10A), CSP-NPNA5.5-10x-1210 Fab (FIG. 10B) and CSP-NPNA5.5-12x-1210 Fab (FIG. 10C) were produced by transient expression in HEK293F cells by co-transfection with the 1210-LC gene (FIG. 10D) in a pcDNA3.4 TOPO expression vector using the FectoPRO (Polyplus) transfection reagent. Purification was done via KappaSelect affinity chromatography (GE Healthcare). Fabs were further purified by size exclusion chromatography (Superdex 200 Increase 10/300 GL, GE Healthcare; see FIGS. 11 and 12).

Figure 13:
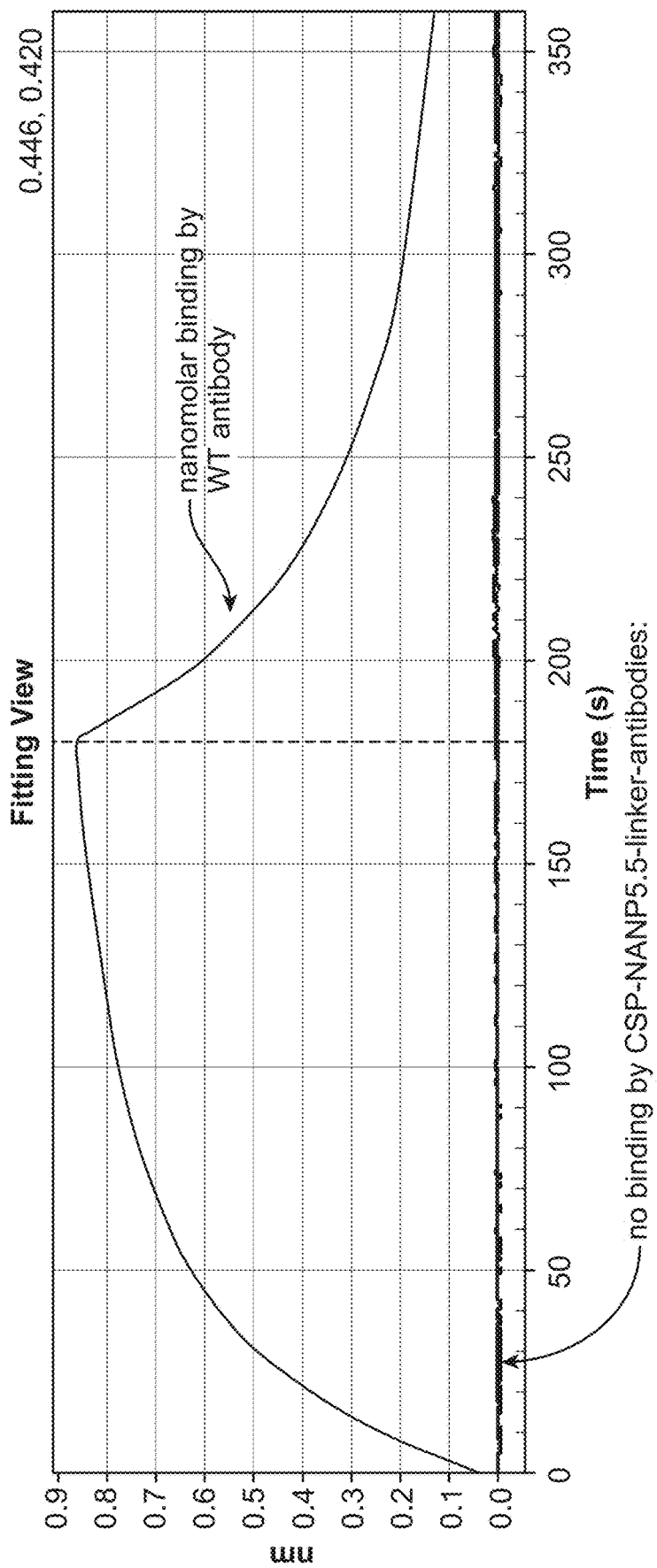
FIG. 13 shows CSP binding kinetics of the fusion proteins of FIG. 10 compared to binding by wild-type antibody.

Example 7: Fusion Proteins do not Bind to CSP but are Recognized and Bound by Wild-Type Antibodies Determination of binding to CSP was conducted as follows. Biolayer interferometry (Octet RED96, ForteBio) experiments were conducted to determine if CSP-NPNA5.5-linker-1210 Fabs could recognize CSP, or whether the CSP binding site was occluded by the NPNA5.5 (FIG. 13). Recombinant CSP was diluted to 10 μg/mL in kinetics buffer (PBS, pH 7.4, 0.01% (w/v) BSA, 0.002% Tween-20) and immobilized onto Ni-NTA (NTA) biosensors (ForteBio). Following establishment of a stable baseline with loaded ligand in kinetics buffer, biosensors were dipped into wells containing 1210 Fab, CSP-NPNA5.5-8x-1210 Fab, CSP-NPNA5.5-10x-1210 Fab and CSP-NPNA5.5-12x-1210 Fab. Tips were then dipped back into kinetics buffer to monitor the dissociation rate.

Figure 14:
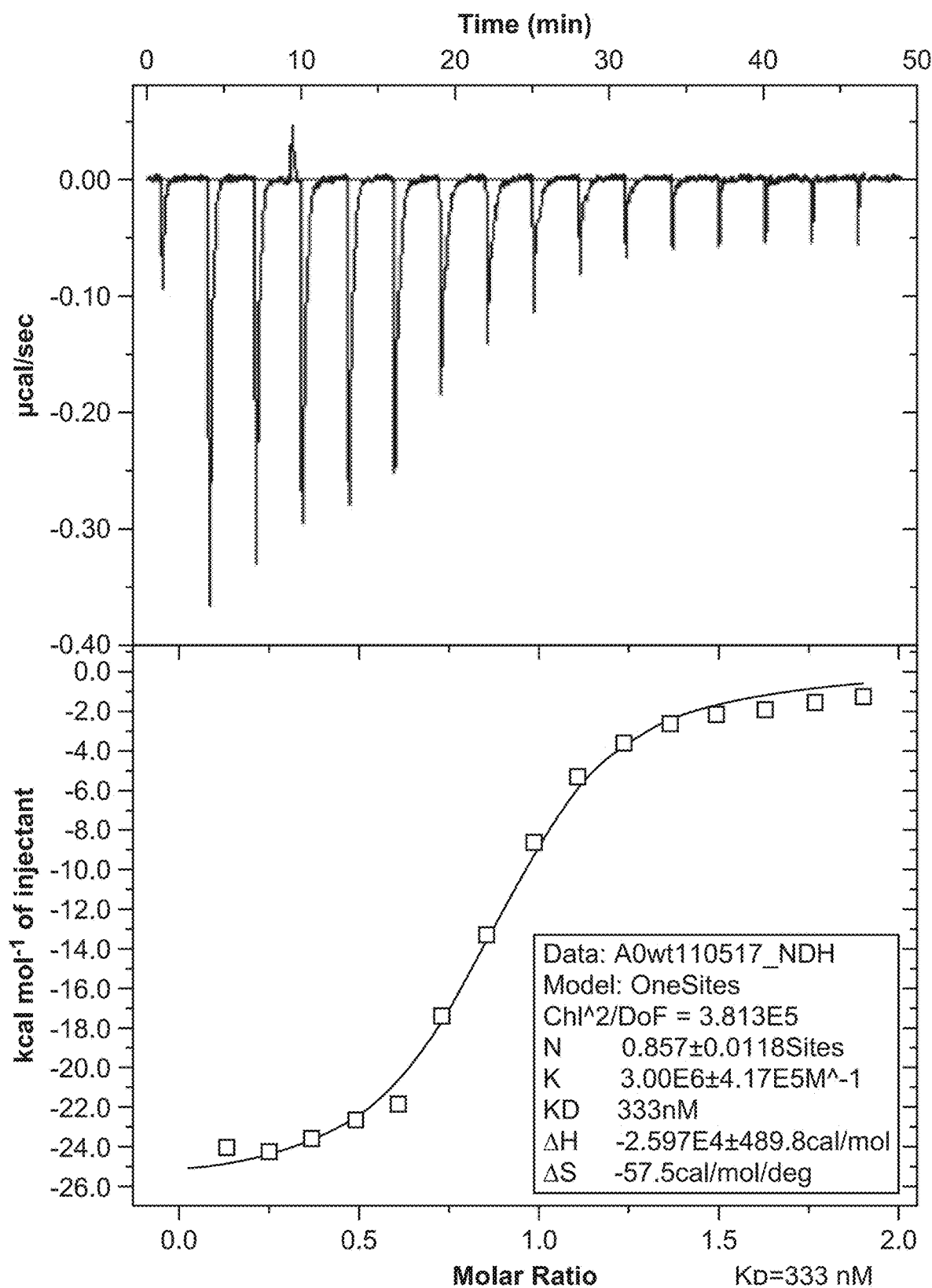
FIG. 14-16 show wild-type antibody binding affinity to the fusion proteins of FIG. 10.
Figure 15:
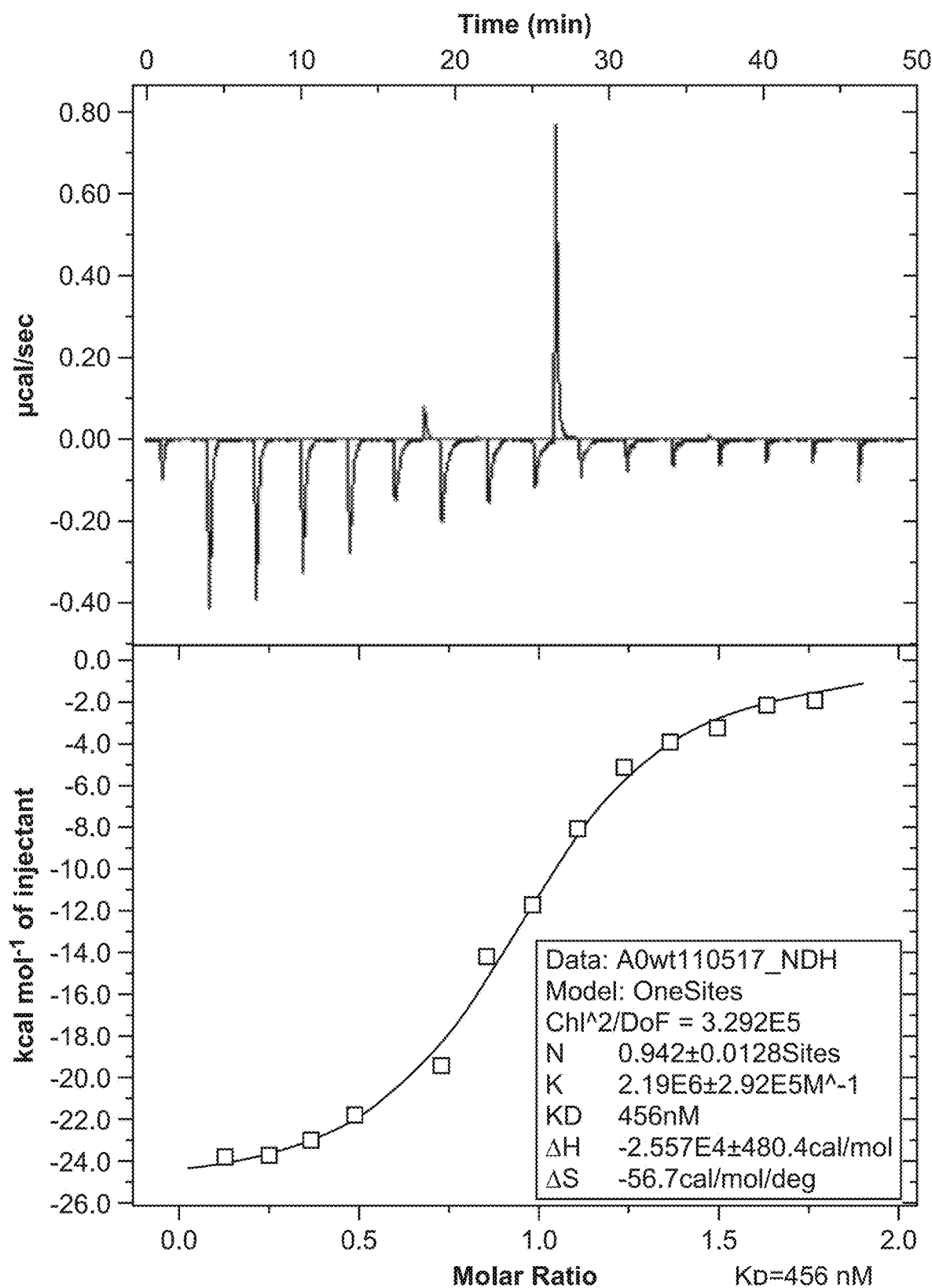
Figure 16:
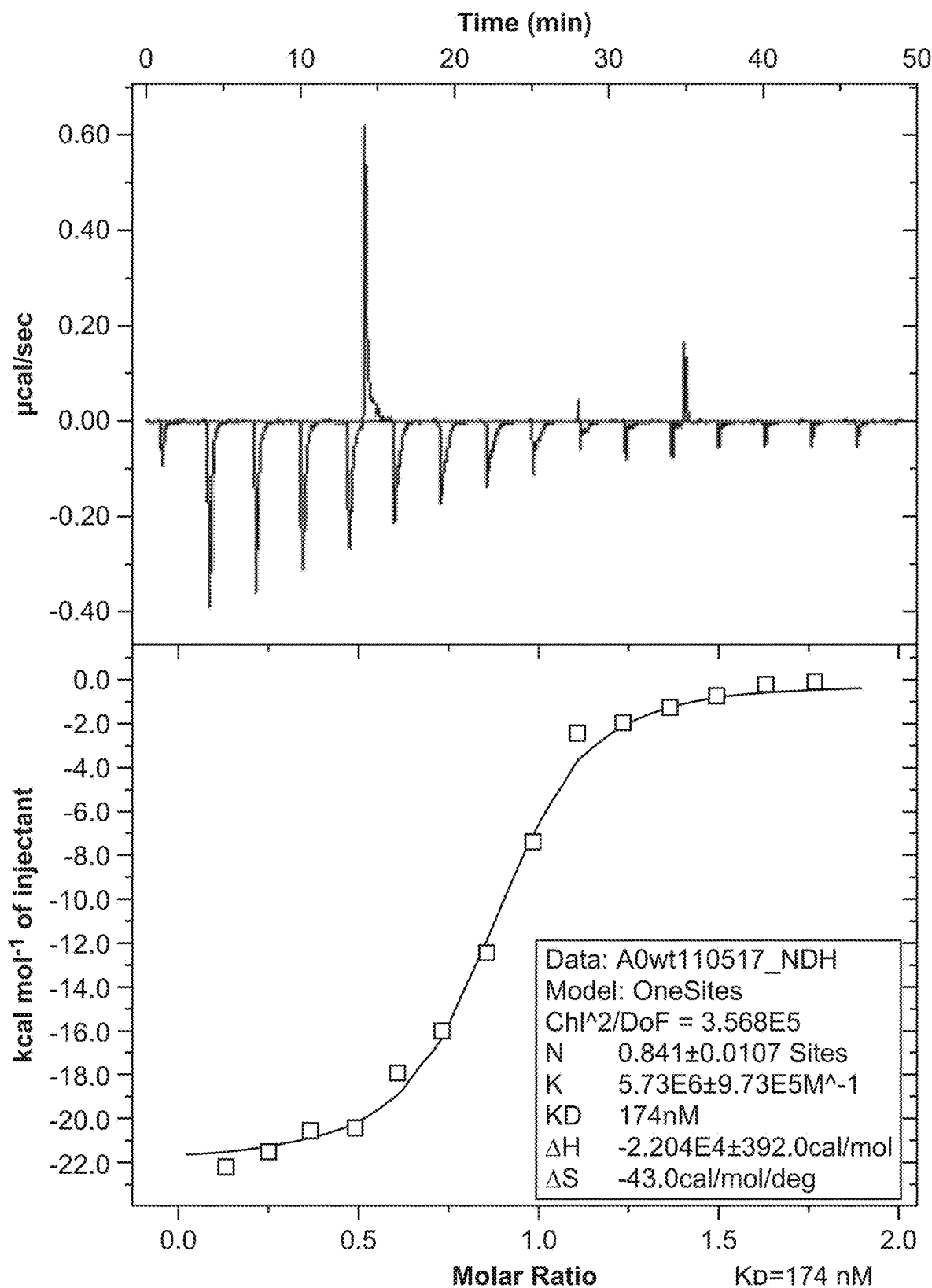
Figure 17:
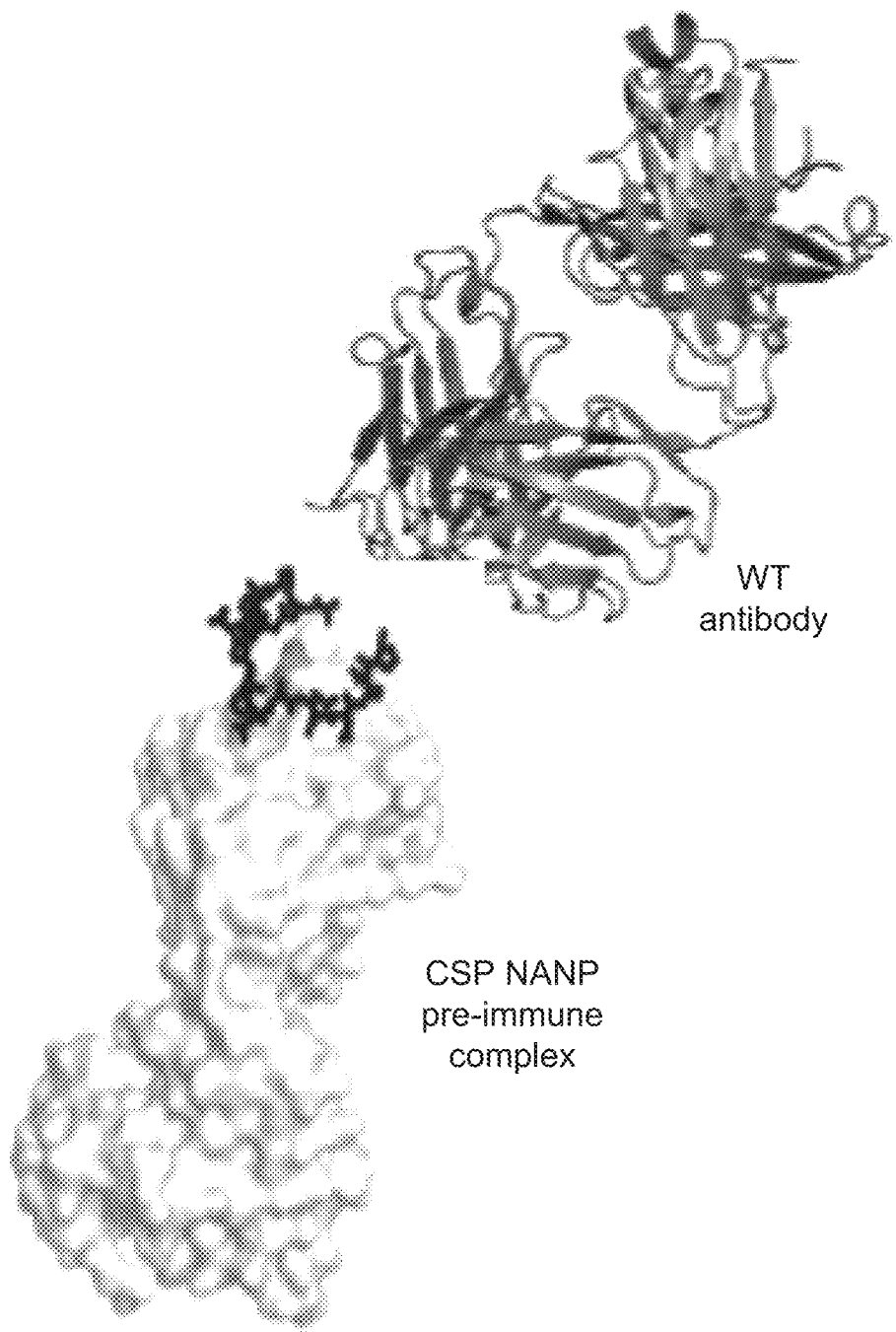
FIG. 17 shows schematic representations of the interaction between wild-type antibody and the fusion proteins of FIG. 10.

Determination of binding affinity of wild-type antibodies for the fusion proteins was conducted using isothermal titration calorimetry (ITC) as follows. calorimetric titration experiments were performed with an Auto-iTC200 Micro-Calorimeter (MicroCal) at 25° C. Proteins were dialyzed against 20 mM Tris, 150 mM NaCl pH 8.0 overnight at 4° C. CSP-NPNA5.5-8x-1210 Fab, CSP-NPNA5.5-10x-1210 Fab and CSP-NPNA5.5-12x-1210 Fab (10 μM) in the calorimetric cell was titrated with 1210 Fab (92 μM) in 15 successive injections of 2.5 μl. The experimental data were analyzed according to a 1:1 binding model in Origin 7.0 and shown in FIGS. 14-16.

Example 8: Size Exclusion Chromatography Multi-Angle Light Scattering (SEC-MALS)

Figures 18A, 18B:
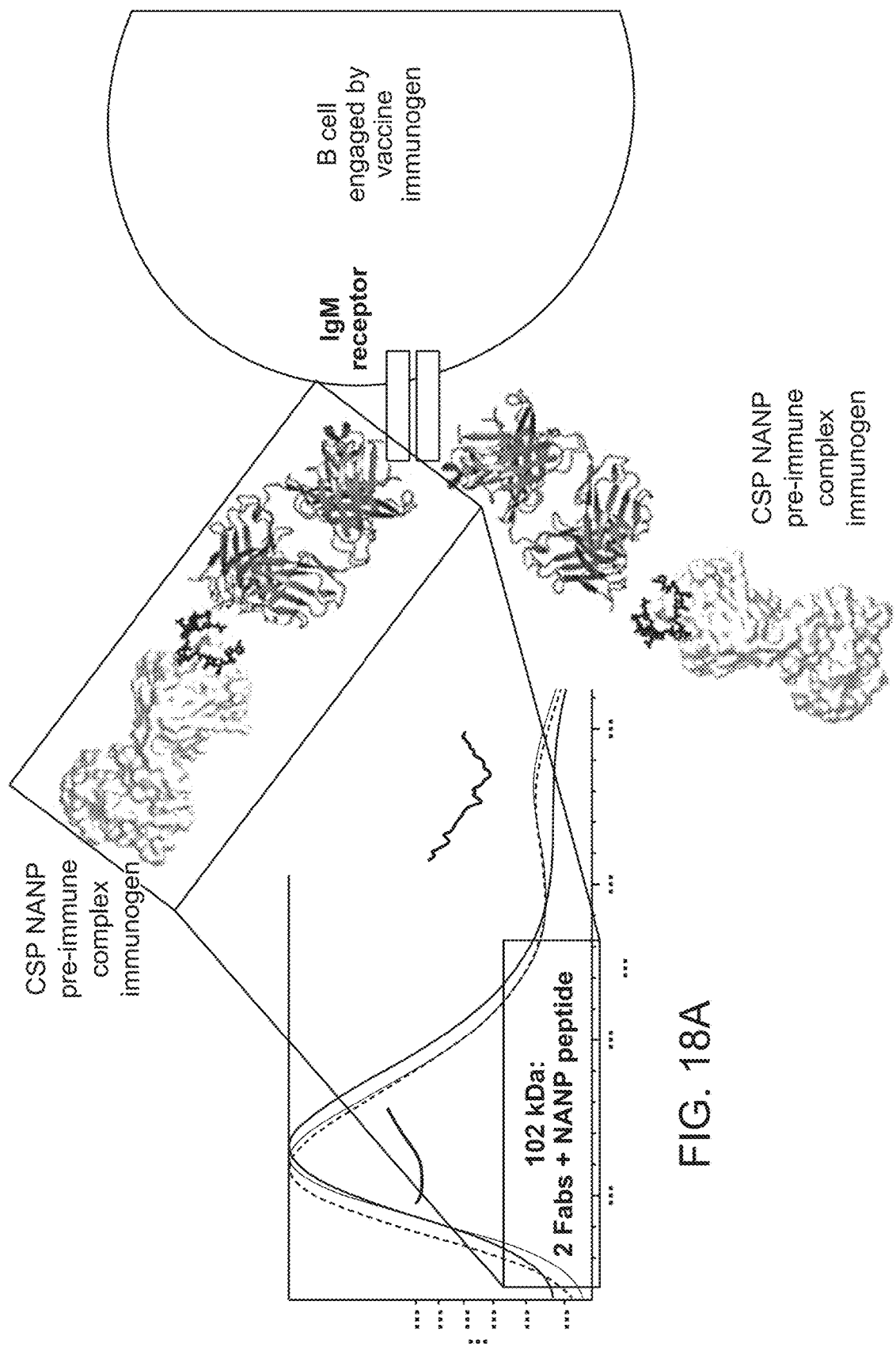
FIG. 18 shows data from size exclusion chromatography coupled with multi-angle light scattering to determine absolute mass for the wild-type antibody and fusion protein interaction and a schematic representing the interaction of a B-cell expressing an IgM receptor specific for the fusion protein described herein.

Determination of the absolute mass of the antibody-fusion protein interaction was conducted as follows. The 1210 Fab/CSP-NPNA5.5-linker-1210 Fab co-complexes recovered from ITC were loaded on a Superdex 200 Increase 10/300 GL (GE Healthcare), coupled in-line on an AKTA Pure chromatography system (GE Healthcare) with the following calibrated detection systems: (i) MiniDawn Treos MALS detector (Wyatt); (ii) quasielastic light scattering (QELS) detector (Wyatt); and (iii) Optilab T-rex refractive index (RI) detector (Wyatt). Data processing was performed using ASTRA software (Wyatt) and shown in FIG. 18A.

Figure 19:
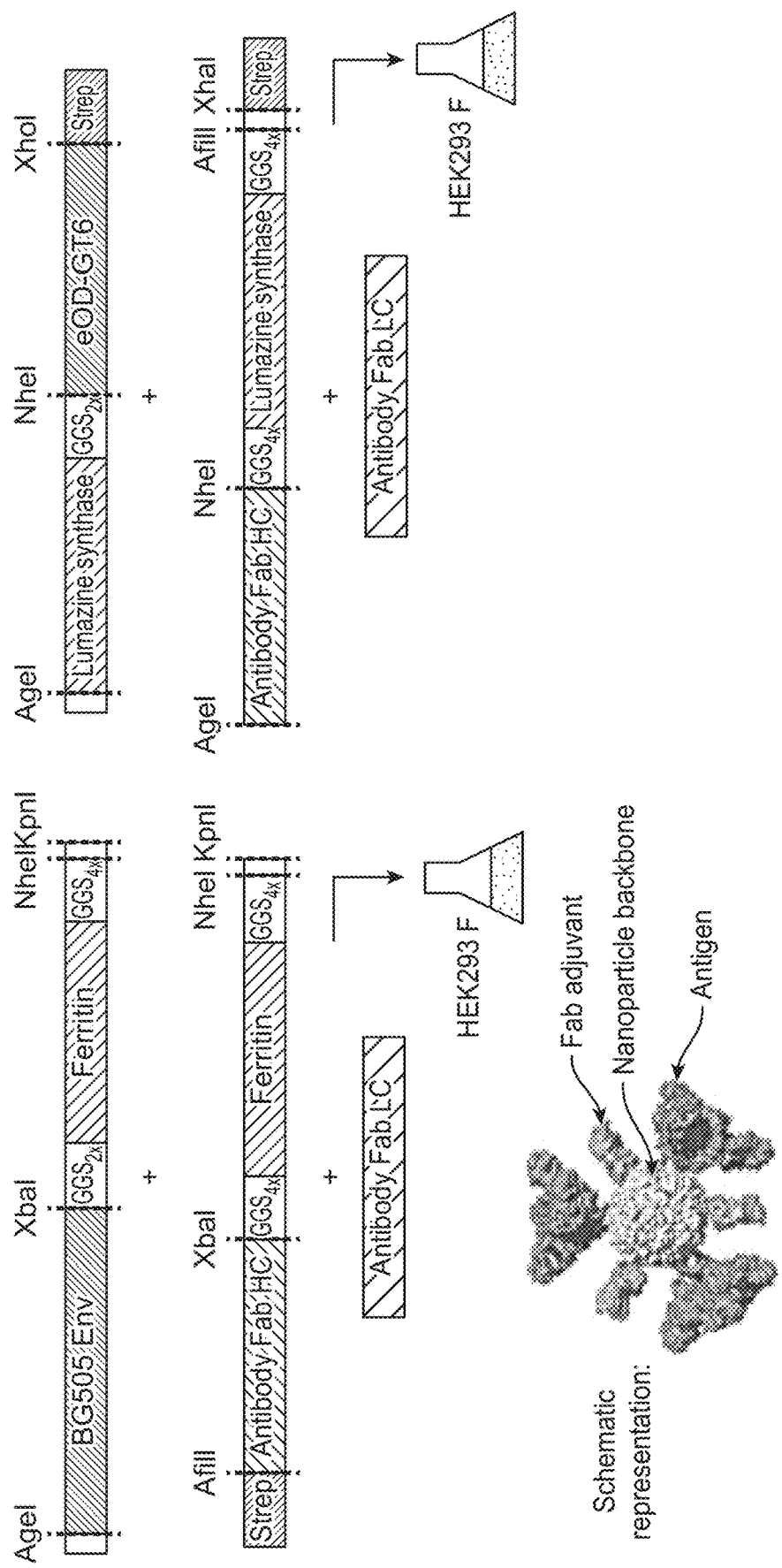
FIG. 19 shows nanoparticles engineered to co-display α-CD19 stimulating Fab and antigens as a vaccine platform.
Figure 20:
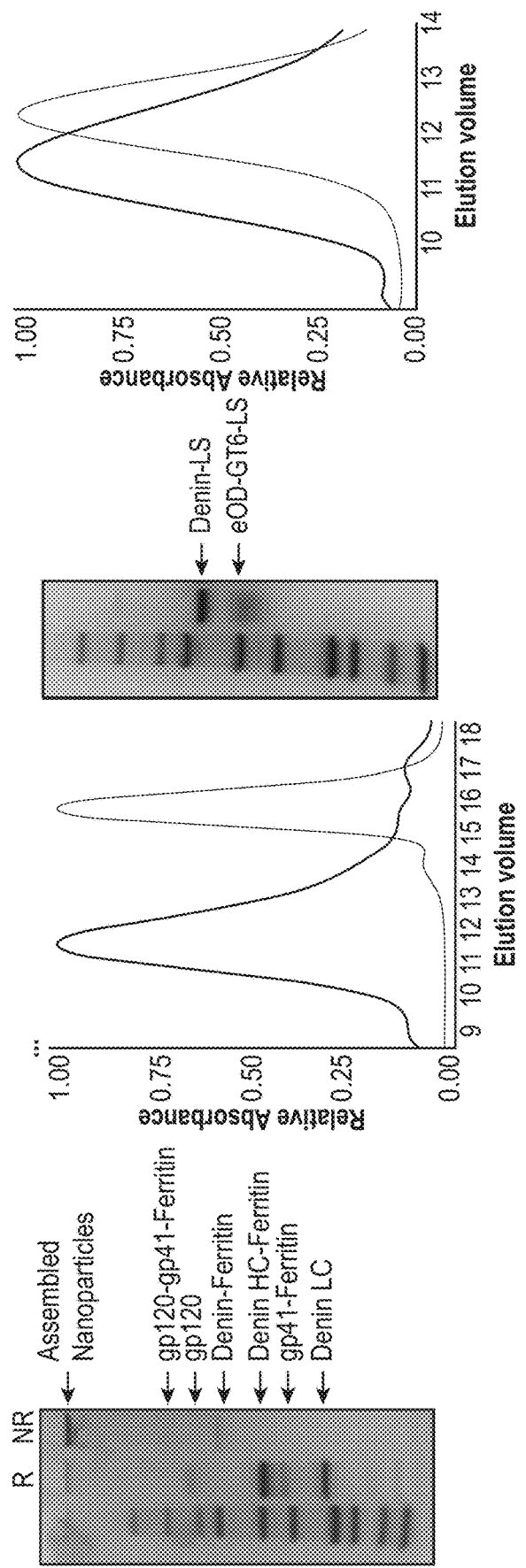
FIG. 20 shows that nanoparticles can be engineered for co-display of stimulating antibodies and antigens.
Figure 22:
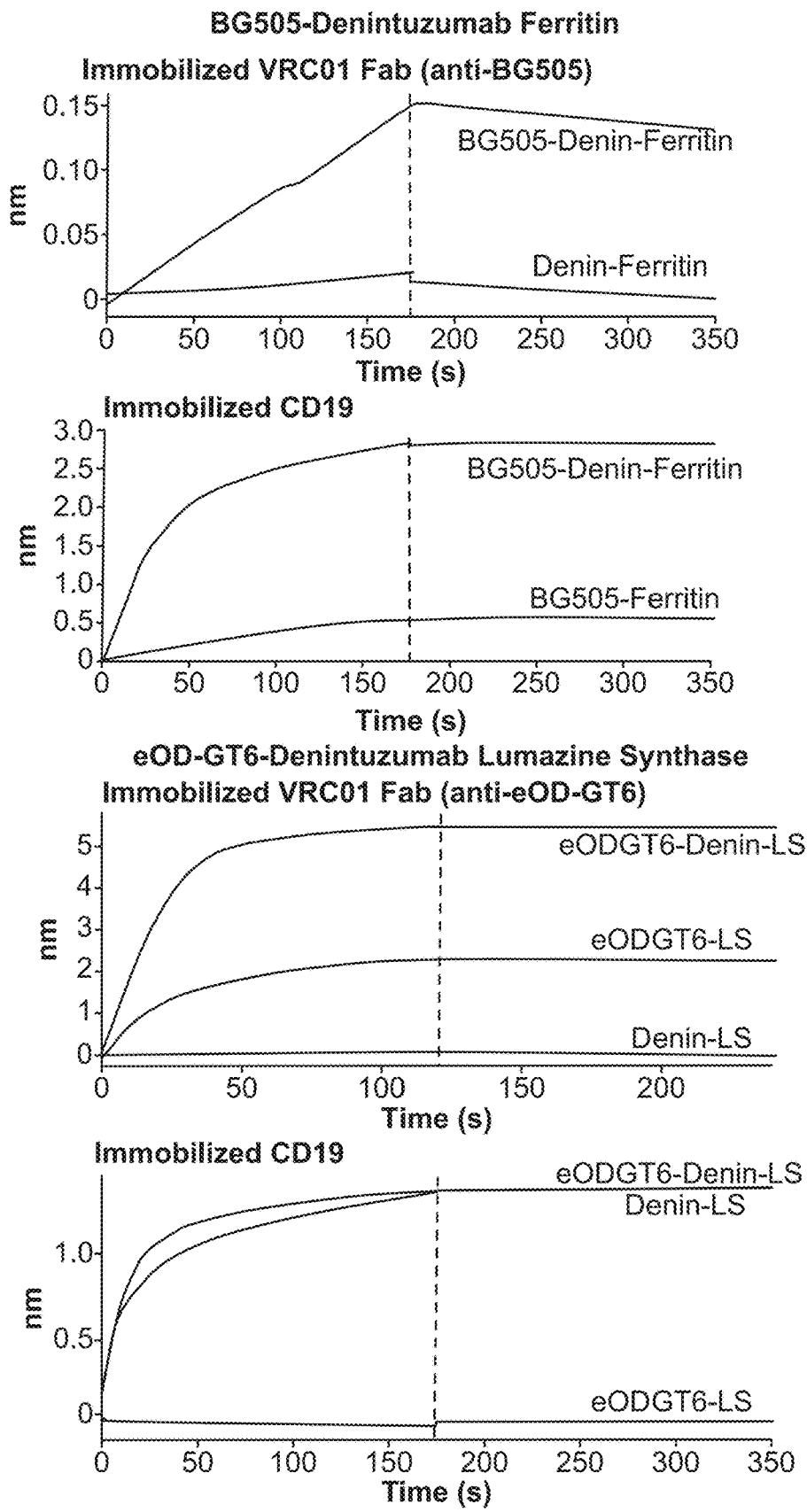
FIG. 22 shows that bi-specific nanoparticles are functional and bind as expected.
Figure 23:
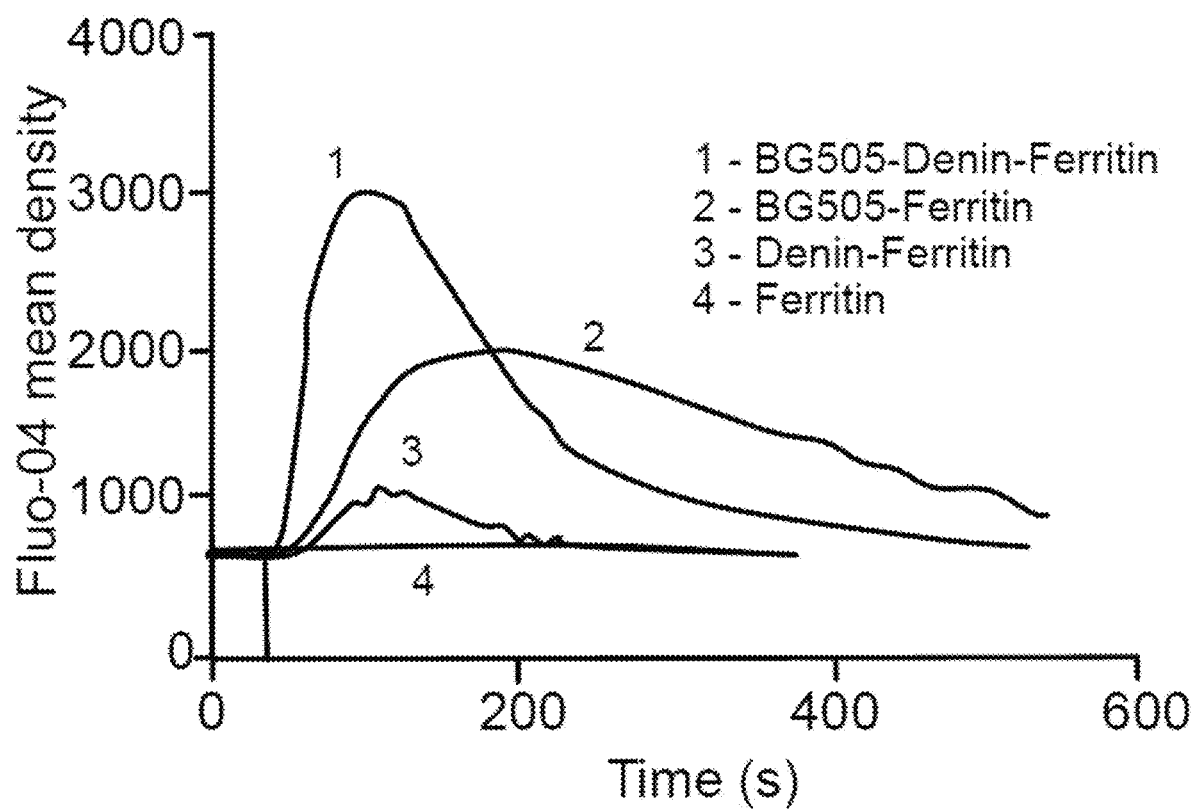
FIG. 23 shows self-adjuvanted nanoparticles are capable of boosting $Ca^{2+}$ dependent B cell activation in comparison to controls

Example 9. Antibody Expressing Fab Nanoparticles Enhance B Cell Activation when Co-Displayed with Antigens BG505 Env SOSIP trimer was cloned to the N terminus of Ferritin using AgeI and XbaI restriction sites. The amino acid sequence of eOD-GT6 was obtained and was added to the C-terminus of lumazine synthase, separated by a GGS4× linker and an NheI restriction site. A StrepTag II was added to the C-terminus of the construct to facilitate affinity purification. The entire construct was codon optimized for mammalian expression, synthesized and cloned into pHLsec expression vector using the restriction enzymes AgeI and XhoI (FIG. 19). Fab HC-nanoparticle, Fab LC and antigen-nanoparticle (where Fab is denintuzumab, antigen is either BG505 SOSIP or eODGT6 and nanoparticle is either ferritin or lumazine synthase) were transiently co-transfected into HEK293F (Thermo Fisher Scientific) as described in previous examples above and purified using identical protocols as described above, with the exception that BG505 containing nanoparticles were also purified by *Galanthus Nivalis* Lectin (GNL) agarose affinity using by a 500 mM sodium chloride wash and 1 M α-methylmannoside elution. Negative stain electron microscopy was as described in previous examples. Biolayer interferometry was as described in previous examples and used CD19mVenus and VRC01 Fab as ligands coated to Ni-NTA and anti-human Fab biosensors to detect binding to denintuzumab-nanoparticles and BG505/eODGT6-nanoparticles, respectively. For calcium flux assays (FIG. 23), Bjab cells (1×10$^6$ cells) were incubated with 1 μM of Fluo-4 dye (Life Technologies) in HBSS for 30 min. Cells were washed twice with 5 mL of 1×PBS, and resuspended in 500 μl of RPMI, on ice. Before acquisition, cells were warmed in a 37° C. bath for 5 min and acquired on high for 30 s on the FITC channel of a BD LSR Fortess Cell Analyzer to establish baseline. Indicated amounts of nanoparticles were then added to the cells and quickly mixed, following which data was acquired for 5-10 min, or until signal returned to baseline. Data was analyzed in FlowJo to establish mean intensity, which was plotted over time.

Example 10: Single-Chain Fc Nanoparticle Design

A single-chain Fc nanoparticle was designed using the following sequence, where bolding indicates the Fc domain, regular font indicates the linker, and underlining represents ferritin:

DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

-continued

CKVSNKALPAPIEKTISKAKGQPREPQVYTLPPSREEMTKNQVSLTCLVK

GFYPSDIAVEWESNGQPENNYKTTPPVLDSDGSFFLYSKLTVDKSRWQQG

NVFSCSVMHEALHNHYTQKSLSLSPGKGGSSGSGSGSTGTSSSGTGTSAG

TTGTSASTSGSGSGGGGSGGGGSAGGTATAGASSGSGSGSGSSSSGGTGD

KTHTCPPCPAPELLGGPSVFLFPPKPKDTLMISRTPEVTCVVVDVSHEDP

EVKFNWYVDGVEVHNAKTKPREEQYNSTYRVVSVLTVLHQDWLNGKEYKC

KVSNKALPAPIEKTISKAKGQPREPQVYTLPPSREEMTKNQVSLTCLVKG

FYPSDIAVEWESNGQPENNYKTTPPVLDSDGSFFLYSKLTVDKSRWQQGN

VFSCSVMHEALHNHYTQKSLSLSPGKSRGGGGSGGSGGSGGS<u>MSSQIRQ</u>

<u>NYSTDVEAAVNSLVNLYLQASYTYLSLGFYFDRDDVALEGVSHFFRELAE</u>

<u>EKREGYERLLKMQNQRGGRALFQDIKKPAEDEWGKTPDAMKAAMALEKKL</u>

<u>NQALLDLHALGSARTDPHLCDFLETHFLDEEVKLIKKMGDHLTNLHRLGG</u>

<u>PEAGLGEYLFERLTLRHD</u>

Figure 24A:
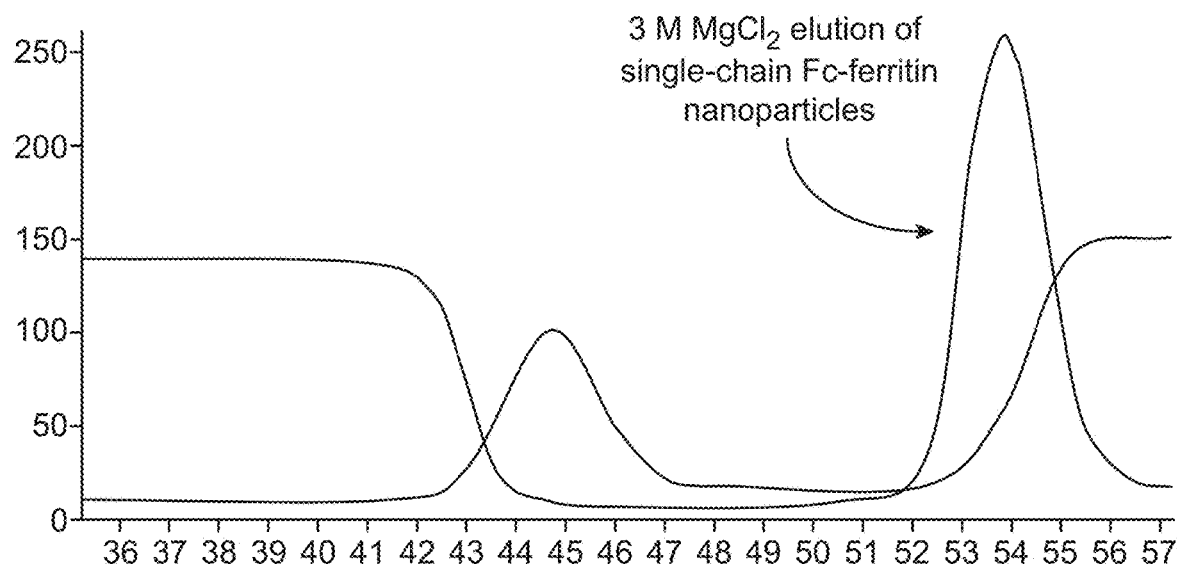
FIGS. 24A and 24B show folding, assembly, and elution data for a single-chain Fc nanoparticle.
Figure 24B:
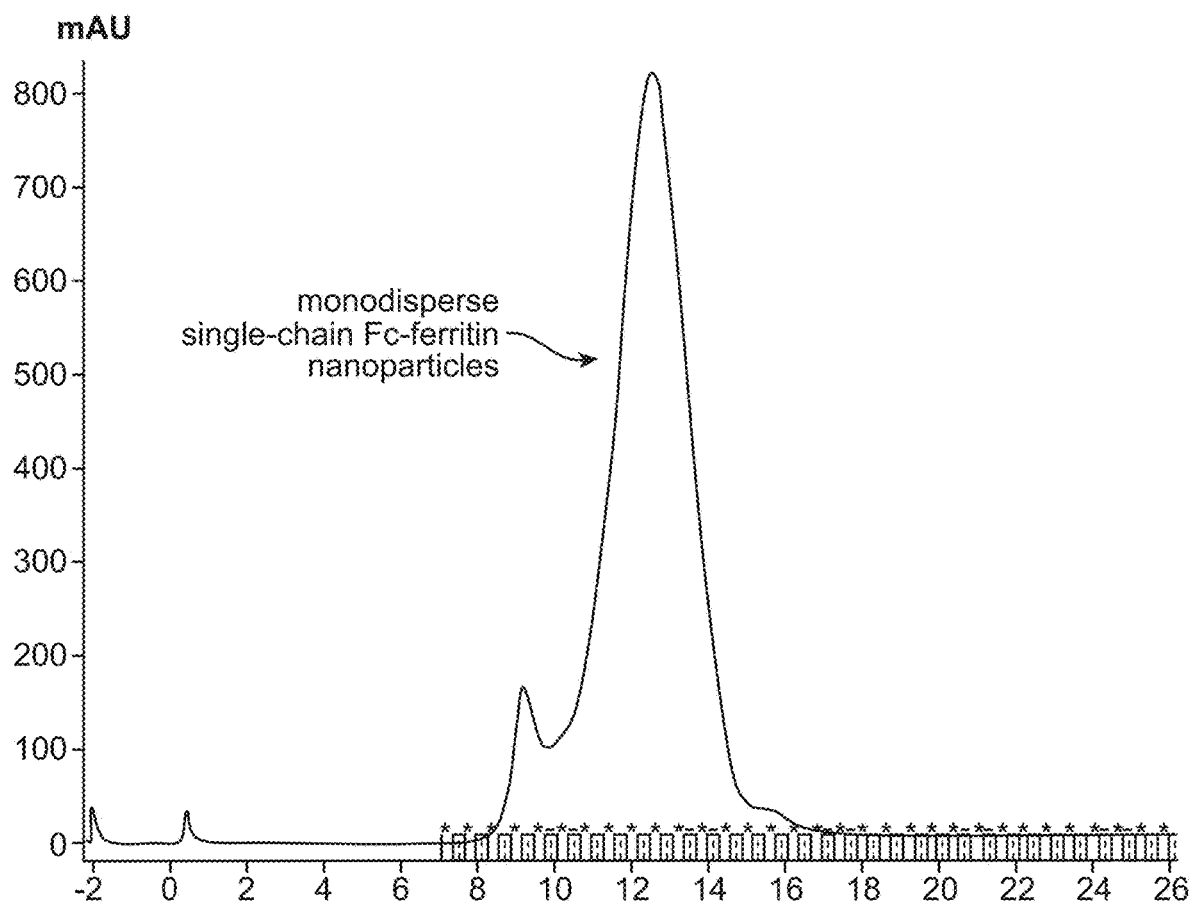

The antibody Fc domain is correctly folded, as shown by its ability to bind to a Protein A column. Elution can be achieved by low pH or by 3 M MgCl2, as shown in FIG. 24. The single-chain Fc nanoparticles are correctly assembled, as shown by a monodisperse peak on size exclusion chromatography.

Example 4: Antihomotypic Affinity Maturation Improves Human B Cell Responses Against a Repetitive Epitope Abstract Affinity maturation selects B cells expressing somatically mutated antibody variants with improved antigen-binding properties to protect from invading pathogens. We determined the molecular mechanism underlying the clonal selection and affinity maturation of human B cells expressing protective antibodies against the circumsporozoite protein of the malaria parasite *Plasmodium falciparum* (PfCSP). We show in molecular detail that the repetitive nature of PfCSP facilitates direct homotypic interactions between two PfCSP repeat-bound monoclonal antibodies, thereby improving antigen affinity and B cell activation. These data provide a mechanistic explanation for the strong selection of somatic mutations that mediate homotypic antibody interactions after repeated parasite exposure in humans. Our findings demonstrate a different mode of antigen-mediated affinity maturation to improve antibody responses to PfCSP and presumably other repetitive antigens.

Materials and Methods

Genotyping

The study was approved by the ethics committee of the medical faculty and the university clinics of the University of Tübingen and strictly adhered to Good Clinical Practice and the principles of the Declaration of Helsinki. The clinical trial from which the samples were obtained was registered under identifier NCT02115516 in the database at clinicaltrials.gov and number 2013-003900-38 in the EudraCT database and carried out under FDA IND 15862 and with approval of the Paul-Ehrlich-Institute (8, 9). Genomic DNA was extracted from whole blood. IGHV3 gene family segments were amplified using barcoded primers. Amplicons were pooled and prepared for sequencing using the TruSeq PCR-free library-prep kit (Illumina). Sequencing was performed on a MiSeq sequencer using a 300-300-bp paired-end protocol. Sequencing reads were assembled using PandaSeq (24) and assigned to the donors by barcode identification.

Site-Directed Mutagenesis

Site-directed mutagenesis on the antibody encoding plasmids was performed using the Q5 sitedirected mutagenesis kit (Qiagen).

Antibody and Fab Production

For IgG production, IGH and IGK variable regions were cloned into expression vectors upstream of human IGK and IGG1 constant regions, respectively, as previously described (25). Recombinant monoclonal antibodies were expressed in HEK293F cells (ThermoFisher Scientific) and antibody concentrations of Protein G Sepharose (GE healthcare)-purified antibodies were determined by ELISA as previously described (9, 10). Fabs were generated by papain digestion of IgG, purified via Protein A chromatography followed by cation-exchange chromatography (MonoS, GE Healthcare) and size-exclusion chromatography (Superdex 200 Increase 10/300 GL, GE Healthcare). For ITC studies, IGH and IGK variable regions were cloned into pcDNA3.4 TOPO expression vectors immediately upstream of human IGK and CH1 constant regions, respectively. Fab were transiently expressed in HEK293F cells (ThermoFisher Scientific) and purified via KappaSelect affinity chromatography (GE Healthcare) and size exclusion chromatography (Superdex 200 Increase 10/300 GL, GE Healthcare).

Antigen Production

ELISAs were performed against NANP5 (Alpha Diagnostic International), NANP3 (PSL GmbH, Heidelberg) or PfCSP with an N-terminal truncation expressed in *E. coli* as previously described (10, 26). For BLI, SEC-MALS and single particle negative-stain EM, full length PfCSP (NF54 strain) was cloned into pcDNA3.4-TOPO for transient expression in HEK293F cells. PfCSP was purified via His-Trap Ni/NTA (GE Healthcare) and size-exclusion chromatography (Superdex 200 Increase 10/300 GL, GE Healthcare).

Surface Plasmon Resonance

Surface plasmon resonance measurements were performed on a BIACORE T200 instrument (GE Healthcare) docked with a series S sensor chip CM5 (GE Healthcare). Ten millimolar HEPES with 150 mM NaCl at pH 7.4 was used as a running buffer as described (9). Anti-human IgG antibodies were immobilized on the chip using an amine-coupling based human antibody capture kit. Equal concentrations of sample antibody and isotype control were captured in the sample and the reference flow cells, respectively. Running buffer was injected for 20 min at a rate of 10 µL/min in order to stabilize the flow cells. NANP3 at 0.015, 0.09, 0.55, 3.3, and 20 UM in running buffer was injected at a rate of 30 µL/min. The flow cells were regenerated with 3 M MgCl2. The data were fit by steady-state kinetic analysis using the BIACORE T200 softwareV2.0.

Crystallization and Structure Determination

Purified 1210 and chimeric H.2140/K. 1210 Fabs were concentrated to 12 mg/ml and diluted to 10 mg/mL with NANP5 (10 mg/mL) and NANP3 (10 mg/mL), respectively, in a 1:5 molar ratio prior to crystallization trials. Purified 1450 Fab and NANP5 were mixed in a 3:1 molar ratio and excess 1450 Fab was purified away via size-exclusion chromatography (Superdex 200 Increase 10/300 GL, GE Healthcare). Purified 1450-NANP5 was then concentrated to 6 mg/mL prior to crystallization trials. 1210-NANP5 co-crystals grew in 20% (w/v) PEG 3350 and 0.2 M sodium citrate and were cryoprotected in 15% (w/v) ethylene glycol. Co-crystals of the chimeric H.2140/K.1210 Fab in complex with NANP3 grew in 20% (w/v) PEG 4000, 0.6 M sodium chloride, and 0.1 M MES pH 6.5 and were cryoprotected in 15% (w/v) glycerol. 1450-NANP5 co-crystals grew in 22.5% (w/v) PEG 3350 and 0.2 M di-ammonium hydrogen citrate and were cryoprotected in 15% (w/v) ethylene glycol. Data were collected at the 08ID-1 beamline at the Canadian Light Source (CLS) or at the 23-ID beamline at the Advanced Photon Source (APS), processed and scaled using XDS (27). The structures were determined by molecular replacement using Phaser (28). Refinement of the structures was carried out using phenix.refine (29) and iterations of refinement using Coot (30). Software were accessed through SBGrid (31).

Isothermal Titration Calorimetry

Calorimetric titration experiments were performed with an Auto-iTC200 instrument (Malvern) at 25° C. Proteins were dialyzed against 20 mM Tris pH 8.0 and 150 mM sodium chloride overnight at 4° C. NANP5 and NANP3 peptides were diluted in dialysis buffer to 2-3 UM and added to the calorimetric cell, which was titrated with 1210, 1210_GL, 1210 H.D100Ymut_K.N92Ymut (1210_YY), and 1210_H.K56_Nrev_K.N93_Srev (1210_NS) Fabs (100 UM) in 15 successive injections of 2.5 µl. Experiments were performed at least three times and the mean and standard error of the mean were reported (FIG. 30). The experimental data were analyzed according to a 1:1 binding model by means of Origin 7.0. Statistical analysis was performed using a one-tailed Mann/Whitney test in Prism.

Biolayer Interferometry Binding Studies

BLI (Octet RED96, ForteBio) experiments were conducted to determine the binding avidity of 1210 and 1210_YY IgG for full length PfCSP. Full-length PfCSP was diluted to 10 µg/mL in kinetics buffer (PBS, pH 7.4, 0.01% (w/v) BSA, and 0.002% Tween20) and immobilized onto Ni/NTA (NTA) biosensors (FortéBio). Following the establishment of a stable baseline with loaded ligand in kinetics buffer, biosensors were dipped into wells containing twofold dilution series of IgG. Tips were then dipped back into kinetics buffer to monitor the dissociation rate. Kinetics data were analyzed using ForteBio's Data Analysis software 9.0, and curves were fitted to a 1:1 binding model.

Size-Exclusion Chromatography-Multi-Angle Light Scattering (SEC/MALS)

NANP5 peptide was co-complexed with a threefold molar excess of 1210 Fab and loaded on a Superdex 200 Increase 10/300 GL (GE Healthcare), coupled in-line to an AKTA Pure chromatography system (GE Healthcare) with the following calibrated detection systems: (i) MiniDawn Treos MALS detector (Wyatt); (ii) Quasielastic light scattering (QELS) detector (Wyatt); and (iii) Optilab T-rex refractive index (RI) detector (Wyatt). Three hundred thirty micrograms of full-length PfCSP was loaded on a Superdex 200 Increase 10/300 GL (GE Healthcare), coupled in-line with an Agilent Technologies 1260 Infinity II HPLC with the detection systems described above. Full-length PfCSP (5 UM) was co-complexed with a 20-fold molar excess of 1210 Fab (100 UM) and either 100 UL or 400 µL was loaded on a Superose 6 Increase 10/300 GL (GE Healthcare) in-line with an Agilent Technologies 1260 Infinity II HPLC with the detection systems described above. Data processing was performed using the ASTRA software (Wyatt).

Negative-Stain Transmission Electron Microscopy 400 mesh Cu grids were coated with colloidon and a thin continuous layer of carbon was evaporated onto the grids. Carbon grids were glow discharged according to standard protocols. A 3-µL drop of co-complexed 1210 Fabs with full-length PfCSP was applied to a glow-discharged carbon grid. After 20 s, the grid was blotted and 3 µL of 1% (w/v) uranyl formate solution was added three times for two lots of 5 s and a final 18 s, with blots in between. Data were collected on a FEI Tecnai 20 operated at 200 kV. One hundred twenty images were collected with a defocus value between 1 and 3 µm. Initially, a total of 1080 particle images were manually selected with Relion 2.0 (32) and 2D classification of particle images was performed with 10 classes allowed. Subsequently, the best six 2D classes comprising 947 particle images were used for autopicking 13,146 particle images from 120 micrographs and 2D classification was performed with 50 classes allowed.

Retroviral Transduction of TKO-EST Cells

Triple Rag2, λ5, and SLP-65 TKO-EST deficient murine pre-B cells, which lack endogenous BCR expression, were reconstituted with Ig heavy and light chain genes via retroviral transduction (33). For the generation of viral particles, constructs encoding complete IGHM and IGK variable regions were cloned into the pMIZCC and pMIZYN vector backbones (34). $1.8 \times 10^5$ Phoenix-Eco viral packaging cells per well were seeded into six-well culture plates in complete Iscove's modified Dulbecco's medium (IMDM, including 5% FCS, 2 mM Lglutamine, 0.5 mL β-mercaptoethanol, and penicillin/streptomycin). Twenty-four hours later, cells were transfected with 0.5 µg of heavy-chain and 0.5 µg of light-chain plasmid, in 100 µl of pure IMDM using 3 µl of GeneJuice reagent and incubated for 48 h at 37° C. and 8% $CO_2$. Supernatants were harvested and viral particles were purified using a 0.45-µm filter. 1 µl/mL of polybrene was added to the viral particle suspension. In parallel, $2 \times 10^5$ TKO-EST cells were transferred into a 1.5-mL tube and centrifuged (366×g, 4° C., 5 min). The supernatant was discarded and the cell pellet was resuspended in 800 µl of the viral particle suspension. TKO-EST cells were spin-transduced at 366×g and 37° C. After 3 h, the medium was replaced with fresh complete IMDM supplemented with IL-7 and the cells were seeded into six-well plates.

Ca2+ Flux Measurement

Ca2+ flux was measured as described in (33). After viral transduction, $1 \times 10^6$ TKO-EST cells were loaded for 45 min at 37° C. with the calcium-sensitive dye Indo-1 AM (Molecular Probes). The Indo-1 staining solution was prepared by mixing 25 µl of the Indo-1 stock solution (prepared by diluting 50 µg of Indo-1 in 25 µl of DMSO) with 25 µl pluronic acid F-127 and 113 µl of FCS and incubated (5 min, darkness, RT). Indo-loaded cells were washed in 5 mL of 1% FCS IMDM, resuspended in 500 µl of 1% FCS IMDM and transferred into FACS tubes. Each sample was pre-warmed individually for 10 min at 37° C. on a hotplate before measurement. After recording the Ca2+flux baseline on a LSR cytometer for 30 s, 5 µl of the antigen solution containing 4-hydroxytamoxifen (4-OHT, final concentration: 2 µM) was added and the Ca2+flux in response to antigen was recorded for 6 min. Surface Ig expression in the different cell lines was comparable when measured in FACS by binding of anti-IgM and anti-Igκ fluorescently labelled antibodies. Comparable functionality of all cell lines was confirmed upon stimulation with 4-OHT and the α-Igκ antibody (1 µg/mL).

Pf Traversal Assay

Pf traversal assays were performed in 96-well-plate format as described (9, 10). In brief, 75,000 Pf sporozoites obtained from female *Anopheles coluzzii* mosquito salivary glands were preincubated with different concentrations of monoclonal antibodies for 30 min before incubation with HC-04 human hepatocyte cells in the presence of 0.5 mg/mL dextran/rhodamine (Molecular Probes). Untreated sporozoites and dextran/rhodamine alone were used as positive control and to determine the experimental background signal, respectively. Upon fixation with 1% paraformaldehyde (PFA), the percentage of dextran-positive (i.e., traversed cells) was measured using an LSR II flow cytometer. The background signal was subtracted from all measurements. Traversal inhibition was determined based on the traversal rate observed for untreated sporozoites. Data for each antibody was pooled from at least three independent experiments and the titration curve fitted using a three-parametric Hill function.

preerythrocytic vaccine development (7). We recently showed that the anti-NANP PfCSP memory B cell response in Pf-naïve volunteers after repeated exposure to live Pf sporozoites under chloroquine prophylaxis matured predominantly through the clonal selection and expansion of potent Pf inhibitory IGHV3-33 and IGKV1-5-encoded germline antibodies with 8-amino-acid (aa)-long immunoglobulin (Ig) K complementarity determining region (CDR) 3 (KCDR3: 8) (8, 9).

Here, we analyzed five representative germline or low-mutated antibodies with reported affinities to a NANP 5-mer peptide (NANP5) between $10^{-6}$ and $10^{-9}$ M (FIG. 25A and Table 1) (9). Antigen binding was abrogated when the original Ig Vκ1-5 was replaced by Vκ2-28, or when the native Ig heavy (IgH) chains were paired with a Vκ1-5 light chain with 9-aalong KCDR3 (FIG. 25B), demonstrating the importance of these specific Ig gene features in antigen recognition.

TABLE 1

VH3-33/VK1-5/K: 8 antibody genes features.

| mAb | IGHV | IGHJ | H CDR3 | IGKV | IGKJ | KCDR3 | Isotype | Replacement SHM H | Replacement SHM K |
|---|---|---|---|---|---|---|---|---|---|
| 2290 | IGHV3-33 | IGHJ3 | ARVQDSEDYGGNSGAFDI (SEQ ID NO: 7) | IGKV1-5 | IGKJ4 | QQYNSYFT | IGHM | 0 | 0 |
| 1210 | IGHV3-33 | IGHJ3 | ARVRDSSDYYGDAFDI (SEQ ID NO: 8) | IGKV1-5 | IGKJ1 | QQYNNYWT | IGHM | 1 | 3 |
| 2163 | IGHV3-33 | IGHJ4 | ARVQTTTGGGSCCPFDY (SEQ ID NO: 9) | IGKV1-5 | IGKJ1 | QQYNSYWT | IGHM | 0 | 0 |
| 2219 | IGHV3-33 | IGHJ3 | ARVQDSEDYGGNSGVFDI (SEQ ID NO: 10) | IGKV1-5 | IGKJ4 | QQYNSYFT | IGHM | 4 | 1 |
| 2140 | IGHV3-33 | IGHJ5 | AKVGEGQVGDSSGYYDH (SEQ ID NO: 11) | IGKV1-5 | IGKJ5 | QQYKSFWT | IGHG1 | 4 | 1 |

Mouse Immunizations and Infections

All animal experiments were approved by LAGeSo, Berlin, Germany (H0027/12). Immunizations and infections were performed as previously described (9, 10). In brief, 8-weekold C57BL/6 female mice (5 per group) were passively immunized intraperitoneally with 100 µg or 30 µg of monoclonal human anti-PfCSP antibody or an isotype control (mGO53 (35)) in 100 µl of PBS. Twenty-four hours post passive immunization, mice were infected with 5,000 PfCSP transgenic *Plasmodium berghei* (Pb-PfCSP) (10) sporozoites by subcutaneous injection at the tail base. Giemsa-stained blood smears were analyzed daily from day 3 to day 12 post-infection. At least 100 microscopic fields were counted to declare parasite positivity.

Results and Discussion

Sporozoites of the human malaria parasite *Plasmodium falciparum* (Pf) express a surface protein, circumsporozoite protein (PfCSP), with an immunodominant central NANP repeat region (1-3). Antibodies against the repeat can mediate protection from Pf infection in animal models (4-6). However, anti-NANP antibody-mediated protection is not readily achieved through vaccination. Thus, the induction of protective PfCSP NANP antibodies is a major goal in All VH3-33/Vk1-5/KCDR3: 8 antibodies were encoded by the IGHV3-33*01 allele (9). IGHV3-33*01 differs from three otherwise highly similar gene segments (IGHV3-30, IGHV3-30-3, and IGHV3-30-5) at position 52 of the IgH CDR (HCDR) 2, which strictly encodes for a tryptophan and not serine or arginine (Table 2 and Table 3). H.W52_S and H.W52_R mutants of the selected antibodies, including a H.W52_A mutant in antibody 2140, and a double mutant (H.W52_R, H.V50_F) to mimic the IGHV3-30*02 and IGHV3-30-5*02 alleles, all showed reduced PfCSP repeat reactivity associated with reduced in vitro parasite inhibitory activity (FIGS. 25, C and D).

TABLE 2

HCDR2 residues encoded by different IGHV3-33, IGHV3-30, IGHV3-30-3, and IGHV3-30-5 alleles.

| Gene* | Allele(s)* | 50 | 51 | 52 | 52A |
|---|---|---|---|---|---|
| IGHV3-33 | 01, 02, 03, 04, 06 | V | I | W | Y |
| IGHV3-33 | 05 | V | I | S | Y |

TABLE 2-continued

HCDR2 residues encoded by different IGHV3-33, IGHV3-30, IGHV3-30-3, and IGHV3-30-5 alleles.

| Gene* | Allele(s)* | 50 | 51 | 52 | 52A |
|---|---|---|---|---|---|
| IGHV3-30 | 01, 03, 04, 05, 06, 07, 08, 09, 10, 11, 12, 13, 14, 15, 16, 17, 18, 19 | V | I | S | Y |
| IGHV3-30-3 | 01, 02, 03 | V | I | S | Y |
| IGHV3-30-5 | 01 | V | I | S | Y |

*According to IMGT ®, the international ImMunoGeneTics information system ®.

TABLE 3

Amino acid sequence of VH3-33, VH3-30, VH3-30-3, VH3-30-5
CLUSTAL 0 (1.2.4) multiple sequence alignment

| | | |
|---|---|---|
| AB019439\|IGHV3-33*01\| | QVQLVESGGGVVQPGRSLRLSCAASGFTFSSYGMHWVRQAPGKGLEWVAVIWYDGSNKYY | 60 (SEQ ID NO: 12) |
| M99665\|IGHV3-33*02\| | QVQLVESGGGVVQPGRSLRLSCAASGFTFSSYGMHWVRQAPGKGLEWVAVIWYDGSNKYY | 60 (SEQ ID NO: 12) |
| M77305\|IGHV3-33*03\| | QVQLVESGGGVVQPGRSLRLSCAASGFTFSSYGMHWVRQAPGKGLEWVAVIWYDGSNKYY | 60 (SEQ ID NO: 12) |
| M77335\|IGHV3-33*04\| | QVQLVESGGGVVQPGRSLRLSCAASGFTFSSYGMHWVRQAPGKGLEWVAVIWYDGSNKYY | 60 (SEQ ID NO: 12) |
| M77334\|IGHV3-33*05\| | QVQLVESGGGVVQPGRSLRLSCAASGFTFSSYGMHWVRQAPGKGLEWVAVISYDGSNKYY | 60 (SEQ ID NO: 13) |
| HM855436\|IGHV3-33*06\| | QVQLVESGGGVVQPGRSLRLSCAASGFTFSSYGMHWVRQAPGKGLEWVAVIWYDGSNKYY | 60 (SEQ ID NO: 12) |
| M83134\|IGHV3-30*01\| | QVQLVESGGGVVQPGRSLRLSCAASGFTFSSYAMHWVRQAPGKGLEWVAVISYDGSNKYY | 60 (SEQ ID NO: 14) |
| L26401\|IGHV3-30*02\| | QVQLVESGGGVVQPGSLRLSCAASGFTFSSYGMHWVRQAPGKGLEWVAFIRYDGSNKYY | 60 (SEQ ID NO: 15) |
| M99663\|IGHV3-30*03\| | QVQLVESGGGVVQPGRSLRLSCAASGFTFSSYGMHWVRQAPGKGLEWVAVISYDGSNKYY | 60 (SEQ ID NO: 13) |
| L06615\|IGHV3-30*04\| | QVQLVESGGGVVQPGRSLRLSCAASGFTFSSYAMHWVRQAPGKGLEWVAVISYDGSNKYY | 60 (SEQ ID NO: 14) |
| M77323\|IGHV3-30*05\| | QVQLVESGGGVVQPGRSLRLSCAASGFTFSSYGMHWVRQAPGKGLEWVAVISYDGSNKYY | 60 (SEQ ID NO: 13) |
| L06617\|IGHV3-30*06\| | QVQLVESGGGVVQPGRSLRLSCAASGFTFSSYGMHWVRQAPGKGLEWVAVISYDGSNKYY | 60 (SEQ ID NO: 13) |
| L06614\|IGHV3-30*07\| | QVQLVESGGGVVQPGRSLRLSCAASGFTFSSYAMHWVRQAPGKGLEWVAVISYDGSNKYY | 60 (SEQ ID NO: 14) |
| M62737\|IGHV3-30*08\| | QVQLVDSGGGVVQPGRSLRLSCAASAFTFSSYAMHWVRQAPGKGLEWVAVISYDGSNKYY | 60 (SEQ ID NO: 16) |
| M77300\|IGHV3-30*09\| | QVQLVESGGGVVQPGRSLRLSCAASGFTFSSYAMHWVRQAPGKGLEWVAVISYDGSNKYY | 60 (SEQ ID NO: 14) |
| M77326\|IGHV3-30*10\| | QVQLVESGGGVVQPGRSLRLSCAASGFTFSSYAMHWVRQAPGKGLEWVAVISYDGSNKYY | 60 (SEQ ID NO: 14) |
| M77331\|IGHV3-30*11\| | QVQLVESGGGVVQPGRSLRLSCAASGFTFSSYAMHWVRQAPGKGLEWVAVISYDGSNKYY | 60 (SEQ ID NO: 14) |
| M77338\|IGHV3-30*12\| | QVQLVESGGGVVQPGRSLRLSCAASGFTFSSYGMHWVRQAPGKGLEWVAVISYDGSNKYY | 60 (SEQ ID NO: 13) |
| M77339\|IGHV3-30*13\| | QVQLVESGGGVVQPGRSLRLSCAASGFTFSSYGMHWVRQAPGKGLEWVAVISYDGSNKYY | 60 (SEQ ID NO: 13) |
| M77324\|IGHV3-30*14\| | QVQLVESGGGVVQPGRSLRLSCAASGFTFSSYAMHWVRQAPGKGLEWVAVISYDGSNKYY | 60 (SEQ ID NO: 14) |
| M77327\|IGHV3-30*15\| | QVQLVESGGGVVQPGRSLRLSCAASGFTFSSYAMHWVRQAPGKGLEWVAVISYDGSNKYY | 60 (SEQ ID NO: 14) |
| M77328\|IGHV3-30*16\| | QVQLVESGGGVVQPGRSLRLSCAASGFTFSSYAMHWVRQAPGKGLEWVAVISYDGSNKYY | 60 (SEQ ID NO: 14) |
| M77329\|IGHV3-30*17\| | QVQLVESGGGVVQPGRSLRLSCAASGFTFSSYAMHWVRQAPGKGLEWVAVISYDGSNKYY | 60 (SEQ ID NO: 14) |
| X92214\|IGHV3-30*18\| | QVQLVESGGGVVQPGRSLRLSCAASGFTFSSYGMHWVRQAPGKGLEWVAVISYDGSNKYY | 60 (SEQ ID NO: 13) |
| L06616\|IGHV3-30*19\| | QVQLVESGGGVVQPGRSLRLSCAASGFTFSSYGMHWVRQAPGKGLEWVAVISYDGSNKYY | 60 (SEQ ID NO: 13) |
| AC244456\|IGHV3-30-3*01\| | QVQLVESGGGVVQPGRSLRLSCAASGFTFSSYAMHWVRQAPGKGLEWVAVISYDGSNKYY | 60 (SEQ ID NO: 14) |
| M77302\|IGHV3-30-3*02\| | QVQLVESGGGVVQPGRSLRLSCAASGFTFSSYAMHWVRQAPGKGLEWVAVISYDGSNKYY | 60 (SEQ ID NO: 14) |
| KC713945\|IGHV3-30-3*03\| | QVQLVESGGGVVQPGRSLRLSCAASGFTFSSYAMHWVRQAPGKGLEWVAVISYDGSNKYY | 60 (SEQ ID NO: 14) |
| AC244456\|IGHV3-30-5*01\| | QVQLVESGGGVVQPGRSLRLSCAASGFTFSSYGMHWVRQAPGKGLEWVAVISYDGSNKYY | 60 (SEQ ID NO: 13) |

TABLE 3-continued

Amino acid sequence of VH3-33, VH3-30, VH3-30-3, VH3-30-5
CLUSTAL O (1.2.4) multiple sequence alignment

| | | | |
|---|---|---|---|
| AC245243\|IGHV3-30-5*02\| | QVQLVESGGGVVQPGGSLRLSCAASGFTFSSYGMHWVRQAPGKGLEWVAIRYDGSNKYY<br>**.***** ****.**.**************.* ******** | 60 | (SEQ ID NO: 15) |
| AB019439\|IGHV3-33*01\| | ADSVKGRFTISRDNSKNTLYLQMNSLRAEDTAVYYCAR | 38 | (SEQ ID NO: 17) |
| M99665\|IGHV3-33*02\| | ADSAKGRFTISRDNSNTLLQMNSLRAEDTAVYYCAR | 38 | (SEQ ID NO: 18) |
| M77305\|IGHV3-33*03\| | ADSVKGRFTISRDNSKNTLYLQMNSLRAEDTAVYYCAK | 38 | (SEQ ID NO: 19) |
| M77335\|IGHV3-33*04\| | ADSVKGRFTISRDNSKNTLYLQMNSLRAEDTAVYYCAR | 38 | (SEQ ID NO: 17) |
| M77334\|IGHV3-33*05\| | ADSVKGRFTISRDNSKNTLYLQMNSLRAEDTAVYYCAR | 38 | (SEQ ID NO: 17) |
| HM855436\|IGHV3-33*06\| | ADSVKGRFTISRDNSKNTLYLQMNSLRAEDTAVYYCAK | 38 | (SEQ ID NO: 19) |
| M83134\|IGHV3-30*01\| | ADSVKGRFTISRDNSKNTLYLQMNSLRAEDTAVYYCAR | 38 | (SEQ ID NO: 17) |
| L26401\|IGHV3-30*02\| | ADSVKGRFTISRDNSKNTLYLQMNSLRAEDTAVYYCAK | 38 | (SEQ ID NO: 19) |
| M99663\|IGHV3-30*03\| | ADSVKGRFTISRDNSKNTLYLQMNSLRAEDTAVYYCAR | 38 | (SEQ ID NO: 17) |
| L06615\|IGHV3-30*04\| | ADSVKGRFTISRDNSKNTLYLQMNSLRAEDTAVYYCAR | 38 | (SEQ ID NO: 17) |
| M77323\|IGHV3-30*05\| | ADSVKGRFTISRDNSKNTLYLQMNSLRAEGTAVYYCAR | 38 | (SEQ ID NO: 20) |
| L06617\|IGHV3-30*06\| | ADSVKGRFTISRDNSKNTLYLQMNSLRAEDTAVYYCAR | 38 | (SEQ ID NO: 17) |
| L06614\|IGHV3-30*07\| | ADSVKGRFTISRDNSKNTLYLQMNSLRAEDTAVYYCAR | 38 | (SEQ ID NO: 17) |
| M62737\|IGHV3-30*08\| | ADSVKGRFTISRDNSKNTLYLQMNSLRAEDTAVYYCAR | 38 | (SEQ ID NO: 17) |
| M77300\|IGHV3-30*09\| | ADSVKGRFAISRDNSKNTLYLQMNSLRAEDTAVYYCAR | 38 | (SEQ ID NO: 21) |
| M77326\|IGHV3-30*10\| | TDSVKGRFTISRDNSKNTLYLQMNSLRAEDTAVYYCAR | 38 | (SEQ ID NO: 22) |
| M77331\|IGHV3-30*11\| | ADSVKGRFTISRDNSKNTLYLQMNSLRAEDTAVYYCAR | 38 | (SEQ ID NO: 17) |
| M77338\|IGHV3-30*12\| | ADSVKGRFTISRDNSKNTLYLQMNSLRAEDTAVYYCAR | 38 | (SEQ ID NO: 17) |
| M77339\|IGHV3-30*13\| | ADSVKGRFTISRDNSKNRLYLQMNSLRAEDTAVYYCAR | 38 | (SEQ ID NO: 23) |
| M77324\|IGHV3-30*14\| | ADSVKGRFTISRDNSKNTLYLQMNSLRAEDTAVYYCAR | 38 | (SEQ ID NO: 17) |
| M77327\|IGHV3-30*15\| | ADSVKGRFTISRDNSKNTLYLQMSSLRAEDTAVYYCAR | 38 | (SEQ ID NO: 24) |
| M77328\|IGHV3-30*16\| | ADSVKGRFTISRDNSKNTLYLQMNSLRAEDTAVYYCAR | 38 | (SEQ ID NO: 17) |
| M77329\|IGHV3-30*17\| | ADSVKGRFTISRDNSKNTLYLQMNSLRAEDTAVYYCAR | 38 | (SEQ ID NO: 17) |
| X92214\|IGHV3-30*18\| | ADSVKGRFTISRDNSKNTLYLQMNSLRAEDTAVYYCAK | 38 | (SEQ ID NO: 19) |
| L06616\|IGHV3-30*19\| | ADSVKGRFTISRDNSKNTLYLQMNSLRAEDTAVYYCAR | 38 | (SEQ ID NO: 17) |
| AC244456\|IGHV3-30-3*01\| | ADSVKGRFTISRDNSKNTLYLQMNSLRAEDTAVYYCAR | 38 | (SEQ ID NO: 17) |
| M77302\|IGHV3-30-3*02\| | ADSVKGRFTISRDNSKNTLYLQMNSLRAEDTAVYYCAK | 38 | (SEQ ID NO: 19) |
| KC713945\|IGHV3-30-3*03\| | ADSVKGRFTISRDNSKNTLYLQMNSLRAEDTAVYYCAR | 38 | (SEQ ID NO: 17) |
| AC244456\|IGHV3-30-5*01\| | ADSVKGRFTISRDNSKNTLYLQMNSLRAEDTAVYYCAK | 38 | (SEQ ID NO: 19) |
| AC245243\|IGHV3-30-5*02\| | ADSVKGRFTISRDNSKNTLYLQMNSLRAEDTAVYYCAK<br>:..****.* *:*.* *****: | 38 | (SEQ ID NO: 19) |

The majority of NANP-reactive VH3-33/Vκ1-5/KCDR3: 8 B cells belonged to clonally expanded and somatic hypermutation (SHM)-diversified cell clusters with strong selection for replacement mutations in HCDR1 (H.S31) and HCDR2 (H.V50, H.N56), as well as KCDR3 (K.S93), likely as a result of affinity maturation (FIGS. 25, E and F) (9). The introduction of missing mutations (mut) or reversions (rev) at positions H.V50 and, to a lesser extent, H.S31 revealed a role in binding to a minimal NANP3 peptide (10, 11) as demonstrated for the germline antibody 2163 and the low-mutated antibody 1210 (FIGS. 25, G and H, and table 4). In contrast, exchanges at positions H.N56 and K.S93, either alone (1210_H.K56_Nrev, 1210_K.N93_Srev, 2163_H.N56_Kmut) or in combination (1210_NS, 2163_KN), showed no significant effect (FIGS. 25, G and H, and Table 4). Thus, affinity maturation to the repeat explained the strong selection for only two of the four characteristic replacement mutations in VH3-33/Vκ1-5/KCDR3: 8 anti-NANP antibodies.

TABLE 4

IgH and IgK amino acid sequence of 1210 and 2163 antibody variants

| 1210 variants IgH | | H.31 | H.50 | H.56 | | |
|---|---|---|---|---|---|---|
| 1210_GL | ------IGHV3-33*01--- | | | | ------IGHJ3*02 | |
| 1210 | QVQLVESGGGVVQPGRSLRLSCAASGFTFSSYGMHWVRQAPGKGLEWVAVIWYDGSNKYYADSVKGRFTISRDNSKNTLYLQMNSLRAEDTAVYYCARVRDSSDYYGDAFDIWGQGTMVTVSS (SEQ ID NO: 25) | | | | | |
| 1210_H.V50_I$^{mut}$ | QVQLVESGGGVVQPGRSLRLSCAASGFTFSSYGMHWVRQAPGKGLEWVAIIWYDGSNKYYADSVKGRFTISRDNSKNTLYLQMNSLRAEDTAVYYCARVRDSSDYYGDAFDIWGQGTMVTVSS (SEQ ID NO: 26) | | | | | |
| 1210_H.N31_S$^{rev}$ | QVQLVESGGGVVQPGRSLRLSCAASGFTFSSYGMHWVRQAPGKGLEWVAVIWYDGSNKYYADSVKGRFTISRDNSKNTLYLQMNSLRAEDTAVYYCARVRDSSDYYGDAFDIWGQGTMVTVSS (SEQ ID NO: 27) | | | | | |
| 1210_H.K56_N$^{rev}$ | QVQLVESGGGVVQPGRSLRLSCAASGFTFSSYGMHWVRQAPGKGLEWVAVIWYDGSNKYYADSVKGRFTISRDNSKNTLYLQMNSLRAEDTAVYYCARVRDSSDYYGDAFDIWGQGTMVTVSS (SEQ ID NO: 28) | | | | | |
| 1210_H.K56_N$^{rev}$_K.N93_S$^{rev}$ | QVQLVESGGGVVQPGRSLRLSCAASGFTFSSYGMHWVRQAPGKGLEWVAVIWYDGSNKYYADSVKGRFTISRDNSKNTLYLQMNSLRAEDTAVYYCARVRDSSDYYGDAFDIWGQGTMVTVSS (SEQ ID NO: 29) | | | | | |
| Named 1210 NS | QVQLVESGGGVVQPGRSLRLSCAASGFTFSSYGMHWVRQAPGKGLEWVAVIWYDGSNKYYADSVKGRFTISRDNSKNTLYLQMNSLRAEDTAVYYCARVRDSSDYYGDAFDIWGQGTMVTVSS (SEQ ID NO: 29) | | | | | |
| 1210_H.D104Y N$^{mut}$_K.N92_Y$^{mut}$ | QVQLVESGGGVVQPGRSLRLSCAASGFTFSSYGMHWVRQAPGKGLEWVAVIWYDGSNKYYADSVKGRFTISRDNSKNTLYLQMNSLRAEDTAVYYCARVRDSSDYYYGDAFDIWGQGTMVTVSS (SEQ ID NO: 30) | | | | | |
| Named 1210 YY | | | | | | |

| 1210 variants IgK | | | K.93 | | |
|---|---|---|---|---|---|
| 1210_GL | ------IGKV1-5*03------ | | | ------IGKJ1*01 | |
| 1210 | DIQMTQSPSTLSASVGDRVTITCRASQSISSWLAWYQQKPGKAPKLLIYKASSLESGVPSRFSGSGSGTEFTLTISSLQPDDFATYYCQQYNSYWTFGQGTKVEIK (SEQ ID NO: 31) | | | | |
| 1210_H.V50_I$^{mut}$ | DIQMTQSPSTLSASVGDRVTITCRASQSISSWLAWYQQKPGKAPKLLIYKASSNLESGVPNSRFSGSGSGTEFTLTISSLQPDDFATYYCQQYNNYWTFGQGTKVEIK (SEQ ID NO: 32) | | | | |
| 1210_H.N31_S$^{rev}$ | DIQMTQSPSTLSASVGDRVTITCRASQSISSWLAWYQQKPGKAPKLLIYKASNLESGVPLRFSGSGSGTEFTLTISSLQPDDFATYYCQQYNNYWT**FGQGTKVEIK (SEQ ID NO: 32) | | | | |
| 1210_H.K56_N$^{rev}$ | DIQMTQSPSTLSASVGDRVTITCRASQSISSWLAWYQQKPGKAPKLLIYKASNLESGVPLRFSGSGSGTEFTLTISSLQPDDFATYYCQQYTNYWT**FGQGTKVEIK (SEQ ID NO: 32) | | | | |
| 1210_H.K56_N$^{rev}$_K.N93_S$^{rev}$ | DIQMTQSPSTLSASVGDRVTITCRASQSISSWLAWYQQKPGKAPKLLIYKASNLESGVPLRFSGSGSGTEFTLTISSLQPDDFATYYCQQYNSYWT**FGQGTKVEIK (SEQ ID NO: 33) | | | | |
| Named 1210 NS | DIQMTQSPSTLSASVGDRVTITCRASQSISSWLAWYQQKPGKAPKLLIYKASNLESGVPLRFSGSGSGTEFTLTISSLQPDDFATYYCQQYNSYWT**FGQGTKVEIK (SEQ ID NO: 33) | | | | |
| 1210_H.D104Y N$^{mut}$_K.N92_Y$^{mut}$ | DIQMTQSPSTLSASVGDRVTITCRASQSISSWLAWYQQKPGKAPKLLIYKASNLESGVPLRFSGSGSGTEFTLTISSLQPDDFATYYCQQYYNYWT**FGQGTKVEIK (SEQ ID NO: 34) | | | | |
| Named 1210 YY | | | | | |

| 2163 variants IgH | | H.31 | H.50 | H.56 | | |
|---|---|---|---|---|---|---|
| 2163 | ------IGHV3-33*01--- | | ---D---- | | ------IGHJ3*02 | |
| 2163_H.V50_I$^{mut}$ | QVQLVESGGGVVQPGRSLRLSCAASGFTFSSYGMHWVRQAPGKGLEWVAVIWYDGSNKYYADSVKGRFTISRDNSKNTLYLQMNSLRAEDTAVYYCARVQTTTGGGSCCPFDY**WGQGTLVTVSS (SEQ ID NO: 35) | | | | | |
| 2163_H.S31_N$^{mut}$ | QVQLVESGGGVVQPGRSLRLSCAASGFTFSSYGMHWVRQAPGKGLEWVAIIWYDGSNKYYADSVKGRFTISRDNSKNTLYLQMNSLRAEDTAVYYCARVQTTTGGGSCCPFDY**WGQGTLVTVSS (SEQ ID NO: 36) | | | | | |
| 2163_H.N56_K$^{mut}$ | QVQLVESGGGVVQPGRSLRLSCAASGFTFSNYGMHWVRQAPGKGLEWVAVIWYDGSNKYYADSVKGRFTISRDNSKNTLYLQMNSLRAEDTAVYYCARVQTTTGGGSCCPFDY**WGQGTLVTVSS (SEQ ID NO: 37) | | | | | |
| | QVQLVESGGGVVQPGRSLRLSCAASGFTFSSYGMHWVRQAPGKGLEWVAVIWYDGKKYYADSVKGRFTISRDNSKNTLYLQMNSLRAEDTAVYYCARVQTTTGGGSCCPFDY**WGQGTLVTVSS (SEQ ID NO: 38) | | | | | |

TABLE 4-continued

IgH and IgK amino acid sequence of 1210 and 2163 antibody variants

Figure 26A:
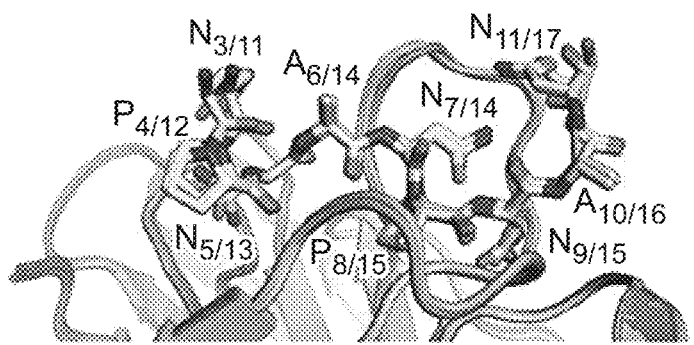
FIGS. 26A, 26B, 26C, 26D, 26E, 26F, 26G, 26H, 26I, 26J, and 26K show affinity maturation drives homotypic repeat binding. (A to H) 1210 Fab/NANP5 co-crystal structure. (A) Superposition of the four NANP-bound Fabs. (B) Surface representation of the antigen-antibody interaction. (C) Details of core epitope recognition by 1210. Black dashes indicate H-bonds. (D) Two 1210 Fabs in complex with NANP5. [(E) and (F)] Surface representation of Fab-B (E) and Fab-A (F). Residues involved in homotypic interactions are dark gray. [(G) and (H)] Details of homotypic interactions. Affinity matured residues are bold and underlined. (I) Mean±SEM KD determined by isothermal titration calorimetry (ITC). Dots represent measurements from at least three independent experiments. One-tailed Mann-Whitney test: *P<0.05, ** P<0.01. (J) Size-exclusion chromatography coupled with multi-angle light scattering (SEC/MALS) for the 1210 Fab-PfCSP complex. Line indicates mean±SD molar mass from two measurements. (K) 2D class averages for the 1210 Fab-PfCSP complex. Arrows indicate individual Fabs, and white lines indicate the binding angle observed in the crystal structure (D). Scale bar, 10 nm.
Figure 26B:
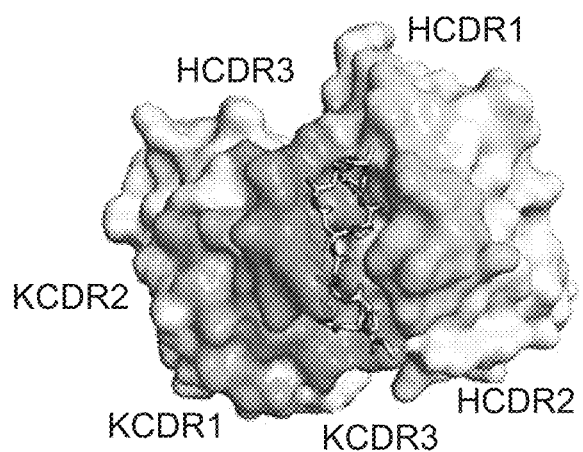
Figure 26C:
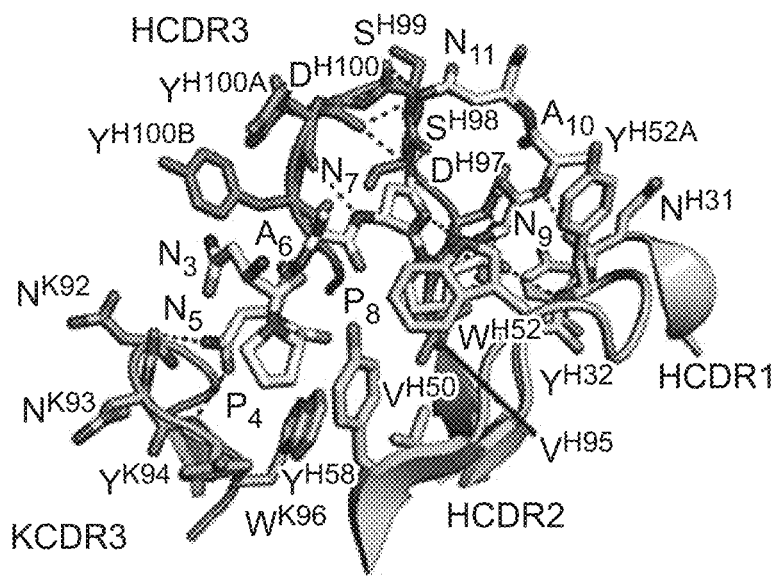
Figure 26G:
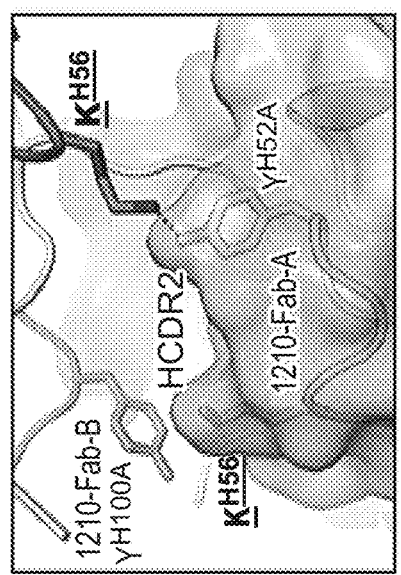
Figure 26H:
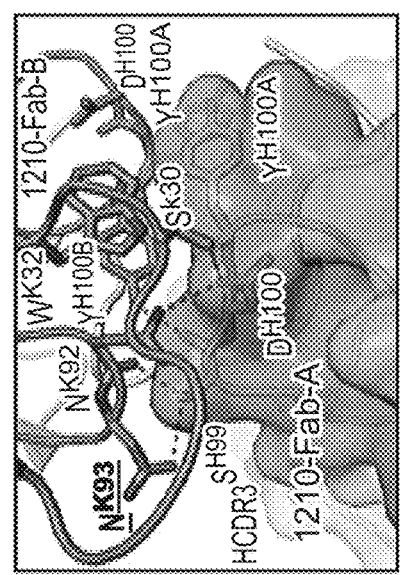
Figure 26E:
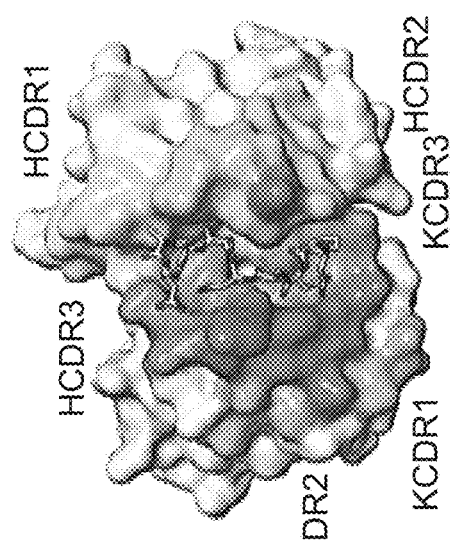
Figure 26F:
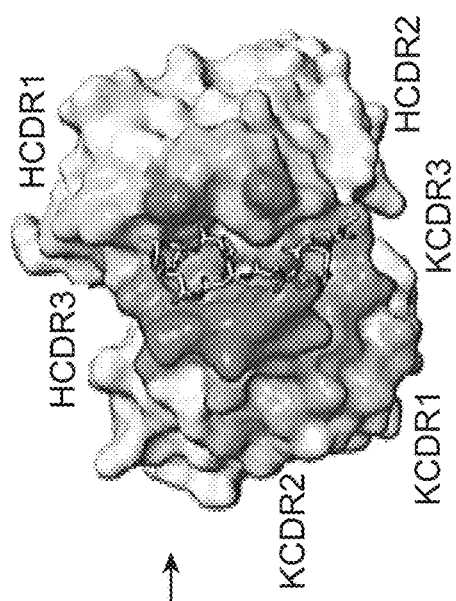

| | |
|---|---|
| 2163_H.N56_K$^{mut}$_K.S93_N$^{mut}$ Named 2163_KN | QVQLVESGGGVVQPGRSLRLSCAASGFTFS**SYG*MH*W**VRQAPGKGLEWVA*VIWYDGSKKYYADSVK*GRFTISRDNSKNTLYLQMNSLRAEDTAVYYC*ARVQTTT{GGGSCCCPFDY}W*GQGTLVTVSS (SEQ ID NO: 38) |
| 2163 variants IgK | ----------IGKV1-5*03------------- K.93 ---------IGKJ1*01 |
| 2163 | DIQMTQSPSSLSASVGDRVTITCRASQSISSWLAWYQQKPGKAPKLLIY*KAS**SLES*GVPSRFSGSGSGTEFTLTISSLQPDDFATYYCQQY*NS*YWTFGQGTKVEIK (SEQ ID NO: 39) |
| 2163_H.V50_I$^{mut}$ | DIQMTQSPSSLSASVGDRVTITCRASQSISSWLAWYQQKPGKAPKLLIY*KAS**SLES*GVPSRFSGSGSGTEFTLTISSLQPDDFATYYCQQY*NS*YWTFGQGTKVEIK (SEQ ID NO: 39) |
| 2163_H.S31_N$^{mut}$ | DIQMTQSPSSLSASVGDRVTITCRASQSISSWLAWYQQKPGKAPKLLIY*KAS**SLES*GVPSRFSGSGSGTEFTLTISSLQPDDFATYYCQQY*NS*YWTFGQGTKVEIK (SEQ ID NO: 39) |
| 2163_H.N56_K$^{mut}$ | DIQMTQSPSSLSASVGDRVTITCRASQSISSWLAWYQQKPGKAPKLLIY*KAS**SLES*GVPSRFSGSGSGTEFTLTISSLQPDDFATYYCQQY*NS*YWTFGQGTKVEIK (SEQ ID NO: 39) |
| 2163_H.N56_K$^{mut}$_K.S93_N$^{mut}$ Named 2163_KN | DIQMTQSPSSLSASVGDRVTITCRASQSISSWLAWYQQKPGKAPKLLIY*KAS**SLES*GVPSRFSGSGSGTEFTLTISSLQPDDFATYYCQQY*NN*YWTFGQGTKVEIK (SEQ ID NO: 40) | italic: CDRs | single underline: mutations at positions H.31, H.50, H.56 and K.93 | double underline: mutations at other positions | curly underline: mutations that restrict homotypic interaction by steric hindrance We next determined the co-crystal structure of the 1210 antigen-binding fragment (Fab) with NANP5 (FIG. 26, FIG. 27A, and Tables 5 to 7). The NANP core epitope contained a Type I β-turn and an elongated conformation (FIGS. 26, A and C, and FIG. 27B), similar to NANP bound to a chimeric IgH 2140/Igκ 1210 antibody and in line with previous observations (FIG. 27C and tables 5 and 8) (10-14). Main-chain atoms in KCDR3 were optimally positioned to mediate H-bonds with the repeat, likely contributing to the strong selection of 8-aa-long KCDR3s (FIGS. 26, B and C, and tables 3, 6, and 11). VH3-33 germline residues mediated the majority of antigen contacts, notably H.V50 and H.W52 (the residue uniquely encoded by IGHV3-33 alleles), as well as H. Y52A and H.Y58 in HCDR2 (table 6 and FIG. 28) (15). Affinity maturation at H.V50 and H.S31 may be explained by strengthened van der Waals interactions with the repeat (FIG. 26C).

TABLE 5

Data collection and refinement statistics.

|  | 1210-NANP$_5$ | 2140-1210-NANP$_3$ | 1450-NANP$_5$ |
|---|---|---|---|
| Wavelength (Å) | 0.97949 | 1.03327 | 0.97949 |
| Space group | C2 | P4$_3$2$_1$2 | C222$_1$ |
| Cell dimensions |  |  |  |
| a, b, c (Å) | 206.0, 150.9, 134.7 | 83.1, 83.1, 157.2 | 51.6, 135.1, 344.1 |
| α, β, γ (°) | 90, 94.8, 90 | 90, 90, 90 | 90, 90, 90 |
| Resolution (Å)$^a$ | 40-3.2 (3.3-3.2) | 40-1.85 (1.95-1.85) | 40-3.4 (3.6-3.4) |
| No. molecules in ASU | 2 | 1 | 1 |
| No. unique observations | 67,565 (5,890) | 47,923 (6,923) | 15,950 (2,452) |
| Multiplicity | 3.8 (3.8) | 12.6 (12.2) | 3.9 (4.0) |
| R$_{merge}$ (%)$^b$ | 14.7 (63.3) | 6.8 (75.5) | 31.1 (72.7) |
| R$_{pim}$ (%)$^c$ | 8.8 (37.5) | 2.0 (22.3) | 16.5 (38.6) |
| <I/σ I> | 8.9 (1.6) | 21.8 (1.7) | 4.5 (1.3) |
| CC$_{1/2}$ | 99.0 (57.0) | 99.9 (76.6) | 95.7 (49.6) |
| Completeness (%) | 99.8 (100) | 99.7 (98.5) | 92.1 (92.9) |
| Refinement Statistics |  |  |  |
| Reflections (work) | 65,564 | 45,843 | 15,107 |
| Reflections (test) | 2,001 | 2,000 | 796 |
| Non-Hrydrogen atoms | 13,610 | 3,655 | 6,524 |
| Macromolecule | 13,369 | 3,361 | 6,524 |
| Water | 0 | 269 | 0 |
| Heterostom | 241 | 25 | 0 |
| R$_{work}^d$/R$_{free}^e$ | 20.3/22.8 | 17.9/20.9 | 25.4/29.9 |
| Rms deviations from ideality |  |  |  |
| Bond lengths (Å) | 0.004 | 0.014 | 0.004 |
| Bond angle (°) | 0.95 | 1.48 | 1.06 |
| Ramachandran plot |  |  |  |
| Favoured regions (%) | 96.3 | 96.8 | 95.3 |
| Allowed regions | 3.7 | 3.2 | 4.7 |
| B-factors (Å$^2$) |  |  |  |
| Wilson B-value | 68 | 35 | 57 |
| Average B-factors | 83 | 55 | 89 |
| Average macromolecule | 83 | 55 | 89 |
| Average heteroatom | 92 | 108 | — |
| Average water molecule | — | 51 | — |

$^a$Values in parentheses refer to the highest resolution bin.
$^b$R$_{merge}$ = Σ$_{hkl}$ Σ$_i$ |I$_{hkl, i}$ − <I$_{hkl}$>|/Σ$_{hkl}$<I$_{hkl}$>
$^c$R$_{pim}$ = Σ$_{hkl}$ [1/(N − 1)]$_{1/2}$ Σ$_i$ |I$_{hkl, i}$ − <I$_{hkl}$>|/Σ$_{hkl}$ <I$_{hkl}$>
$^d$R$_{work}$ = (Σ||F$_o$| − |F$_c$||/(Σ|F$_o$|))for all data except as indicated in footnote e.
$^e$5% of data were used for the R$_{free}$ calculation

TABLE 6

Table of contacts between NANP$_5$ and 1210 Fabs.

| NANP$_5$ (BSA Å$^2$) | Interaction | 1210-A | 1210-B |
|---|---|---|---|
| Ala2 (A-9 B-30) |  |  |  |
| Ala | VDW | H-Tyr58 | H-Tyr100A |
| Ala$^N$ | HB |  | H-Tyr100A$^{OH}$ |
| Asn3 (A-43 B-10) |  |  |  |
| Asn | VDW | H-Tyr58, H-Trp52, H-Tyr100A, H-Tyr100B | H-Tyr100A |

TABLE 6-continued

Table of contacts between NANP$_5$ and 1210 Fabs.

| NANP$_5$ (BSA Å$^2$) | Interaction | 1210-A | 1210-B |
|---|---|---|---|
| Pro4 (A-123 B-0) | | | |
| Pro | VDW | K-Tyr94, K-Trp96, H-Trp52, H-Tyr58 | |
| Asn5 (A-123 B-0) | | | |
| Asn | VDW | K-Tyr91, K-Asn92, K-Asn93, K-Tyr94, K-Trp96, H-Tyr100A, H-Tyr100B, H-Gly100C | |
| Asn$^{O\delta1}$ | HB | K-Tyr94$^N$ | |
| Asn$^{N\delta2}$ | HB | K-Asn92$^O$ | |
| Asn$^O$ | HB | H-Gly100C$^N$ | |
| Ala6 (A-28 B-16) | | | |
| Ala | VDW | H-Trp52, H-Tyr100A, H-Tyr100B, H-Gly100C | H-Tyr100A |
| Asn7 (A-72 B-0) | | | |
| Asn | VDW | H-Trp52, H-Val95, H-Ser98, H-Ser99, H-Asp100, H-Tyr100A, H-Tyr100B, H-Gly100C | |
| Asn$^N$ | HB | H-Tyx100A$^O$ | |
| Asn$^{N\delta2}$ | HB | H-Ser98$^O$, H-Asp100$^O$ | |
| Asn$^O$ | HB | H-Trp52$^{N\epsilon1}$ | |
| Pro8 (A-124 B-0) | | | |
| Pro | VDW | H-Tyr32, H-Gly33, H-His35, H-Val50, H-Ile51, H-Trp52, H-Tyr52A, H-Val95, H-Gly100C | |
| Pro$^O$ | HB | H-Tyr52A$^N$ | |
| Asn9 (A-108 B-0) | | | |
| Asn | VDW | H-Asn31, H-Tyr32, H-Gly33, H-Tyr52A, H-Val95, H-Arg96, H-Asp97, H-Ser98 | |
| Asn$^{O\delta1}$ | HB | H-Gly33$^N$ | |
| Asn$^{N\delta2}$ | HB | H-Val95$^O$, H-Arg96$^O$, H-Asp97$^{O\delta1}$ | |
| Ala10 (A-73 B-12) | | | |
| Ala | VDW | H-Asn31, H-Tyr32, H-Tyr52A, H-Asp97, H-Ser98 | H-Tyr58 |
| Ala$^N$ | HB | H-Asn31$^O$ | |
| Asn11 (A-26 B-27) | | | |
| Asn | VDW | H-Ser98, H-Ser99, H-Asp100, H-Tyr100A, H-Tyr100B | H-Trp52, H-Tyr58, H-Tyr100B |
| Asn$^{N\delta2}$ | HB | H-Ser99$^O$, H-Asp100$^O$ | |
| Pro12 (A-7 B-115) | | | |
| Pro | VDW | H-Ser99 | K-Tyr94, K-Trp96, H-Trp52, H-Tyr58 |
| Asn13 (A-17 B-121) | | | |
| Asn | VDW | H-Ser99 | K-Tyr91, K-Asn92, K-Asn93, K-Tyr94, K-Trp96, H-Tyr100B, H-Gly100C |
| Asn$^{O\delta1}$ | HB | | K-Tyr94$^N$ |
| Asn$^{N\delta2}$ | HB | | K-Tyr94$^O$ |
| Asn$^O$ | HB | | H-Gly100C$^N$ |
| Ala14 (A-0 B-27) | | | |
| Ala | VDW | | H-Trp52, H-Tyr100A, H-Tyr100B, H-Gly100C |

TABLE 6-continued

Table of contacts between $NANP_5$ and 1210 Fabs.

| $NANP_5$ (BSA Å$^2$) | Interaction | 1210-A | 1210-B |
|---|---|---|---|
| Asn15 (A-0 B-71) | | | |
| Asn | VDW | | H-Trp52, H-Val95, H-Arg96, H-Ser98, H-Asp100, H-Tyr100A, H-Tyr100B, H-Gly100C |
| $Asn^N$ | HB | | H-Tyr100A$^O$ |
| $Asn^{Nδ2}$ | HB | | H-Ser98$^O$, H-Asp100$^O$ |
| $Asn^O$ | HB | | H-Trp52$^{Nε1}$ |
| Pro16 (A-0 B-125) | | | |
| Pro | VDW | | H-Asn31, H-Tyr32, H-Gly33, H-Val50, H-Ile51, H-Trp52, H-Tyr52A, H-Val95, H-Gly100C |
| $Pro^O$ | HB | | H-Tyr52A$^N$ |
| Asn17 (A-0 B-107) | | | |
| Asn | VDW | | H-Asn31, H-Tyr32, H-Gly33, H-Tyr52A, H-Val95, H-Arg96, H-Asp97, H-Ser98 |
| $Asn^{Oδ1}$ | HB | | H-Gly33$^N$ |
| | HB | | H-Val95$^O$, H-Arg96$^O$, H-Asp97$^{Oδ1}$ |
| Ala18 (A-0 B-68) | | | |
| Ala | VDW | | H-Ser30, H-Asn31, H-Tyr32, H-Tyr52A |
| $Ala^N$ | HB | | H-Asn31$^O$ |
| Asn19 (A-0 B-51) | | | |
| Asn | VDW | | H-Ser98, H-Ser99, H-Asp100, H-Tyr100A |
| $Asn^{Nδ2}$ | HB | | H-Ser99$^O$ |

HB: hydrogen bond (3.89 Å cut-off)
VDW: van der Waals (5.0 Å cut-off)

TABLE 7

Table of contacts between 1210 Fab-A and 1210 Fab-B.

| 1210-Fab (A) (BSA Å$^2$) | Interaction | 1210-Fab (B) |
|---|---|---|
| H-Tyr52A (32) | | |
| H-Tyr | VDW | H-Lys56 |
| H-Tyr$^{OH}$ | HB | H-Lys56$^{Nξ}$ |
| H-Lys56 (30) | | |
| H-Lys | VDW | H-Tyr100A |
| H-Ser99 (54) | | |
| H-Ser | VDW | K-Asn92, K-Asn93, H-Tyr100B |
| H-Ser$^{Oγ}$ | HB | K-Asn92$^O$, K-Asn93$^{Oδ1}$ |
| H-Ser$^O$ | HB | H-Tyr100B$^{OH}$ |
| H-Asp 100 (45) | | |
| H-Asp | VDW | K-Ser30, K-Trp32, K-Asn92, H-Tyr100B |
| H-Asp$^{Oδ2}$ | HB | K-Ser30$^{Oγ}$, K-Asn92$^{Nδ2}$ |
| H-Tyr100A (104) | | |
| H-Tyr | VDW | K-Trp32, H-100Asp, H-Tyr100A, H-Tyr100B |

HB: hydrogen bond (3.89 Å cut-off)
VDW: van der Waals (5.0 Å cut-off)

TABLE 8

Table of contacts between $NANP_3$ and the chimeric H.2140/K.1210 Fab.

| $NANP_3$ (BSA Å$^2$) | Interaction | H.2140/K.1210 Fab |
|---|---|---|
| Ala2 (37) | | |
| Ala | VDW | H-Lys56, H-Tyr58 |
| Asn3 (12) | | |
| Asn | VDW | K-Asn92, K-Asn93, H-Trp52, H-Tyr58 |
| $Asn^{Oδ1}$ | WMHB | K-Asn92$^O$, K-Asn93$^O$ |

TABLE 8-continued

Table of contacts between NANP$_3$ and the chimeric H.2140/K.1210 Fab.

| NANP$_3$ (BSA Å$^2$) | Interaction | H.2140/K.1210 Fab |
|---|---|---|
| Asn$^{N\delta2}$ | WMHB | H-Ser100C$^{O\gamma}$ |
| Asn$^O$ | WMHB | H-Tyr58$^{OH}$ |
| Pro4 (117) | | |
| Pro | VDW | K-Asn93, K-Tyr94, K-Trp96, H-Ile50, H-Trp52, H-Tyr58 |
| Asn5 (132) | | |
| Asn | VDW | K-Tyr91, K-Asn92, K-Asn93, K-Tyr94, K-Trp96, H-Asp100B, H-Ser100C, H-Ser100D |
| Asn$^{O\delta1}$ | HB | K-Tyr94$^N$ |
| Asn$^{N\delta2}$ | HB | K-Tyr91$^O$, L-Tyr94$^O$, H-Ser100D$^O$ |
| Asn$^O$ | HB | H-Ser100D$^N$ |
| Ala6 (14) | | |
| Ala | VDW | H-Trp52, H-Ser100D |
| Asn7 (35) | | |
| Asn | VDW | H-Trp52, H-Glu97, H-Asp100B, H-Ser100D |
| Asn$^{N\delta2}$ | WMHB | H-Glu97$^O$, H-Asp100B$^O$ |
| Asn$^O$ | HB | H-Trp52$^{N\epsilon1}$ |
| Pro8 (121) | | |
| Pro | VDW | H-Tyr32, H-Gly33, H-Ile50, H-Ile51, H-Trp52, H-Tyr52A, H-Val95, H-Ser100D |
| Pro$^O$ | HB | H-Gly33$^N$, H-Tyr52A$^N$ |
| Asn9 (85) | | |
| Asn | VDW | H-Ser31, H-Tyr32, H-Gly33, H-Tyr52A, H-Val95, H-Gly96, H-Glu97, H-Ser100D |
| Asn$^{O\delta1}$ | HB | H-Gly33$^N$ |
| Asn$^{N\delta2}$ | WMHB | H-Glu97$^O$, H-Ser100D$^{O\gamma}$ |
| Ala10 (62) | | |
| Ala | VDW | H-Ser30, H-Ser31, H-Tyr32, H-Tyr52A |
| Ala$^N$ | HB | H-Ser31$^O$ |

HB: hydrogen bond (3.89 Å cut-off)
WMHB: water-mediated hydrogen bond (3.89 Å cut-off)
VDW: van der Waals (5.0 Å cut-off)

TABLE 9

Table of contacts between NANP$_5$ and 1450 Fabs

| NANP$_5$ (BSA Å$^2$) | Interaction | 1450-A | 1450-B |
|---|---|---|---|
| Asn1 (A-64 B-0) | | | |
| Asn | VDW | K-Lys50, H-Phe98 | |
| Ala2 (A-65 B-0) | | | |
| Ala | VDW | K-Trp32, H-Phe98, H-Cys99, H-Ser100 | |
| Asn3 (A-132 B-0) | | | |
| Asn | VDW | K-Tyr91, H-Glu95, H-Gly96, H-Gly97, H-Phe98, H-Cys99, H-Ser100, H-Cys100D, H-Tyr100E, H-Tyr100F, H-Tyr100G | |
| Asn$^N$ | HB | H-Phe98$^O$ | |
| Asn$^{N\delta2}$ | HB | H-Glu95$^{N\epsilon2}$, H-Gly96$^O$, H-Phe98$^O$ | |
| Pro4 (A-122 B-D) | | | |
| Pro | VDW | K-Trp32, H-Tyr91, H-Gly92, H-Cys100D, H-Tyr100E | |
| Pro$^O$ | HB | H-Tyr100E$^N$ | |

TABLE 9-continued

Table of contacts between NANP$_5$ and 1450 Fabs

| NANP$_5$ (BSA Å$^2$) | Interaction | 1450-A | 1450-B |
|---|---|---|---|
| Asn5 (A-45 B-18) | | | |
| Asn | VDW | H-Ser100A, H-Cys100D, H-Thr100C, H-Tys100E | H-Ser100 |
| Asn$^{O\delta1}$ | HB | H-Ser100A$^{O\gamma}$ | |
| Asn$^{N\delta2}$ | HB | | H-Ser100$^{O\gamma}$ |
| Ala6 (A-93 B-0) | | | |
| Ala | VDW | H-Tyr58, H-Thr100C, H-Cys100D, H-Tyr100E | |
| Ala$^N$ | HB | H-Thr100C$^O$ | |
| Asn7 (A-18 B-17) | | | |
| Asn | VDW | H-Thr100C | H-Phe98, H-Ser100 |
| Pro8 (A-3 B-30) | | | |
| Pro | VDW | | K-Lys50 |
| Pro$^O$ | HB | | K-Lys50$^{N\epsilon1}$ |
| Asn9 (A-0 B-28) | | | |
| Asn | VDW | | K-Lys50, H-Phe98 |
| Ala10 (A-0 B-46) | | | |
| Ala | VDW | | H-Trp32, H-Phe98, H-Ser100 |
| Asn11 (A-0 B-126) | | | |
| Asn | VDW | | H-Trp32, K-Tyr91, H-Glu95, H-Gly96, H-Gly97, H-Phe98, H-Cys99, H-Cys100D, H-Tyr100E, H-Tyr100F, H-Tyr100G |
| Asn$^N$ | HB | | H-Phe98$^O$ |
| Asn$^{N\delta2}$ | HB | | H-Glu95$^{N\epsilon2}$, H-Gly96$^O$, H-Phe98$^O$ |
| Pro12 (A-0 B-127) | | | |
| Pro | VDW | | K-Trp32, K-Tyr91, H-Cys100D, H-Tyr100E |
| Pro$^O$ | HB | | H-Tyr100E$^N$ |
| Asn13 (A-31 B-50) | | | |
| Asn | VDW | H-Ser100, H-Ser100A | H-Cys99, H-Ser100, H-Ser100A, H-Thr100C, H-Cys100D, H-Tyr100E |
| Asn$^{N\delta2}$ | HB | H-Ser100$^{O\gamma}$ | |
| Asn$^{O\delta1}$ | HB | | H-Ser100A$^N$ H-Ser100A$^{O\gamma}$ |
| Ala14 (A-0 B-84) | | | |
| Ala | VDW | | H-Tyr58, H-Thr100C, H-Cys100D, H-Tyr100E |
| Ala$^N$ | HB | | H-Thr100C$^O$ |
| Asn15 (A-0 B-20) | | | |
| Asn | VDW | | H-Tyr58, H-Tyr100E |
| Asn$^O$ | HB | | H-Tyr58$^{OH}$ |
| Pro16 (A-0 B-31) | | | |
| Pro | VDW | | H-Asp56, H-Tyr58, H-Thr100C |
| Asn 17 (A-0 B-79) | | | |
| Asn | VDW | | H-Gly55, H-Asp56, H-Thr57, H-Tyr58 |
| Asn$^N$ | HB | | H-Asp56$^{O\delta2}$ |
| Asn$^{O\delta1}$ | HB | | H-Thr57$^N$ |
| Asn$^{N\delta2}$ | HB | | H-Thr57$^{O\gamma1}$ |

HB: hydrogen bond (3.89 Å cut-off)
VDW: van der Waals (5.0 Å cut-off)

TABLE 10

Table of contacts between 1450 Fab-A and 1450 Fab-B.

| 1450-Fab (A) (BSA Å²) | Interaction | 1450-Fab (B) |
|---|---|---|
| K-Asn30 (33) | | |
| Asn | VDW | K-Asn30 |
| Asn^Nδ2 | HB | K-Asn30^Oδ1 |
| H-Ser100 (25) | | |
| Ser | VDW | H-Ser100, H-Ser100A |
| H-Ser100A (40) | | |
| Ser | VDW | H-Ser100, H-Ser100A |
| H-Ala100B (7) | | |
| Ala | VDW | H-Ser100 |

HB: hydrogen bond (3.89 Å cut-off)
VDW: van der Waals (5.0 Å cut-off)

TABLE 11

BSA and contact summary for crystal structures.

| | | H-bonds | | | BSA (Å²) | | |
|---|---|---|---|---|---|---|---|
| Source Molecule | Target Molecule | H-Chain | K-Chain | Total | H-Chain | K-Chain | Total |
| 1210 (A) | NANP5 | 13 | 2 | 15 | 533 | 140 | 673 |
| 1210 (B) | NANP5 | 13 | 2 | 15 | 585 | 122 | 707 |
| 1210 (A) | 1210 (B) | 6 | 0 | 6 | 259 | 0 | 259 |
| H.2140/K.1210 | NANP3 | 7 | 3 | 10 | 439 | 130 | 569 |
| 1450 (A) | NANP5 | 8 | 0 | 8 | 359 | 149 | 518 |
| 1450 (B) | NANP5 | 13 | 1 | 14 | 460 | 141 | 601 |
| 1450 (A) | 1450 (B) | 0 | 1 | 1 | 75 | 33 | 108 |

Figure 26D:
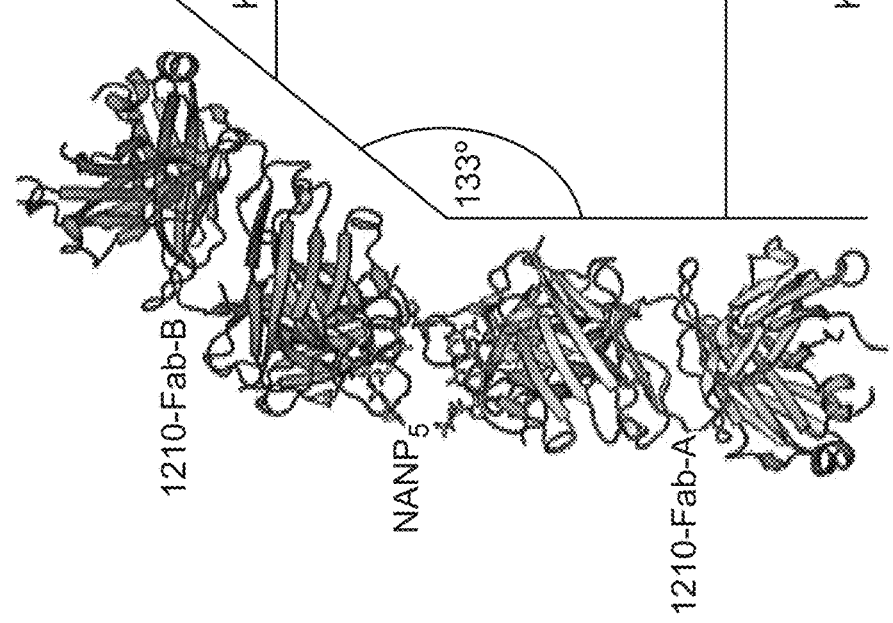

Notably, our crystal structure also revealed that two 1210 Fabs (designated 1210 Fab-A and Fab-B) bound to one NANP5 peptide in a head-to-head configuration at a 133° angle (FIG. 26D and FIG. 29). This unique binding mode led to six homotypic antibody-antibody H-bonds providing 263 A2 of buried surface area (BSA) between the two Fabs and an additional ~120 A2 of BSA between the Fabs and the repeat (FIGS. 26, E and F, and tables 6, 7, and 11). Two highly selected mutations, H.N56_K and K.S93_N (FIGS. 25, E and F), formed H-bonds with H.Y52A and H.S99 in the opposing Fab, thereby stabilizing the head-to-head configuration (FIGS. 26, G and H). The κ-aa long KCDR3 optimally contacted the HCDR3 of the opposite 1210 molecule, providing another explanation for the length restriction in KCDR3.

Figure 26I:
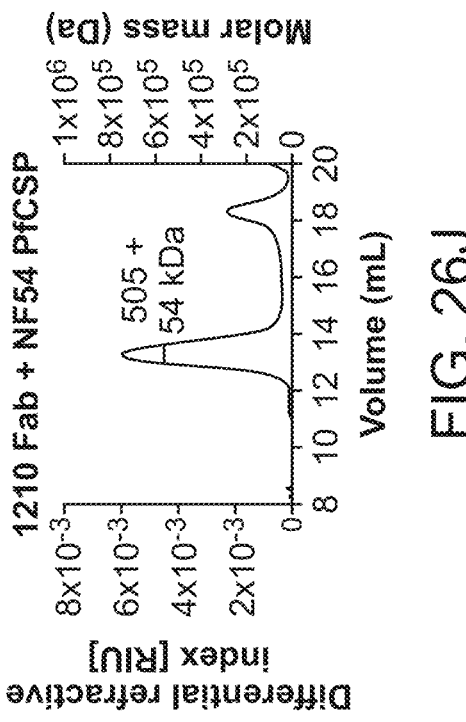
Figure 26J:
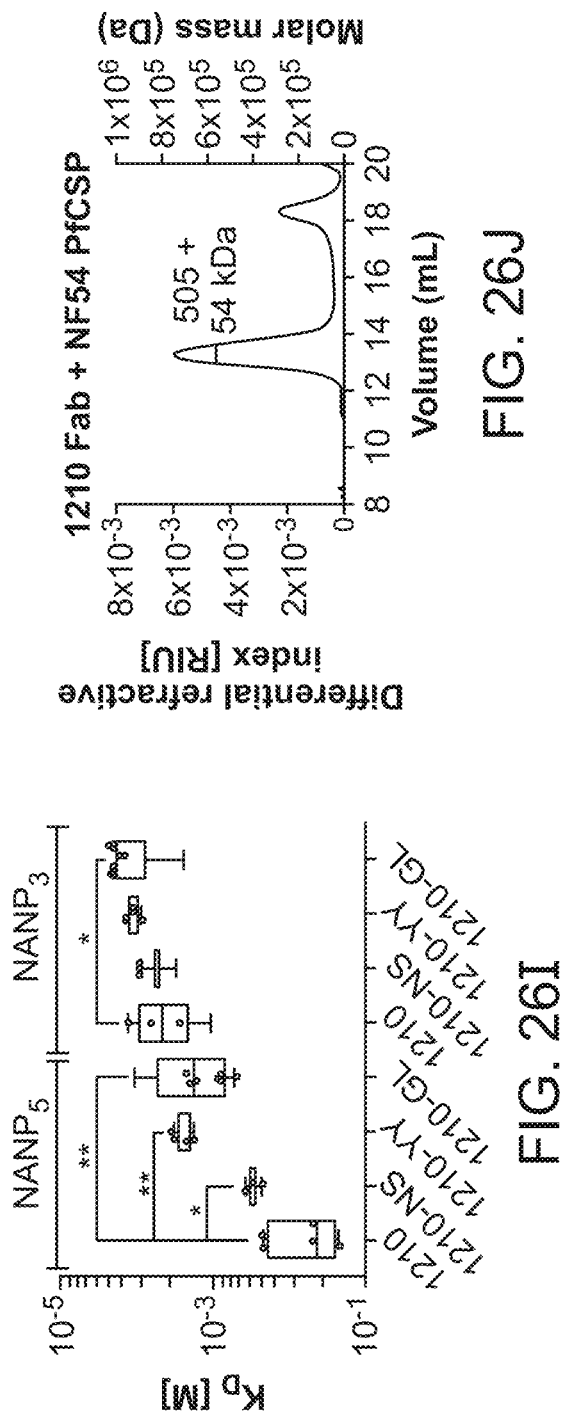
Figure 26K:
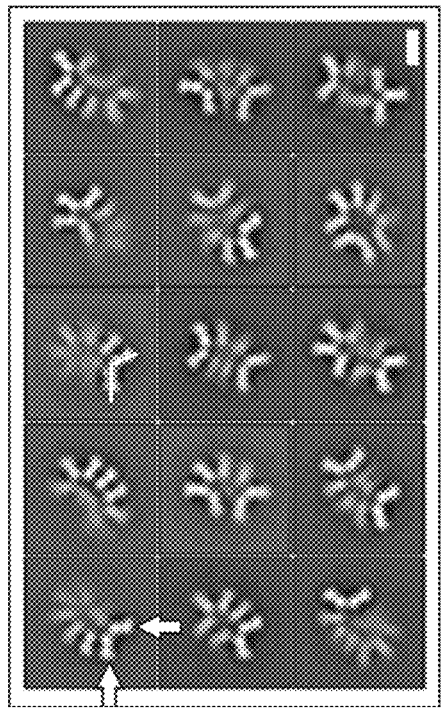
Figure 27B:
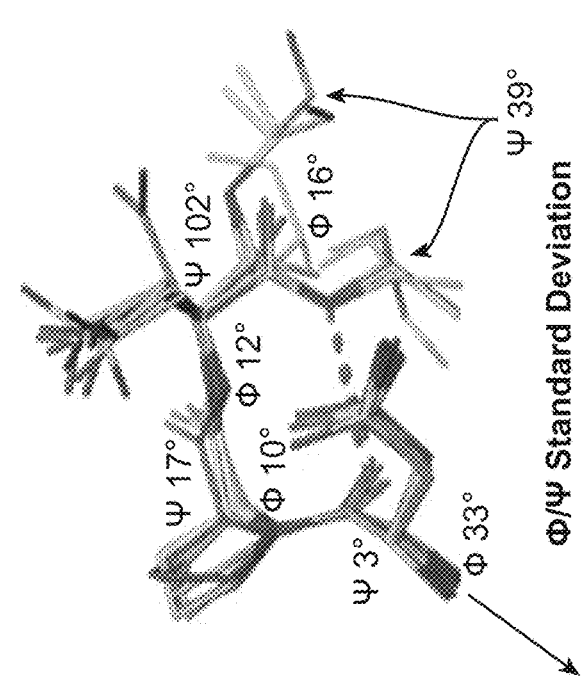
FIG. 27 shows NANP5 repeat binding by antibody 1210. A, The four 1210 Fabs bound to 2 NANP5 peptides in the asymmetric unit of the 1210-NANP5 crystal structure. B, Superposition of the NPNA cadence of 580 (10), 663 (10), 1210, and the unliganded peptide (12) structures. The standard deviation in the Phi and Psi angles is shown. C, Superposition of 1210-NANP5 with the H.2140/L. 1210 chimeric Fab in complex with a NANP3 peptide. The 1210 bound NANP5 peptide is colored yellow, and the chimeric Fab and NANP3-bound peptide are colored gray.
Figure 27C:
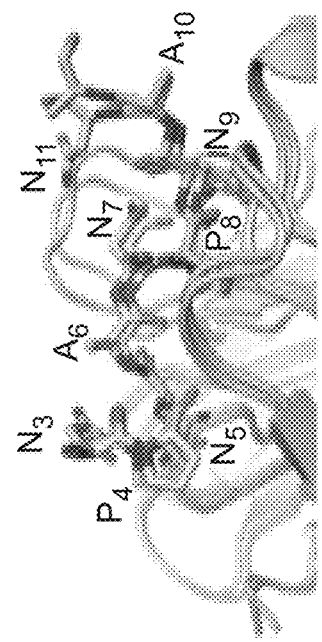
Figure 27A:
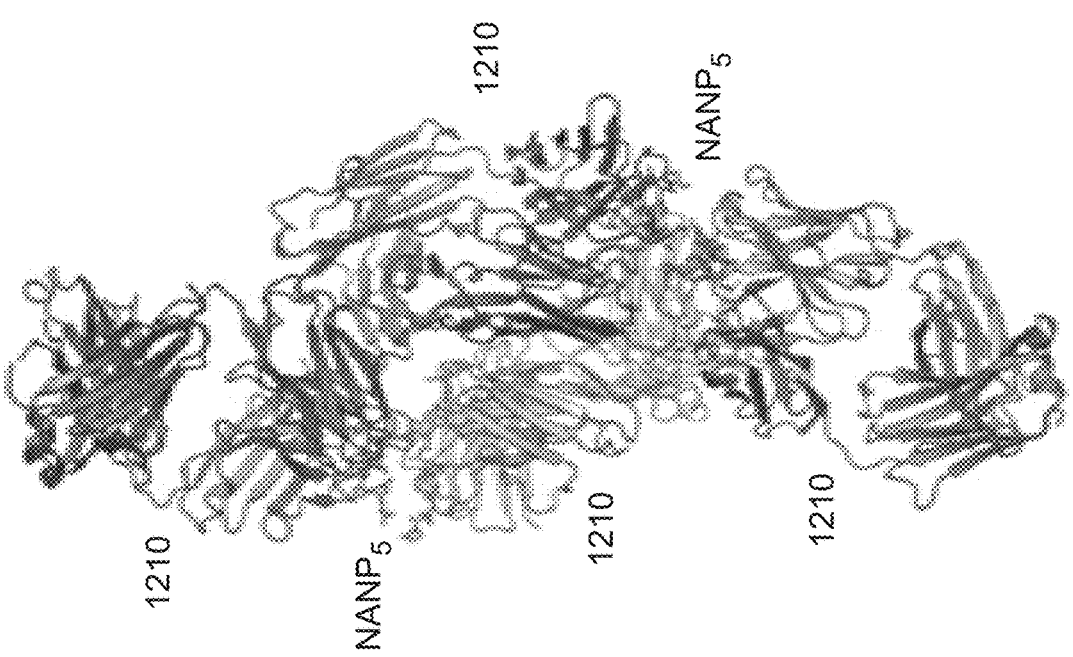

To investigate homotypic interactions, we next measured the Fab affinity to NANP5 and NANP3 for 1210, 1210_NS (which lacks the selected mutations involved in homotypic binding), a 1210 H.D100_Ymut/K.N92_Ymutmutant (1210_YY, designed to disrupt head-to-head binding through steric clashes), and 1210 germline (1210_GL) (FIG. 26I and FIG. 30). Compared to 1210, 1210_YY and 1210_NS showed significantly weaker affinity to NANP5, but not to NANP3, whereas 1210_GL was significantly worse at binding both peptides (FIG. 26I and FIG. 30) (16). These data suggest that only 1210 efficiently recognized the repeat in a high-affinity homotypic head-to-head binding configuration. An analysis of full-length PfCSP with 38 NANP repeats confirmed this hypothesis. Approximately twelve 1210 Fabs bound PfCSP and recognized the NANP repeat in a head-to-head binding configuration similar to the 1210 Fab-NANP5 crystal structure (FIGS. 26, J and K, and FIG. 29D) (11, 17). Furthermore, 1210_YY, with its restricted ability to engage in homotypic antibody interactions, showed a lower binding avidity to full-length PfCSP than 1210 (FIG. 31). Thus, affinity maturation selects for mutations that improve homotypic antibody interactions, thereby indirectly increasing PfCSP NANP binding.

Figure 32A:
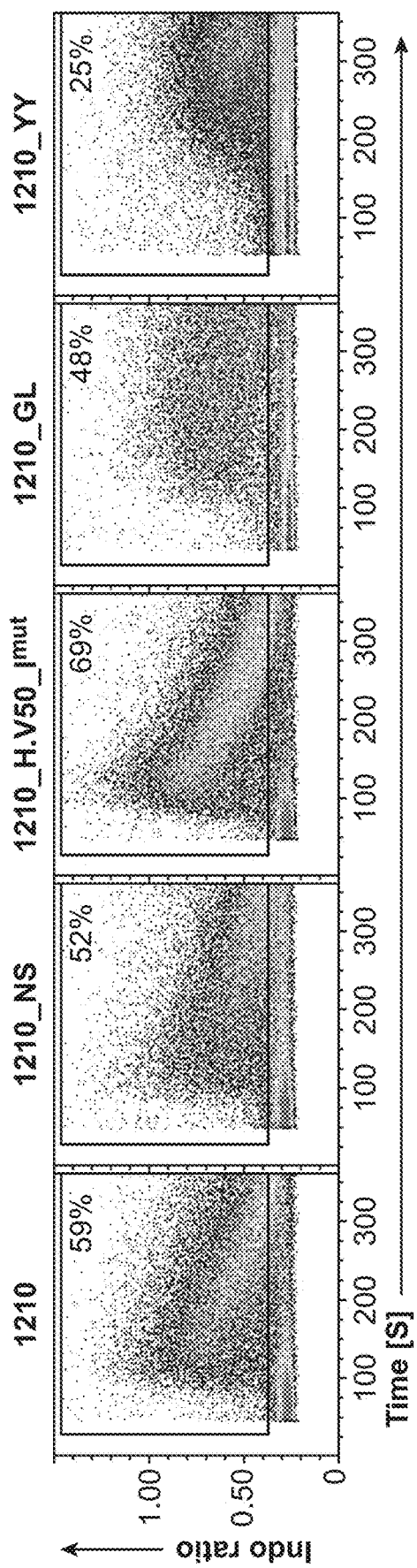
Figures 32B, 32C, 32D:
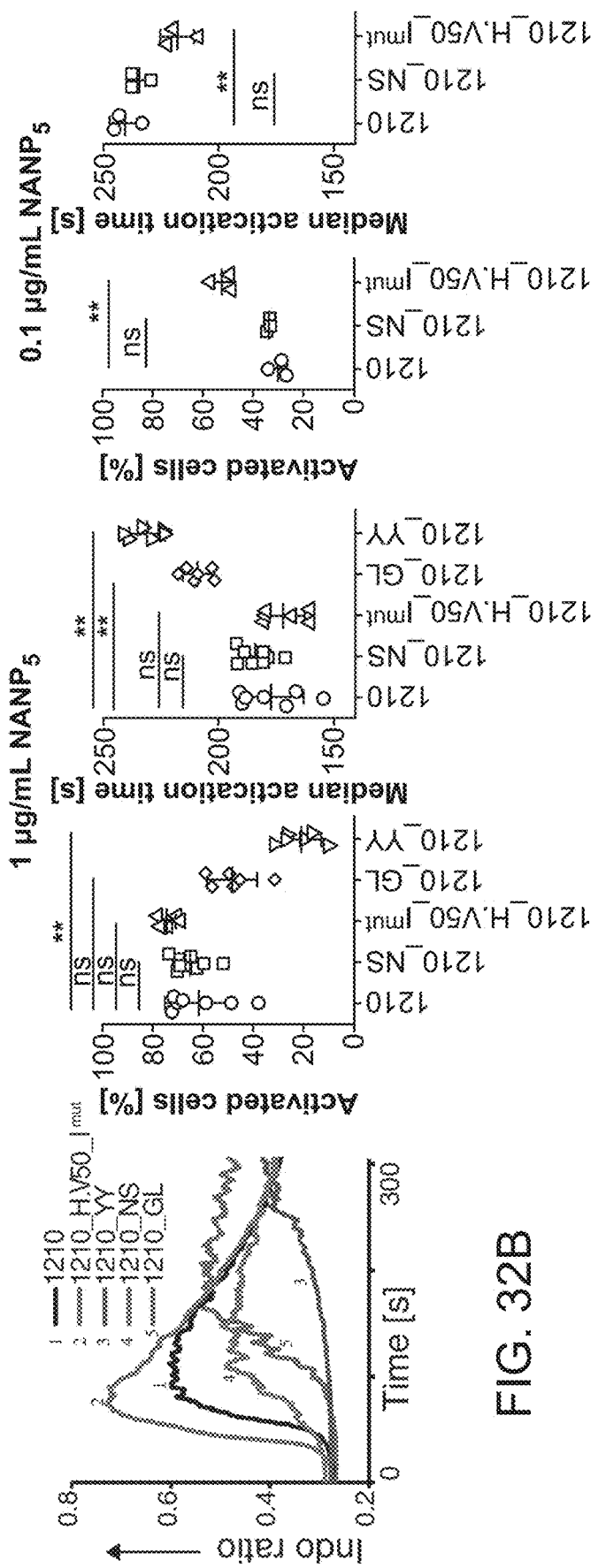
Figures 32E, 32F:
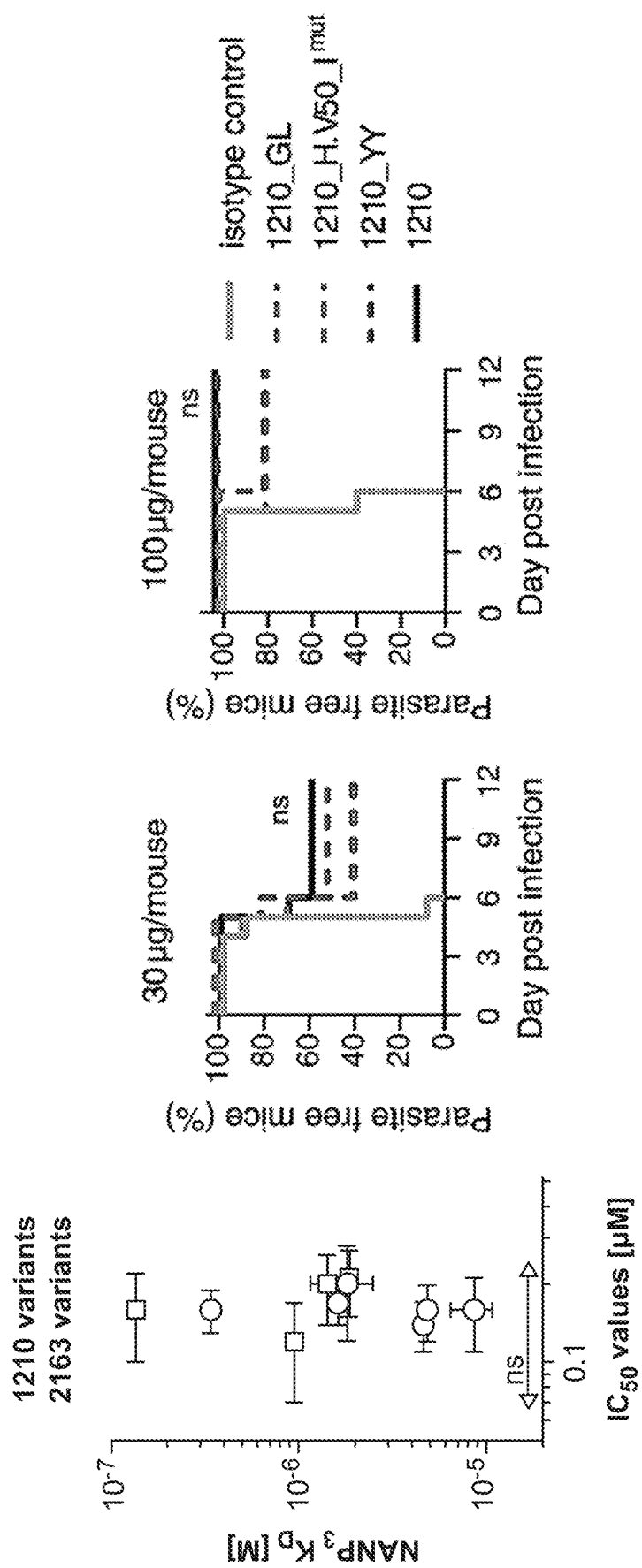

To better understand the selection of SHM at the cellular level, we measured the degree of B cell activation in response to NANP5 of transgenic B cell lines expressing 1210 or variant B cell receptors (BCRs) (FIG. 32, A to D). BCR signaling was delayed in cells expressing 1210_GL compared to 1210. This effect was even more pronounced in 1210_YY mutant cells. As expected, 1210_V50lmut with high repeat affinity mediated stronger signals than 1210, especially with low antigen concentrations, whereas 1210_NS showed no significant differences (FIG. 32D). Thus, B cell activation is promoted by both direct NANP binding and homotypic antibody interactions. Despite a two-log difference in NANP3 affinities (FIGS. 25, G and H) and the varied potential of these antibodies to engage in homotypic interactions, all showed similar capacities to inhibit Pf sporozoites in vitro (FIG. 32E and FIG. 33). Likewise, all antibodies conferred similar levels of dose-dependent protection from the development of blood-stage parasites after passive immunization in mice, presumably due to strong avidity effects (FIG. 32F). These data provide a mechanistic explanation for the strong in vivo selection of anti-homotypic antibody mutants by affinity maturation, independently of their protective efficacy as soluble antibodies.

Figure 34A:
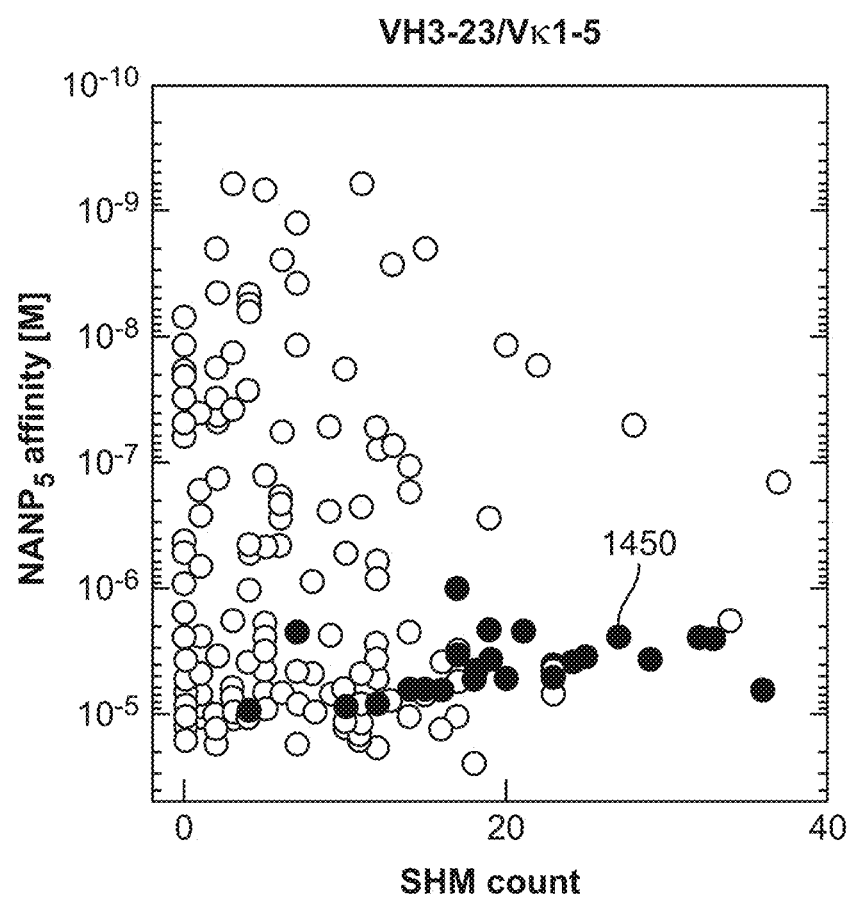
Figure 34B:
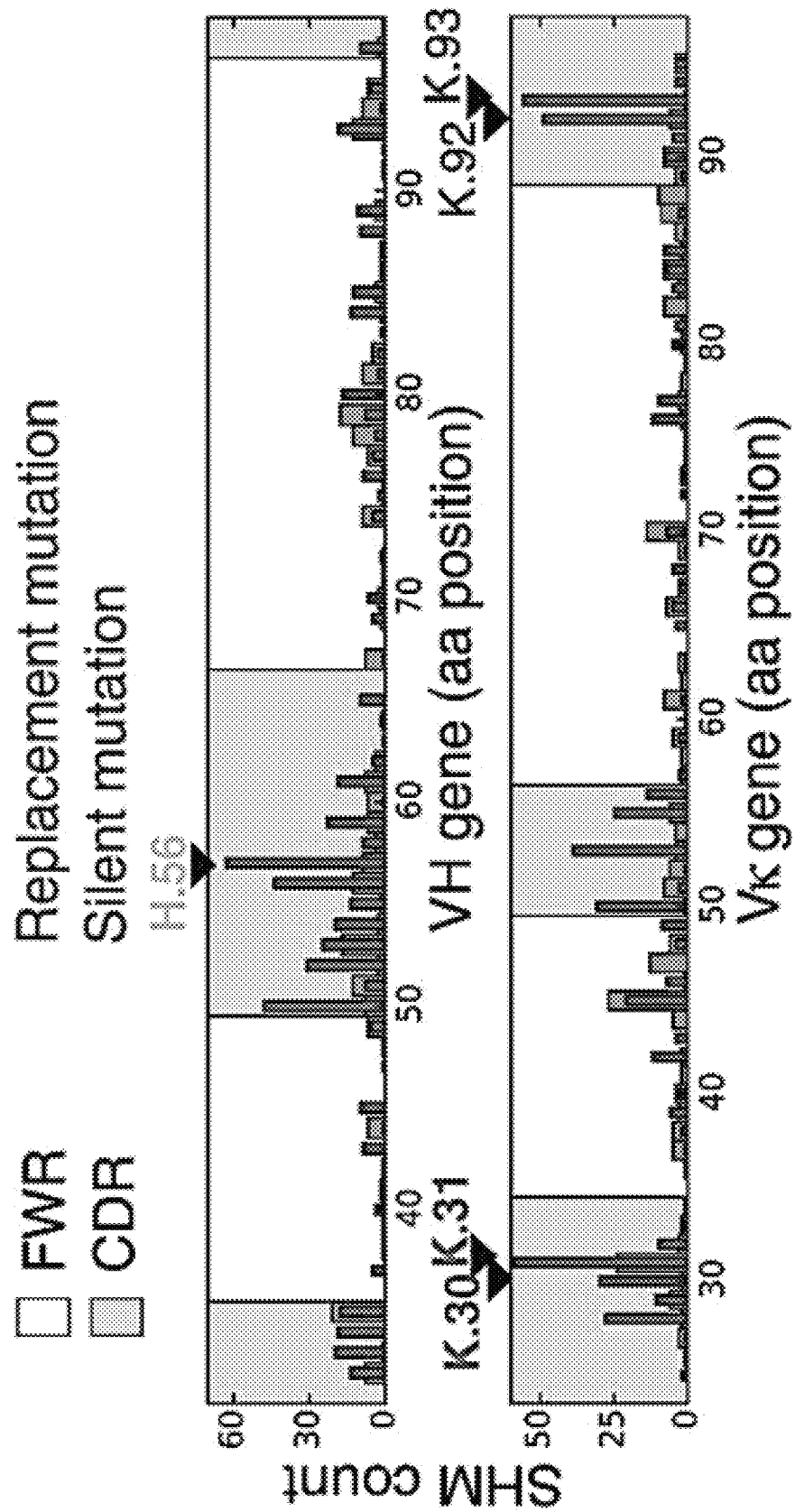
Figure 34C:
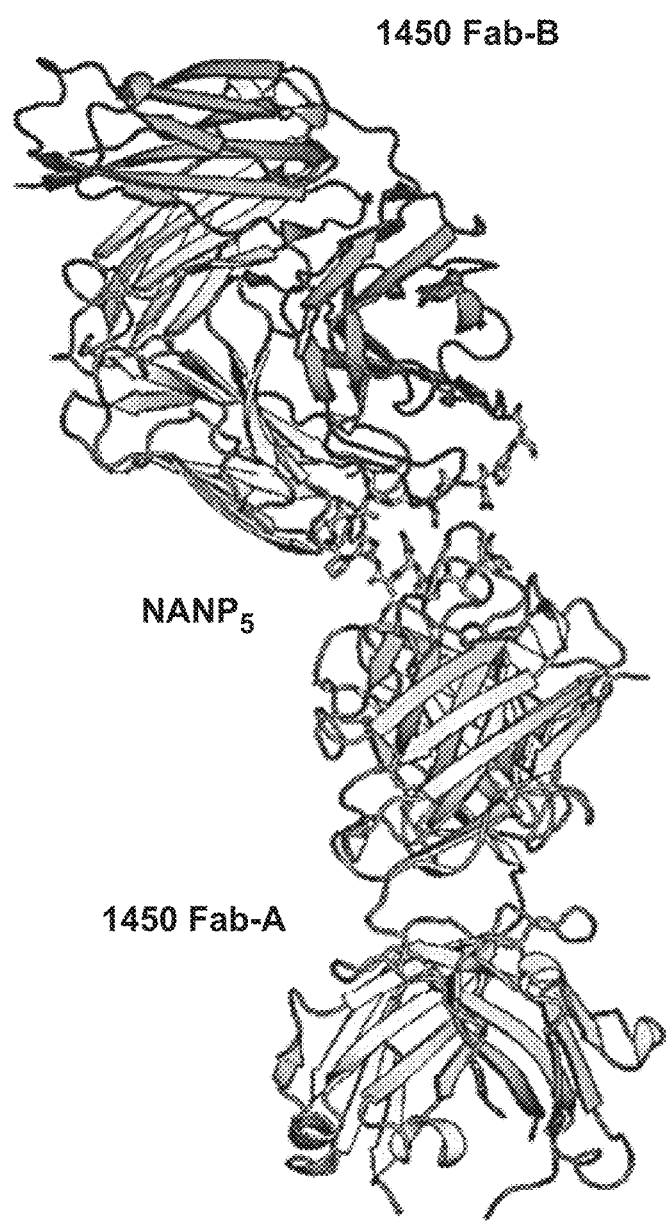

VH3 antibodies dominate the anti-PfCSP memory response (9, 11, 14). In addition to VH3-33/Vκ1-5/KCDR3: 8, we observed a cluster of highly mutated, affinity-matured VH3-23/Vκ1-5 NANP-reactive memory B cell antibodies in our selection (FIGS. 34, A and B) (9). Although the NANP5 binding mode of a representative VH3-23/Vκ1-5 antibody, 1450, was different from 1210, it also recognized NANP5 in a head-to-head configuration, with HCDR3s in direct juxtaposition and the affinity-matured K.N30 residues forming an H-bond between Fab-A and Fab-B (FIG. 34, C to E; FIGS. 35, A and B; and tables 5, 9, and 10). Sequence analysis of the VH3-23/Vk1-5 antibody cluster confirmed enrichment in aa exchanges that participate directly in antibody-antigen interactions, antibody-antibody contacts, or favor a 1450 paratope conformation optimal for NANP epitope recognition (FIG. 34B).

After PfSPZ-CVac immunization of malaria-naïve individuals, ~15% of PfCSP-reactive memory B cells showed VH3-33/Vκ1-5/KCDR3: 8 or VH3-23/Vκ1-5 sequence characteristics (FIG. 34F) (18). Furthermore these cells were strongly enriched in the expanded anti-PfCSP memory B cell pool compared to the non-expanded population (FIG. 34G). Thus, anti-homotypic affinity maturation is observed after repeated Pf sporozoite exposure (9) in both low-mutated high-affinity VH3-33 antibodies, as well as in lower-affinity antibodies utilizing other gene combinations. This phenomenon also likely takes place in B cell responses elicited by RTS,S malaria vaccination (FIG. 36) (11).

Thus, anti-homotypic affinity maturation, in addition to traditional antibody-antigen affinity maturation, promotes the strong clonal expansion and competitive selection of PfCSP-reactive B cells in humans. Even in the absence of affinity maturation, VH3-33/Vκ1-5/KCDR3: 8 antibodies are moderate-to-strong NANP binders and potent Pf inhibitors. This critically depends on H.W52 in HCDR2. Because IGHV3-33 is located in a region of structural polymorphism of the IGH locus, haplotype frequencies, especially in Pf-endemic areas, may determine the efficient induction of protective humoral anti-PfCSP repeat responses upon vaccination (19). Indeed, one donor in our study was IGHV3-33-negative (FIG. 37). We propose that anti-homotypic affinity maturation may be a generalizable property of B cell responses if a repetitive antigen (malarial or other) brings two antibodies into close proximity to optimize binding and promote clustering of surface immunoglobulin molecules through homotypic interactions (20, 21).

References

1. F. Zavala, A. H. Cochrane, E. H. Nardin, R. S. Nussenzweig, V. Nussenzweig, Circumsporozoite proteins of malaria parasites contain a single immunodominant region with two or more identical epitopes. J. Exp. Med. 157, 1947-1957 (1983).
2. J. B. Dame, J. L. Williams, T. F. McCutchan, J. L. Weber, R. A. Wirtz, W. T. Hockmeyer, W. L. Maloy, J. D. Haynes, I. Schneider, D. Roberts, G. S. Sanders, E. P. Reddy, C. L. Diggs, L. H. Miller, Structure of the gene encoding the immunodominant surface antigen on the sporozoite of the human malaria parasite *Plasmodium falciparum*. Science 225, 593-599 (1984).
3. V. Enea, J. Ellis, F. Zavala, D. E. Arnot, A. Asavanich, A. Masuda, I. Quakyi, R. S. Nussenzweig, DNA cloning of *Plasmodium falciparum* circumsporozoite gene: Amino acid sequence of repetitive epitope. Science 225, 628-630 (1984).
4. P. Potocnjak, N. Yoshida, R. S. Nussenzweig, V. Nussenzweig, Monovalent fragments (Fab) of monoclonal antibodies to a sporozoite surface antigen (Pb44) protect mice against malarial infection. J. Exp. Med. 151, 1504-1513 (1980).
5. N. Yoshida, R. S. Nussenzweig, P. Potocnjak, V. Nussenzweig, M. Aikawa, Hybridoma produces protective antibodies directed against the sporozoite stage of malaria parasite. Science 207, 71-73 (1980).
6. L. Foquet, C. C. Hermsen, G.-J. van Gemert, E. Van Braeckel, K. E. Weening, R. Sauerwein, P. Meuleman, G. Leroux-Roels, Vaccine-induced monoclonal antibodies targeting circumsporozoite protein prevent *Plasmodium falciparum* infection. J. Clin. Invest. 124, 140-144 (2014).
7. E. M. Riley, V. A. Stewart, Immune mechanisms in malaria: New insights in vaccine development. Nat. Med. 19, 168-178 (2013).
8. B. Mordmüller, G. Surat, H. Lagler, S. Chakravarty, A. S. Ishizuka, A. Lalremruata, M. Gmeiner, J. J. Campo, M. Esen, A. J. Ruben, J. Held, C. L. Calle, J. B. Mengue, T. Gebru, J. Ibáñez, M. Sulyok, E. R. James, P. F. Billingsley, K. C. Natasha, A. Manoj, T. Murshedkar, A. Gunasekera, A. G. Eappen, T. Li, R. E. Stafford, M. Li, P. L. Felgner, R. A. Seder, T. L. Richie, B. K. L. Sim, S. L. Hoffman, P. G. Kremsner, Sterile protection against human malaria by chemoattenuated PfSPZ vaccine. Nature 542, 445-449 (2017).
9. R. Murugan, L. Buchauer, G. Triller, C. Kreschel, G. Costa. G. Pidelaserra Marti, K. Imkeller, C. E. Busse, S. Chakravarty, B. K. L. Sim, S. L. Hoffman, E. A. Levashina, P. G. Kremsner, B. Mordmüller, T. Höfer, H. Wardemann, Clonal selection drives protective memory B cell responses in controlled human malaria infection. Sci. Immunol. 3, eaap8029 (2018).
10. G. Triller, S. W. Scally, G. Costa, M. Pissarev, C. Kreschel, A. Bosch, E. Marois, B. K. Sack, R. Murugan, A. M. Salman, C. J. Janse, S. M. Khan, S. H. I. Kappe, A. A. Adegnika, B. Mordmüller, E. A. Levashina, J.-P. Julien, H. Wardemann, Natural parasite exposure induces protective human anti-malarial antibodies. Immunity 47, 1197-1209.e10 (2017).
11. D. Oyen, J. L. Torres, U. Wille-Reece, C. F. Ockenhouse, D. Emerling, J. Glanville, W. Volkmuth, Y. Flores-Garcia, F. Zavala, A. B. Ward, C. R. King, I. A. Wilson, Structural basis for antibody recognition of the NANP repeats in *Plasmodium falciparum* circumsporozoite protein. Proc. Natl. Acad. Sci. U.S.A. 114, E10438-E10445 (2017).
12. A. Ghasparian, K. Moehle, A. Linden, J. A. Robinson, Crystal structure of an NPNArepeat motif from the circumsporozoite protein of the malaria parasite *Plasmodium falciparum*. Chem. Commun. 14, 174-176 (2006).
13. N. K. Kisalu, A. H. Idris, C. Weidle, Y. Flores-Garcia, B. J. Flynn, B. K. Sack, S. Murphy, A. Schön, E. Freire, J. R. Francica, A. B. Miller, J. Gregory, S. March, H.-X. Liao, B. F. Haynes, K. Wiehe, A. M. Trama, K. O. Saunders, M. A. Gladden, A. Monroe, M. Bonsignori, M. Kanekiyo, A. K. Wheatley, A. B. McDermott, S. K. Farney, G.-Y. Chuang, B. Zhang, N. Kc, S. Chakravarty, P. D. Kwong, P. Sinnis, S. N. Bhatia, S. H. I. Kappe, B. K. L. Sim, S. L. Hoffman, F. Zavala, M. Pancera, R. A. Seder, A human monoclonal antibody prevents malaria infection by targeting a new site of vulnerability on the parasite. Nat. Med. 24, 408-416 (2018).
14. J. Tan, B. K. Sack, D. Oyen, I. Zenklusen, L. Piccoli, S. Barbieri, M. Foglierini, C. S. Fregni, J. Marcandalli, S. Jongo, S. Abdulla, L. Perez, G. Corradin, L. Varani, F. Sallusto, B. K. L. Sim, S. L. Hoffman, S. H. I. Kappe, C. Daubenberger, I. A. Wilson, A. Lanzavecchia, A public antibody lineage that potently inhibits malaria infection through dual binding to the circumsporozoite protein. Nat. Med. 24, 401-407 (2018).
15. The importance of H.Y52A and H.Y58 for repeat reactivity was confirmed by alanine mutations in antibodies 1210, 2140, and 2219 (FIG. 29).
16. All antibodies recognized NANP5 and NANP3 with binding stoichiometries of ~2 and ~1, respectively, demonstrating that NANP5 but not the shorter NANP3 enables binding of two Fabs.
17. C. R. Fisher, H. J. Sutton, J. A. Kaczmarski, H. A. McNamara, B. Clifton, J. Mitchell, Y. Cai, J. N. Dups, N. J. D'Arcy, M. Singh, A. Chuah, T. S. Peat, C. J. Jackson, I. A. Cockburn, T-dependent B cell responses to *Plasmodium* induce antibodies that form a high-avidity multivalent complex with the circumsporozoite protein. PLOS Pathog. 13, e1006469 (2017).
18. B. J. DeKosky, T. Kojima, A. Rodin, W. Charab, G. C. Ippolito, A. D. Ellington, G. Georgiou, In-depth determination and analysis of the human paired heavy- and light-chain antibody repertoire. Nat. Med. 21, 86-91 (2015).
19. C. T. Watson, K. M. Steinberg, J. Huddleston, R. L. Warren, M. Malig, J. Schein, A. J. Willsey, J. B. Joy, J. K. Scott, T. A. Graves, R. K. Wilson, R. A. Holt, E. E. Eichler, F. Breden, Complete haplotype sequence of the human immunoglobulin heavychain variable, diversity, and joining genes and characterization of allelic and copy-number variation. Am. J. Hum. Genet. 92, 530-546 (2013).
20. T. Hattori, D. Lai, I. S. Dementieva, S. P. Montaño, K. Kurosawa, Y. Zheng, L. R. Akin, K. M. Świst-Rosowska, A. T. Grzybowski, A. Koide, K. Krajewski, B. D. Strahl, N. L. Kelleher, A. J. Ruthenburg, S. Koide, Antigen clasping by two antigen-binding sites of an exceptionally specific antibody for histone methylation. Proc. Natl. Acad. Sci. U.S.A. 113, 2092-2097 (2016).

22. G. Yaari, J. A. Vander Heiden, M. Uduman, D. Gadala-Maria, N. Gupta, J. N. H. Stern, K. C. O'Connor, D. A. Hafler, U. Laserson, F. Vigneault, S. H. Kleinstein, Models of somatic hypermutation targeting and substitution based on synonymous mutations
21. H. M. Davies, S. D. Nofal, E. J. Mclaughlin, A. R. Osborne, Repetitive sequences in malaria parasite proteins. FEMS Microbiol. Rev. 41, 923-940 (2017). from high-throughput immunoglobulin sequencing data. Front. Immunol. 4, 358 (2013).
23. N. T. Gupta, J. A. Vander Heiden, M. Uduman, D. Gadala-Maria, G. Yaari, S. H. Kleinstein, Change-O: A toolkit for analyzing large-scale B cell immunoglobulin repertoire sequencing data. Bioinformatics 31, 3356-3358 (2015).
24. A. P. Masella, A. K. Bartram, J. M. Truszkowski, D. G. Brown, J. D. Neufeld, PANDAseq: Paired-end assembler for Illumina sequences. BMC Bioinformatics 13, 31 (2012).
25. T. Tiller, E. Meffre, S. Yurasov, M. Tsuiji, M. C. Nussenzweig, H. Wardemann, Efficient generation of monoclonal antibodies from single human B cells by single cell RT-PCR and expression vector cloning. J. Immunol. Methods 329, 112-124 (2008).
26. K. Tewari, B. J. Flynn, S. B. Boscardin, K. Kastenmueller, A. M. Salazar, C. A. Anderson, V. Soundarapandian, A. Ahumada, T. Keler, S. L. Hoffman, M. C. Nussenzweig, R. M. Steinman, R. A. Seder, Poly(I:C) is an effective adjuvant for antibody and multi-functional CD4+ T cell responses to *Plasmodium falciparum* circumsporozoite protein (CSP) and aDEC-CSP in non human primates. Vaccine 28, 7256-7266 (2010).
27. W. Kabsch, XDS. Acta Crystallogr. D 66, 125-132 (2010).
28. A. J. McCoy, R. W. Grosse-Kunstleve, P. D. Adams, M. D. Winn, L. C. Storoni, R. J. Read, Phaser crystallographic software. J. Appl. Crystallogr. 40, 658-674 (2007).
29. P. D. Adams, P. V. Afonine, G. Bunkóczi, V. B. Chen, I. W. Davis, N. Echols, J. J. Headd, L.-W. Hung, G. J. Kapral, R. W. Grosse-Kunstleve, A. J. McCoy, N. W. Moriarty, R. Oeffner, R. J. Read, D. C. Richardson, J. S. Richardson, T. C. Terwilliger, P. H. Zwart, PHENIX: A comprehensive Python-based system for macromolecular structure solution. Acta Crystallogr. D 66, 213-221 (2010).
30. P. Emsley, B. Lohkamp, W. G. Scott, K. Cowtan, Features and development of Coot. Acta Crystallogr. D 66, 486-501 (2010).
31. A. Morin, B. Eisenbraun, J. Key, P. C. Sanschagrin, M. A. Timony, M. Ottaviano, P. Sliz, Collaboration gets the most out of software. Elife 2, e01456 (2013).
32. S. H. W. Scheres, A Bayesian view on cryo-EM structure determination. J. Mol. Biol. 415, 406-418 (2012).
33. S. Meixlsperger, F. Köhler, T. Wossning, M. Reppel, M. Müschen, H. Jumaa, Conventional light chains inhibit the autonomous signaling capacity of the B cell receptor. Immunity 26, 323-333 (2007).
34. F. Köhler, E. Hug, C. Eschbach, S. Meixlsperger, E. Hobeika, J. Kofer, H. Wardemann, H. Jumaa, Autoreactive B cell receptors mimic autonomous pre-B cell receptor signaling and induce proliferation of early B cells. Immunity 29, 912-921 (2008).
35. H. Wardemann, S. Yurasov, A. Schaefer, J. W. Young, E. Meffre, M. C. Nussenzweig, Predominant autoantibody production by early human B cell precursors. Science 301, 1374-1377 (2003)

Example 5: Immunization Experiments

FIG. 38 shows that the malaria vaccine antigen (CSP-NANP5.5-linker-antibody) elicits IgG titers that can recognize the full-length PfCSP antigen. As expected, the response is boostable and increases through the three doses. In these two examples, the malaria vaccine is displayed on two different nanoparticles, one leading to stronger immune responses than the other. FIG. 39 shows the activity/function of the elicited anti-PfCSP sera from the immunizations in FIG. 38. This is measured in a sporozoite traversal inhibition assay. At a given sera dilution, the inhibitory activity varies between 50 and 80%, depending on how the malaria vaccine is presented on the nanoparticles. These results demonstrate that 1) the malaria vaccine described herein induces antimalarial immune responses and that 2) the resulting immune sera has inhibitory capacity against sporozoites.

What is claimed is:

1. A fusion protein comprising an antibody fragment consisting of a single-chain Fc (scFc), wherein the antibody fragment is fused to a nanocage monomer via a linker.

2. The fusion protein of claim 1, wherein the nanocage monomer comprises a ferritin chain.

3. The fusion protein of claim 1, wherein the linker comprises from 1 to 30 amino acid residues.

4. The fusion protein of claim 3, wherein the linker comprises a GGS repeat.

5. A nanocage comprising at least one fusion protein of claim 1.

6. The nanocage of claim 5, wherein the nanocage is multivalent.

7. The nanocage of claim 5, comprising from 3 to 100 nanocage monomers.

* * * * *